US012780818B2

(12) United States Patent
Wang et al.

(10) Patent No.: US 12,780,818 B2
(45) Date of Patent: Nov. 3, 2026

(54) EPOXYAMIDES AS KRAS G12C AND KRAS G12D INHIBITORS AND METHODS OF USING THE SAME

(71) Applicant: AMGEN INC., Thousand Oaks, CA (US)

(72) Inventors: Hui-Ling Wang, Thousand Oaks, CA (US); Victor J. Cee, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 548 days.

(21) Appl. No.: 17/769,631

(22) PCT Filed: Oct. 22, 2020

(86) PCT No.: PCT/US2020/056874

§ 371 (c)(1), (2) Date: Apr. 15, 2022

(87) PCT Pub. No.: WO2021/081212

PCT Pub. Date: Apr. 29, 2021

(65) Prior Publication Data

US 2024/0190862 A1 Jun. 13, 2024

Related U.S. Application Data

(60) Provisional application No. 62/925,657, filed on Oct. 24, 2019.

(51) Int. Cl.
*C07D 471/04* (2006.01)
*A61K 45/06* (2006.01)
*C07D 519/00* (2006.01)

(52) U.S. Cl.
CPC ............ *C07D 471/04* (2013.01); *A61K 45/06* (2013.01); *C07D 519/00* (2013.01)

(58) Field of Classification Search
CPC ..... C07D 471/04; C07D 519/00; A61K 45/06
See application file for complete search history.

(56) References Cited

U.S. PATENT DOCUMENTS

| | | | |
|---|---|---|---|
| 10,519,146 | B2 | 12/2019 | Lanman et al. |
| 10,532,042 | B2 | 1/2020 | Lanman et al. |
| 10,640,504 | B2 | 5/2020 | Lanman et al. |
| 11,090,304 | B2 | 8/2021 | Allen et al. |
| 11,285,135 | B2 | 3/2022 | Lanman et al. |
| 11,285,156 | B2 | 3/2022 | Allen et al. |
| 11,306,087 | B2 | 4/2022 | Lanman et al. |
| 11,766,436 | B2 | 9/2023 | Allen et al. |
| 11,905,281 | B2 | 2/2024 | Lanman et al. |
| 11,993,597 | B2 | 5/2024 | Lanman et al. |
| 12,083,121 | B2 | 9/2024 | Allen et al. |
| 12,440,491 | B2 | 10/2025 | Allen et al. |
| 2015/0239900 | A1 | 8/2015 | Li et al. |
| 2018/0177767 | A1 | 6/2018 | Lanman et al. |
| 2018/0334454 | A1 | 11/2018 | Lanman et al. |
| 2019/0077801 | A1 | 3/2019 | Lanman et al. |
| 2020/0055845 | A1 | 2/2020 | Lanman et al. |
| 2022/0168280 | A1 | 6/2022 | Lanman et al. |
| 2022/0175782 | A1 | 6/2022 | Allen et al. |
| 2022/0213101 | A1 | 7/2022 | Lanman et al. |
| 2024/0050430 | A1 | 2/2024 | Allen et al. |
| 2024/0174660 | A1 | 5/2024 | Lanman et al. |
| 2024/0287068 | A1 | 8/2024 | Lanman et al. |
| 2025/0057817 | A1 | 2/2025 | Lanman et al. |
| 2025/0362134 | A1 | 11/2025 | Lanman et al. |

FOREIGN PATENT DOCUMENTS

| | | | |
|---|---|---|---|
| WO | 2015001076 | A1 | 1/2015 |
| WO | 2015054572 | A1 | 4/2015 |
| WO | 2015075483 | A1 | 5/2015 |
| WO | 2016044772 | A1 | 3/2016 |
| WO | 2016164675 | A1 | 10/2016 |
| WO | 2017087528 | A1 | 5/2017 |
| WO | 2017201161 | A1 | 11/2017 |
| WO | 2018119183 | A2 | 6/2018 |
| WO | 2018217651 | A1 | 11/2018 |
| WO | 2019051291 | A1 | 3/2019 |
| WO | 2019213516 | A1 | 11/2019 |
| WO | 2019241157 | A1 | 12/2019 |
| WO | 2020050890 | A2 | 3/2020 |
| WO | 2021081212 | A1 | 4/2021 |

OTHER PUBLICATIONS

Pang, X., & Liu, M. (2016). Defeat mutant KRAS with synthetic lethality. Small GTPases, 8(4), 212-219. (Year: 2016).*
Gura et al., Systems for Identifying New Drugs are Often Faulty. Science, New Series, (1997), 278(5340), 1041-1042 (Year: 1997).*
Johnson et al., Relationships between drug activity in NCI preclinical in vitro and in vivo models and early clinical trials. British Journal of Cancer, (2001), 84(10), 1424-1431 (Year: 2001).*
Notice of Allowance, mailed May 20, 2025, for U.S. Appl. No. 18/213,464, pp. 1-9.
Patani et al., "Bioisosterism: A Rational Approach in Drug Design," *Chem Rev.*, 96(8):3147-3176 (1996).
Shibuya, "Structural Modification of Biologically Active Compounds-1 Bioisosteres of peptides (No. 1)," The Chemical Times 163:16-24(1997).
Examiner-Initiated Interview Summary, mailed Dec. 9, 2021, for U.S. Appl. No. 16/817,109, 1 page.
Final Office Action for U.S. Appl. No. 15/984,855, mailed Mar. 28, 2019, 7 pages.
International Search Report for PCT/US2017/067801, mailed Jul. 25, 2018, 6 pages.

(Continued)

*Primary Examiner* — Renee Claytor
*Assistant Examiner* — Christopher Lindsay Johnson
(74) *Attorney, Agent, or Firm* — Markus Bergauer

(57) ABSTRACT

Provided herein are KRAS G12C and KRAS G12D inhibitors, composition of the same, and methods of using the same. These inhibitors are useful for treating a number of disorders, including pancreatic, colorectal, and lung cancers.

35 Claims, No Drawings

(56) References Cited

OTHER PUBLICATIONS

International Search Report for PCT/US2018/033714, mailed Jul. 17, 2018, 3 pages.
International Search Report for PCT/US2018/050044, mailed Oct. 30, 2018, 7 pages.
International Search Report for PCT/US2019/030593, mailed Aug. 6, 2019, 4 pages.
International Search Report for PCT/US2019/036626, mailed Jun. 2, 2020, 5 pages.
International Search Report for PCT/US2020/056874, mailed Feb. 12, 2021, 7 pages.
Morrissey et al., "Immunotherapy and Novel Combinations in Oncology: Current Landscape, Challenges, and Opportunities," *Clin. Transl. Sci.*, 9(2):89-104 (2016).
Non-Final Office Action (Corrected) for U.S. Appl. No. 16/125,359, mailed Apr. 8, 2019, 13 pages.
Non-Final Office Action for U.S. Appl. No. 15/849,905, mailed Mar. 20, 2019, 18 pages.
Non-Final Office Action for U.S. Appl. No. 15/984,855, mailed Sep. 27, 2018, 25 pages.
Non-Final Office Action for U.S. Appl. No. 16/125,359, mailed Apr. 5, 2019, 13 pages.
Non-Final Office Action for U.S. Appl. No. 16/402,538, mailed Oct. 30, 2019, 12 pages.
Non-Final Office Action for U.S. Appl. No. 16/438,349, mailed Dec. 13, 2019, 15 pages.
Non-Final Office Action for U.S. Appl. No. 16/675,121, mailed Feb. 2, 2021, 10 pages.
Non-Final Office Action for U.S. Appl. No. 16/817,109, mailed Mar. 3, 2021, 12 pages.
Non-Final Office Action for U.S. Appl. No. 17/579,359, mailed Dec. 14, 2023, 13 pages.
Non-Final Office Action for U.S. Appl. No. 17/692,026, mailed May 11, 2023, 17 pages.
Written Opinion for PCT/US2017/067801, mailed Jul. 25, 2018, 10 pages.
Written Opinion for PCT/US2018/033714, mailed Jul. 17, 2018, 5 pages.
Written Opinion for PCT/US2018/050044, mailed Oct. 30, 2018, 7 pages.
Written Opinion for PCT/US2019/030593, mailed Aug. 6, 2019, 5 pages.
Written Opinion for PCT/US2019/036626, mailed Jun. 2, 2020, 12 pages.
Written Opinion for PCT/US2020/056874, mailed Feb. 12, 2021, 10 pages.
"Basic Terminology of Stereochemistry," Pure & Appl. Chem., 68(12):2193-2222 (1996).
Non-Final Office Action for U.S. Appl. No. 18/213,464, mailed Jul. 25, 2024, 18 pages.
Non-Final Office Action for U.S. Appl. No. 18/213,464, mailed Nov. 13, 2024, 13 pages.
Non-Final Office Action for U.S. Appl. No. 19/312,046, mailed Feb. 19, 2026, 9 pages.

* cited by examiner

EPOXYAMIDES AS KRAS G12C AND KRAS G12D INHIBITORS AND METHODS OF USING THE SAME

CROSS-REFERENCE TO RELATED APPLICATIONS

This application is a national stage application under 35 U.S.C. § 371 of International Application No. PCT/US2020/056874, having an international filing date of Oct. 22, 2020, which claims the benefit of U.S. Provisional Application No. 62/925,657, filed on Oct. 24, 2019, which is incorporated by reference herein in its entirety.

FIELD OF THE INVENTION

The present invention relates to compounds that inhibit the KRAS G12C and KRAS G12D proteins; methods of treating diseases or conditions, such as cancer, using the compounds; and pharmaceutical compositions containing the compounds.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 13% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

The compounds disclosed herein can be in the form of a pharmaceutically acceptable salt. The compounds provided can be formulated into a pharmaceutical composition comprising a compound disclosed herein and a pharmaceutically acceptable excipient.

Also provided is a method of inhibiting KRAS G12C in a cell, comprising contacting the cell with a compound or composition disclosed herein. Also provided is a method of inhibiting KRAS G12D in a cell, comprising contacting the cell with a compound or composition disclosed herein. The KRAS G12D mutation arises from a single nucleotide change (c.35G>A) and results in an amino acid substitution of the glycine (G) at position 12 by an aspartic acid (D). KRAS G12D is present in 3.99% of AACR GENIE cases, with colorectal adenocarcinoma, pancreatic exocrine neoplasm, non-small cell lung carcinoma, uterine corpus neoplasm, and ovarian neoplasm having the greatest prevalence. Further provided is a method of treating cancer in a subject comprising administering to the subject a therapeutically effective amount of a compound or composition disclosed herein. In some embodiments, the cancer is lung cancer, pancreatic cancer, or colorectal cancer.

SUMMARY

One aspect of the present invention provides various compounds, stereoisomers, atropisomers, pharmaceutically acceptable salts, pharmaceutically acceptable salts of the stereoisomers, and pharmaceutically acceptable salts of the atropisomers as described in the embodiments set forth below.

Another aspect of the present invention provides a pharmaceutical composition that includes the compound of any of the embodiments or the pharmaceutically acceptable salt thereof, and a pharmaceutically acceptable carrier or diluent.

Another aspect of the present invention provides a method of treating cancer. Such methods include: administering to a patient in need thereof a therapeutically effective amount of the compound of any of the embodiments or a pharmaceutically acceptable salt thereof. In some such methods, the cancer is a hematologic malignancy. In some such methods, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In some other such methods, the cancer is multiple myeloma. In some other such methods, the cancer is acute myelogenous leukemia. In some other such methods, the cancer is non-Hodgkin's lymphoma. In another aspect, the method further includes administering to a patient in need thereof a therapeutically effective amount of an additional pharmaceutically active compound. For example, in some such methods the additional pharmaceutically active compound is pembrolizumab. In others, the additional pharmaceutically active compound is nivolumab. In still other such methods, the additional pharmaceutically active compound is trametinib. In still other such methods, the additional pharmaceutically active compound is RMC-4630. In still other such methods, the additional pharmaceutically active compound is AMG 404.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the Claims.

DETAILED DESCRIPTION

Definitions

Abbreviations: The Following Abbreviations May be Used Herein

| | |
|---|---|
| AcOH | acetic acid |
| aq or aq. | aqueous |
| BOC or Boc | tert-butyloxycarbonyl |
| CPhos | 2-dicyclohexylphosphino-2',6'-bis(N,N-dimethylamino)biphenyl |
| cpme | cyclopentyl methyl ether |
| DCE | 1,2-dichloroethane |
| DABCO | 1,4-diazabicyclo[2.2.2]octane |

-continued

| | |
|---|---|
| DCM | dichloromethane |
| DMA | N,N-dimethylacetamide |
| DMAP | 4-dimethylaminopyridine |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | equivalent |
| ESI or ES | electrospray ionization |
| Et | ethyl |
| $Et_2O$ | diethyl ether |
| EtOAc | ethyl acetate |
| g | gram(s) |
| h | hour(s) |
| HBTU | N,N,N',N'-tetramethyl-O-(1H-benzotriazol-1-yl)uronium hexafluorophosphate, O-(benzotriazol-1-yl)-N,N,N',N'-tetramethyluronium hexafluorophosphate |
| HPLC | high pressure liquid chromatography |
| iPr | isopropyl |
| $iPr_2NEt$ or DIPEA | N-ethyl diisopropylamine (Hünig's base) |
| KHMDS | potassium hexamethyldisilazide |
| KOAc | potassium acetate |
| Lawesson's reagent | 2,4-bis(4-methoxyphenyl)-2,4-dithioxo-1,3,2,4-dithiadiphosphetane, 2,4-bis-(4-methoxyphenyl)-1,3-dithia-2,4-diphosphetane 2,4-disulfide |
| LC MS, LCMS, LC-MS or LC/MS | liquid chromatography mass spectroscopy |
| LG | leaving group (e.g., halogen, mesylate, triflate) |
| LHMDS or LiHMDS | lithium hexamethyldisilazide |
| m/z | mass divided by charge |
| Me | methyl |
| MeCN | acetonitrile |
| MeOH | methanol |
| Met | metal species for cross-coupling (e.g., MgX, ZnX, $SnR_3$, $SiR_3$, $B(OR)_2$) |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| $Pd_2(dba)_3$ | tris(dibenzylideneacetone)dipalladium(0) |
| Pd(dppf)$Cl_2$•DCM, Pd(dppf)$Cl_2$ | [1,1'-bis(diphenylphosphino)ferrocene] dichloropalladium(II), complex with dichloromethane |
| $Pd(PPh_3)_4$ | tetrakis(triphenylphosphine)palladium(0) |
| Ph | phenyl |
| PR or PG or Prot. group | protecting group |
| rbf | round-bottomed flask |
| RP-HPLC | reverse phase high pressure liquid chromatography |
| RT or rt or r.t. | room temperature |
| sat. or satd. | saturated |
| SFC | supercritical fluid chromatography |
| SPhos Pd G3 or SPhos G3 | (2-dicyclohexylphosphino-2',6'-dimethoxybiphenyl) [2-(2'-amino-1,1'-biphenyl)]palladium(II) methanesulfonate |
| TBAF | tetra-n-butylammonium fluoride |
| TBTU | N,N,N',N'-tetramethyl-O-(benzotriazol-1-yl)uronium tetrafluoroborate |
| t-BuOH | tert-butanol |
| TEA or $Et_3N$ | trimethylamine |
| TFA | trifluoroacetic acid |
| THF | tetrahydrofuran |
| UV | ultraviolet |

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-C8 hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term Cm-n means the alkyl group has "in" to "n" carbon atoms. The term "alkylene" refers to an alkyl group having a substituent. An alkyl (e.g., methyl), or alkylene (e.g., —CH2-), group can be substituted with one or more, and typically one to three, of independently selected, for example, halo, trifluoromethyl, trifluoromethoxy, hydroxy, alkoxy, nitro, cyano, alkylamino, C1-6alkyl, C2-6alkenyl, C2-6alkynyl, —NC, amino, —CO2H, —CO2C1-C6alkyl, —OCOC1-C6alkyl, C3-C10 cycloalkyl, C3-C10 heterocycloalkyl, C5-C10aryl, and C5-C10 heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —NR2 group, wherein each R is, e.g., H or a substituent. In some embodiments, the amino group is further substituted to form an ammonium ion, e.g., NR3+. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxylate, amine, and amide. An "amide" or "amido" group interchangeably refers to a group similar to an amine or amino group but further including a C(O), e.g., —C(O)$NR_2$. Some contemplated amino or amido groups (some with optional alkylene groups, e.g., alkylene-amino, or alkylene-amido) include $CH_2NH_2$, $CH(CH_3)NH_2$, $CH(CH_3)_2NH_2$, $CH_2CH_2NH_2$, $CH_2CH_2N(CH_3)_2$, $CH_2NHCH_3$, $C(O)NHCH_3$, $C(O)N(CH_3)_2$, CH2C(O)NH-phenyl, $CH_2NHC(O)CH_3$, $CH_2NHCH_2CH_2OH$, $CH_2NHCH_2CO_2H$, CH2NH(CH3)CH2$CO_2CH_3$, $CH_2NHCH_2CH_2OCH_3$, $CH_2NH(CH_3)CH_2CH_2OCH_3$, $CH_2NH(CH_3)CH_2C(O)N(CH_3)_2$, $CH_2NH(CH_3)CH_2C(O)NHCH_3$, $CH_2CH_2CCH$, CH2$NMe_2$, $CH_2NH(CH_3)CH_2CH_2OH$, $CH_2NH(CH_3)CH_2CH_2F$, $CH_2N^+(CH_3)_3$, $CH_2NHCH_2CHF_2$, $CH_2NHCH_2CH_3$,

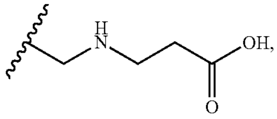
,

-continued

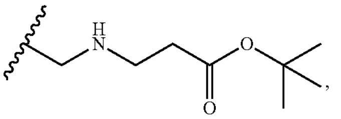

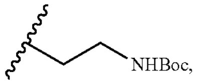

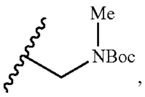
,

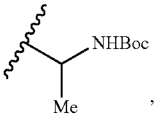
,

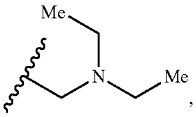
,

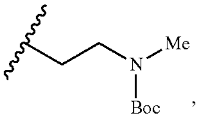
,

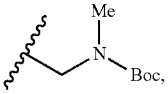

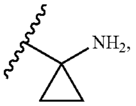

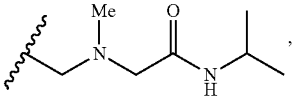
,

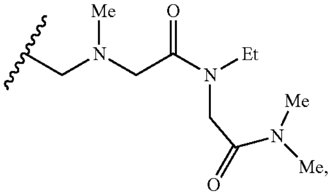

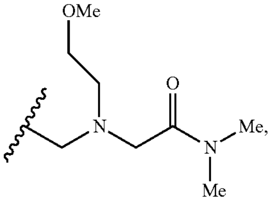

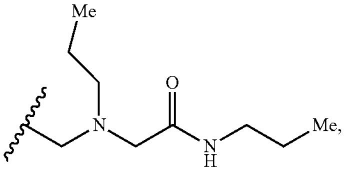

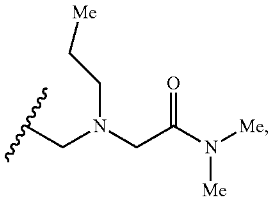

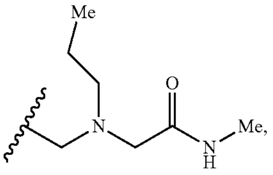

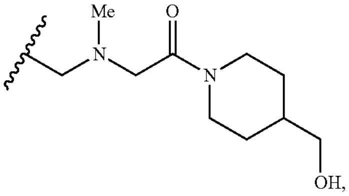

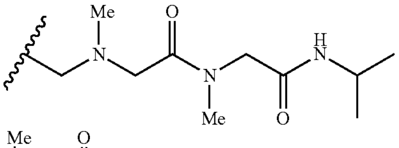
,

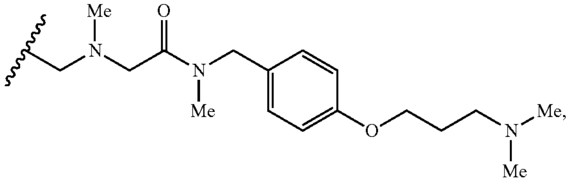

-continued

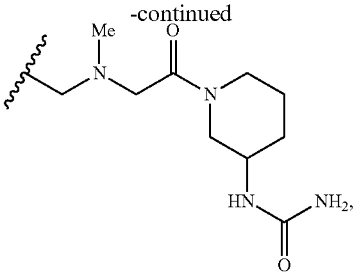

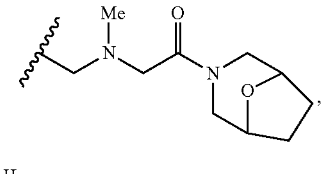

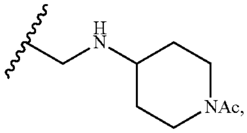

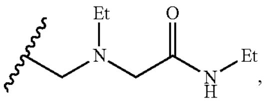
,

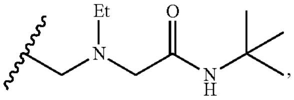
, or

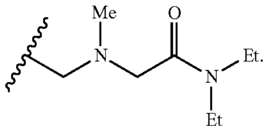

As used herein, the term "aryl" refers to a C6-14 monocyclic or polycyclic aromatic group, preferably a C6-10 monocyclic or bicyclic aromatic group, or C10-14 polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to C10-14 bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, C1-6alkyl, C2-6alkenyl, C2-6alkynyl, —CF3, —OCF3, —NO2, —CN, —NC, —OH, alkoxy, amino, —CO2H, —CO2C1-C6alkyl, —OCOC1-C6alkyl, C3-C10 cycloalkyl, C3-C10 heterocycloalkyl, C5-C10aryl, and C5-C10 heteroaryl.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, C1-6alkyl, C2-6alkenyl, C2-6alkynyl, —OCF3, —NO2, —CN, —NC, —OH, alkoxy, amino, —CO2H, —CO2C1-C6alkyl, —OCOC1-C6alkyl, C3-C10 cycloalkyl, C3-C10 heterocycloalkyl, C5-C10aryl, and C5-C10 heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to C10-14 bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, C1-6alkyl, C2-6alkenyl, C2-6alkynyl, —OCF3, —NO2, —CN, —NC, —OH, alkoxy, amino, —CO2H, —CO2C1-C6alkyl, —OCOC1-C8alkyl, C3-C10 cycloalkyl, C3-C10 heterocycloalkyl, C5-C10aryl, and C5-C10 heteroaryl.

As used herein, the term Boc refers to the structure

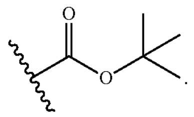 [SMILES: *C(=O)OC(C)(C)C]

As used herein, the term Cbz refers to the structure

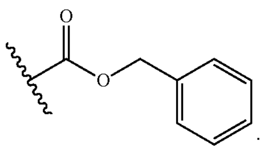 [SMILES: *C(=O)OCc1ccccc1]

As used herein, the term Bn refers to the structure

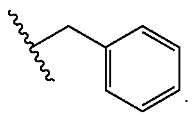 [SMILES: *Cc1ccccc1]

As used herein, the term trifluoroacetamide refers to the structure

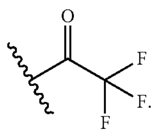 [SMILES: *C(=O)C(F)(F)F]

As used herein, the term trityl refers to the structure

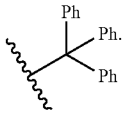 [SMILES: *C(c1ccccc1)(c1ccccc1)c1ccccc1]

As used herein, the term tosyl refers to the structure

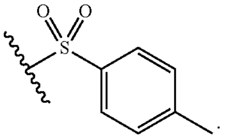 [SMILES: *S(=O)(=O)c1ccc(C)cc1]

As used herein, the term Troc refers to the structure

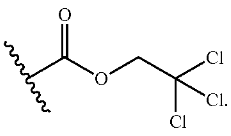 [SMILES: *C(=O)OCC(Cl)(Cl)Cl]

As used herein, the term Teoc refers to the structure

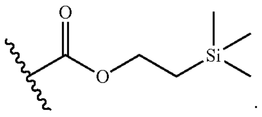 [SMILES: *C(=O)OCC[Si](C)(C)C]

As used herein, the term Alloc refers to the structure

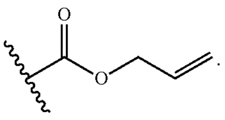 [SMILES: *C(=O)OCC=C]

As used herein, the term Fmoc refers to the structure.

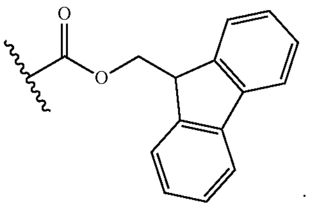 [SMILES: *C(=O)OCC1c2ccccc2-c2ccccc21]

Compounds of the disclosure

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as 2H, 3H, 11C, 13C, 14C, 13N, 15N, 15O, 17O, 18O, 31P, 32P, 35S, 18F, 36Cl, 123I, and 125I, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. 3H, and carbon-14, i.e. 14C, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence are preferred in some circumstances.

Substitution with positron emitting isotopes, such as 11C, 18F, 150 and 13N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. For example, groups such as, but not limited to, the following R10 groups,

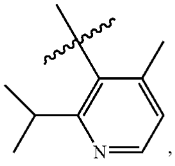
,
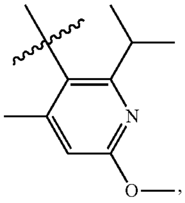
, and

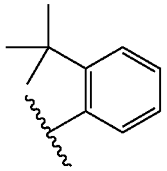

may exhibit restricted rotation.

EMBODIMENTS

Embodiment 1

In one embodiment of the present invention, the present invention comprises a compound having a structure of formula (I)

(I)

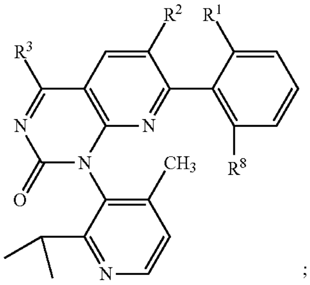
;

wherein $R^1$ is H, halo, or —$CH_3$;

$R^2$ is H, halo, or —$CH_3$;

$R^3$ is

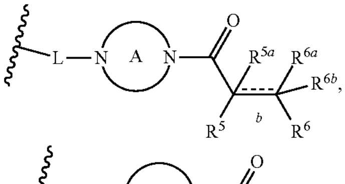
,

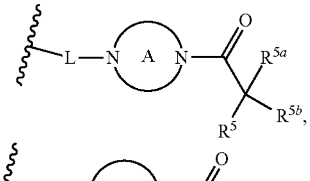
,

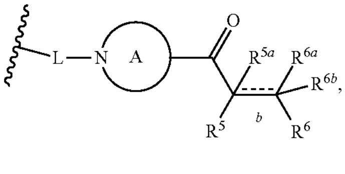
,

-continued

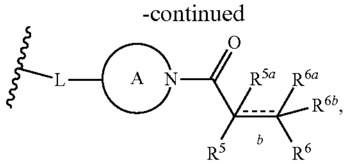

or

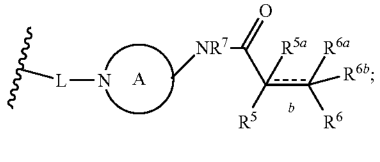

b is optionally a single or a double bond;

ring A is a monocyclic 4-7 membered ring or a bicyclic, bridged, fused, or spiro 6-11 membered ring;

L is a bond or $NR^4$;

$R^4$ is H, —$C_{1-6}$alkyl, —$C_{2-6}$alkynyl, $C_{1-6}$ alkylene-O—$C_{1-6}$alkyl, $C_{1-6}$alkylene-OH, $C_{1-6}$haloalkyl, —$C_{1-6}$alkyleneamine, —$C_{0-6}$ alkylene-amide, —C(O)OH, —C(O)O$C_{1-4}$alkyl, —$C_{1-6}$ alkylene-O-aryl, —N═N, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

$R^5$ is H, halo, an —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)OH, —C(O)$_0$$C_{1-4}$alkyl, —$C_{0-6}$ alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano;

$R^{5a}$ is selected from H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$-haloalkyl, —$C_{1-6}$alkyleneamine, —$C_{0-6}$ alkylene-amide, —C(O)OH, —C(O)O$C_{1-4}$alkyl, —$C_{0-6}$ alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

$R^{5b}$ is selected from H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$ alkylene-amide, —C(O)OH, —C(O)O$C_{1-4}$ alkyl, —$C_{0-6}$ alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

or $R^{5a}$ and $R^{5b}$ together, may represent an ═O or ═N═N;

$R^6$ is H, halo, —$C_{1-6}$alkyl, —$C_{2-6}$alkynyl, —$C_1$— alkylene-O—$C_{1-4}$alkyl, —$C_{1-6}$alkylene-OH, —$C_{1-6}$haloalkyl, —$C_{1-6}$alkyleneamine, —$C_{0-6}$ alkylene-amide, —C(O)OH, —C(O)O$C_{1-4}$alkyl, —$C_{0-6}$ alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

$R^{5a}$ and $R^{6a}$, together with the atoms to which they are attached, may form a 3-6 membered ring that optionally includes one or two heteroatoms selected from O, S or N; or $R^{5a}$ and $R^{6a}$ are absent when b is a double bond;

$R^{6a}$ is H, or —$C_{1-6}$alkyl;

$R^{6b}$ is H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$ haloalkyl, —$C_{1-6}$alkyleneamine, —$C_{0-6}$ alkylene-amide, —C(O)OH, —C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano;

or $R^{6a}$ and $R^{6b}$ together, may represent an ═O;

$R^7$ is H or $C_{1-8}$alkyl;

$R^8$ is H, OH, $NR^aR^b$;

wherein $R^a$ and $R^b$ are each independently H, halo, —$C_{1-6}$alkyl, —$C_{2-6}$alkynyl;

wherein the ring A or the —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$ alkylene-amide, —C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl groups of any of the $R^4$, $R^5$, $R^{5a}$, $R^{5b}$, $R^6$, $R^{6a}$, $R^{6b}$, $R^7$ and $R^8$ may be unsubstituted or substituted with 1, 2, 3, or 4 substituents, as allowed, independently selected from halo, —$C_{1-6}$alkyl, —O—$C_{1-6}$alkyl, —OH, or —$C_{1-6}$alkyl-CN;

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 2

In a second embodiment, the present invention comprises the compound of Embodiment 1, having the structure:

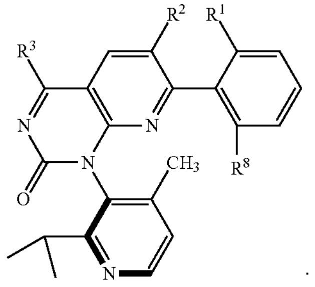

Embodiment 3

The compound of any one of embodiments 1-2, wherein ring A is a monocyclic 4-7 membered ring.

Embodiment 4

The compound of any one of embodiments 1-2, wherein ring A is a or a bicyclic ring.

Embodiment 5

The compound of any one of embodiments 1-2, wherein ring A is a spiro 6-11 membered ring.

Embodiment 6

The compound of any one of embodiments 1-5, wherein $R^1$ is F.

Embodiment 7

The compound of any one of embodiments 1-6, wherein $R^2$ is Cl.

Embodiment 8

The compound of any one of embodiments 1-7, wherein $R^5$ is H, halo, —$C_{1-6}$alkyl, or —$C_{0-3}$alkylene-$C_{6-14}$aryl.

Embodiment 9

The compound of embodiment 8, wherein $R^5$ is H.

Embodiment 10

The compound of embodiment 8, wherein $R^5$ is halo.

Embodiment 11

The compound of embodiment 8, wherein $R^5$ is Cl or F.

Embodiment 12

The compound of embodiment 8, wherein $R^5$ is —$C_{1-6}$alkyl.

Embodiment 13

The compound of embodiment 8, wherein $R^5$ is —$C_{0-3}$alkylene-$C_{6-14}$aryl.

Embodiment 14

The compound of any one of embodiments 1-13, wherein $R^{5a}$ is selected from H, —$C_{1-6}$ alkyl, —$C_{1-6}$alkylene-OH, —C(O)OH, —C(O)O$C_{1-4}$alkyl, and —$C_{0-3}$alkylene-$C_{2-14}$heterocycloalkyl, unless b is a double bond.

Embodiment 15

The compound of embodiment 14, wherein $R^{5a}$ is H.

Embodiment 16

The compound of embodiment 14, wherein $R^{5a}$ is —$C_{1-6}$alkyl.

Embodiment 17

The compound of embodiment 14, wherein $R^{5a}$ is —$C_{1-6}$alkylene-OH.

Embodiment 18

The compound of embodiment 14, wherein $R^{5a}$ is —C(O)OH.

Embodiment 19

The compound of embodiment 14, wherein $R^{5a}$ is —C(O)O$C_{1-4}$alkyl.

Embodiment 20

The compound of embodiment 14, wherein $R^{5a}$ is —$C_{0-3}$alkylene-$C_{2-14}$heterocycloalkyl.

Embodiment 21

The compound of any one of embodiments 1-20, wherein $R^6$ is H, halo, or —$C_{1-6}$alkyl, unless $R^3$ has the following structure

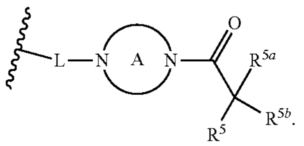

Embodiment 22

The compound of embodiment 21, wherein $R^6$ is H.

Embodiment 23

The compound of embodiment 21, wherein $R^6$ is halo.

Embodiment 24

The compound of embodiment 21, wherein $R^6$ is —$C_{1-6}$alkyl.

Embodiment 25

The compound of any one of embodiments 1-24, wherein $R^{6b}$ is H, —$C_{1-6}$alkyl, $C_{1-6}$alkylene-OH, —C(O)OH, —C(O)O$C_{1-4}$alkyl, or —$C_{0-3}$alkylene-$C_{2-14}$heterocycloalkyl, unless $R^3$ has the following structure

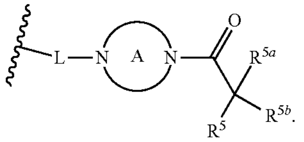

Embodiment 26

The compound of embodiment 25, wherein $R^{6b}$ is H.

Embodiment 27

The compound of embodiment 25, wherein $R^{6b}$ is —$C_{1-6}$alkyl.

Embodiment 28

The compound of embodiment 25, wherein $R^{6b}$ is $C_{1-6}$alkylene-OH.

Embodiment 29

The compound of embodiment 25, wherein $R^{6b}$ is —C(O)OH.

Embodiment 30

The compound of embodiment 25, wherein $R^{6b}$ is —C(O)$OC_{1-4}$alkyl.

Embodiment 31

The compound of embodiment 25, wherein $R^{6b}$ is —$C_{0-3}$alkylene-$C_{2-14}$heterocycloalkyl.

Embodiment 32

The compound of any one of embodiments 1-24, wherein $R^{6a}$ and $R^{6b}$ form a ═O, unless $R^3$ has the following structure

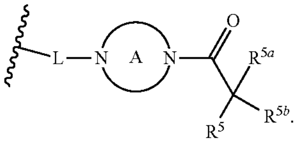

Embodiment 33

The compound of any one of embodiments 1-31, wherein $R^{6a}$ is H, or —$C_{1-6}$alkyl, unless $R^3$ has the following structure

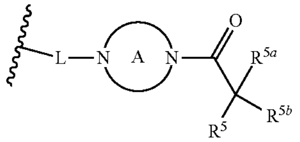

and unless b is a double bond.

Embodiment 34

The compound of embodiment 33, wherein $R^{6a}$ is H.

Embodiment 35

The compound of embodiment 33, wherein $R^{6a}$ is —$C_{1-4}$alkyl.

Embodiment 36

The compound of any one of embodiments 1-35, wherein L is a bond.

Embodiment 37

The compound of any one of embodiments 1-35, wherein L is a $NR^4$.

Embodiment 38

The compound of embodiment 37, wherein $R^4$ is H or —$C_{1-6}$alkyl.

Embodiment 39

The compound of embodiment 37, wherein $R^4$ is H.

Embodiment 40

The compound of embodiment 37, wherein $R^4$ is —$C_{1-6}$alkyl.

Embodiment 41

The compound of any one of embodiments 1-40, wherein b is a single bond.

Embodiment 42

The compound of any one of embodiments 1-40, wherein b is a double bond unless otherwise specified.

Embodiment 43

The compound of any one of embodiments 1-35, wherein $R^3$ is

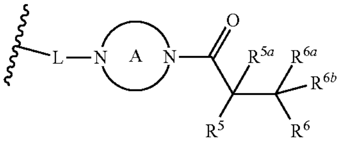

Embodiment 44

The compound of embodiment 43, wherein $R^{5a}$ and $R^{6a}$, together with the atoms to which they are attached, may form a 3-6 membered ring that optionally includes one or two heteroatoms selected from O, S or N.

Embodiment 45

The compound of any one of embodiments 1-35, wherein $R^3$ is

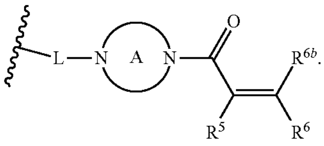

Embodiment 46

The compound of any one of embodiments 1-20, wherein $R^3$ is

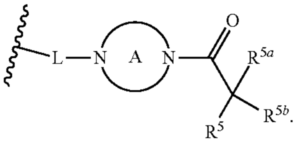

Embodiment 47

The compound of embodiment 46, wherein $R^{5b}$ is selected from H, —$C_{1-6}$alkyl, —$C_{1-6}$alkylene-OH, —C(O)OH, —C(O)O$C_{1-4}$alkyl, or —$C_{0-3}$alkylene-$C_{2-14}$heterocycloalkyl.

Embodiment 48

The compound of embodiment 47, wherein $R^{5b}$ is H.

Embodiment 49

The compound of embodiment 47, wherein $R^{5b}$ is —$C_{1-6}$alkyl.

Embodiment 50

The compound of embodiment 47, wherein $R^{5b}$ is —$C_{1-6}$alkylene-OH.

Embodiment 51

The compound of embodiment 47, wherein $R^{5b}$ is —C(O)OH.

Embodiment 52

The compound of embodiment 47, wherein $R^{5b}$ is —C(O)O$C_{1-4}$alkyl.

Embodiment 53

The compound of embodiment 47, wherein $R^{5b}$ is —$C_{0-3}$alkylene-$C_{2-14}$heterocycloalkyl.

Embodiment 54

The compound of embodiment 46, wherein $R^{5a}$ and $R^{5b}$ together, may represent an =O.

Embodiment 55

The compound of embodiment 46, wherein $R^{5a}$ and $R^{5b}$ together, may represent an =N=N.

Embodiment 56

The compound of any one of embodiments 1-35, wherein $R^3$ is

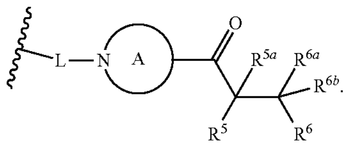

Embodiment 57

The compound of embodiment 56, wherein $R^{5a}$ and $R^{6a}$, together with the atoms to which they are attached, may form a 3-6 membered ring that optionally includes one or two heteroatoms selected from O, S or N.

Embodiment 58

The compound of any one of embodiments 1-35, wherein $R^3$ is

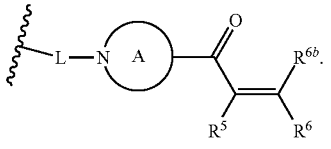

Embodiment 59

The compound of any one of embodiments 1-40, wherein $R^3$ is

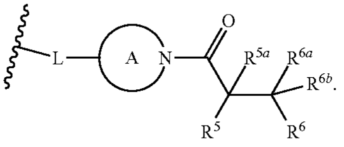

Embodiment 60

The compound of embodiment 59, wherein $R^{5a}$ and $R^{6a}$, together with the atoms to which they are attached, may form a 3-6 membered ring that optionally includes one or two heteroatoms selected from O, S or N.

Embodiment 61

The compound of any one of embodiments 1-40, wherein $R^3$ is

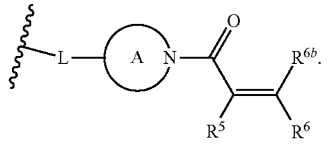

Embodiment 62

The compound of any one of embodiments 1-35, wherein $R^3$ is

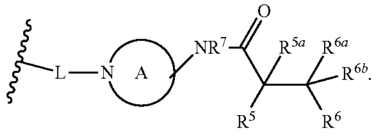

Embodiment 63

The compound of embodiment 62, wherein $R^{5a}$ and $R^{6a}$, together with the atoms to which they are attached, may form a 3-6 membered ring that optionally includes one or two heteroatoms selected from O, S or N.

Embodiment 64
The compound of any one of embodiments 1-35, wherein $R^3$ is
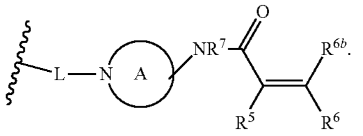
Embodiment 65
The compound of any one of embodiments 62-64, wherein $R^7$ is H or $C_{1-8}$alkyl.
Embodiment 66
The compound of embodiment 65, wherein $R^7$ is H.
Embodiment 67
The compound of embodiment 65, wherein $R^7$ is —$C_{1-8}$alkyl.
Embodiment 68
The compound of any one of embodiments 1-2, wherein $R^3$ is selected from
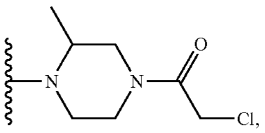
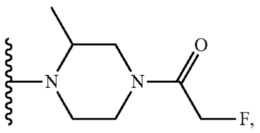
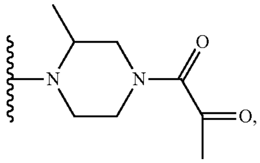
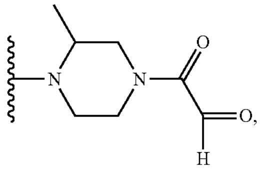
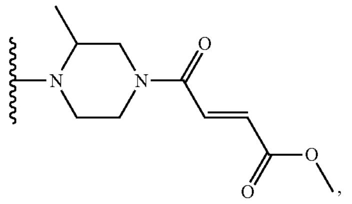
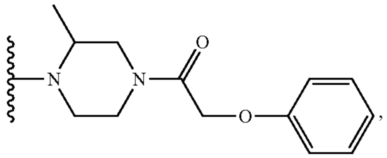
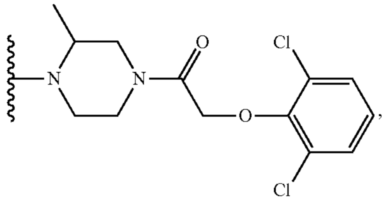
-continued
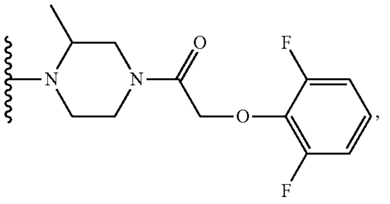
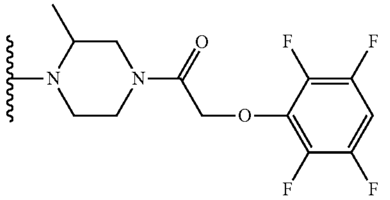
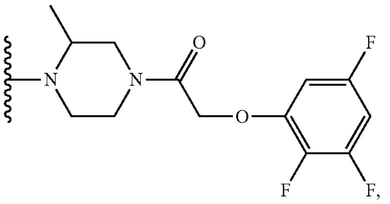
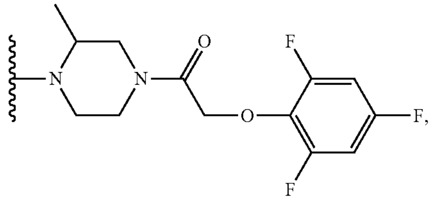
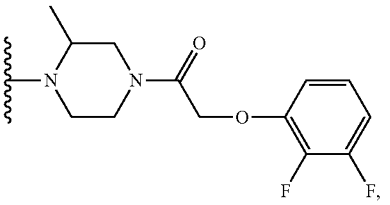
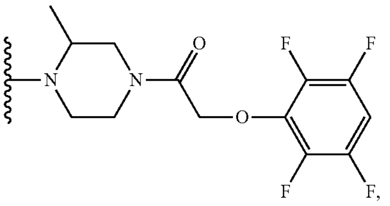
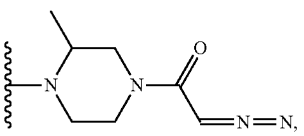
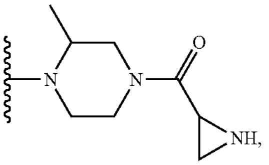
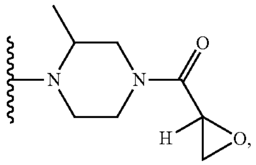
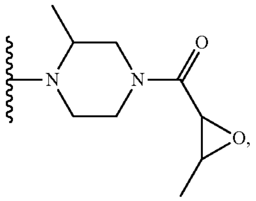

-continued

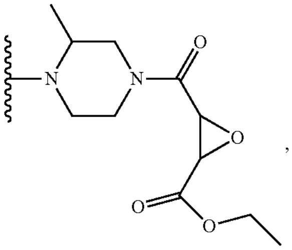
,
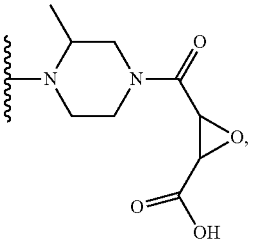

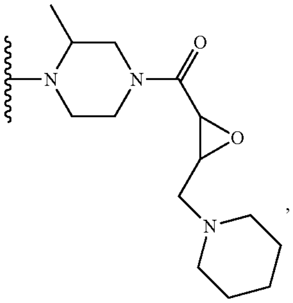
,
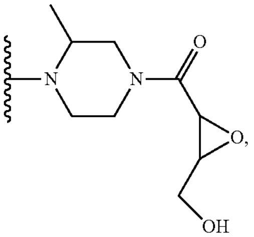

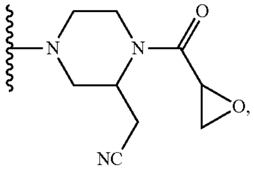

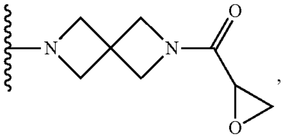
,

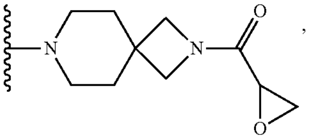
,
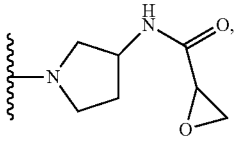

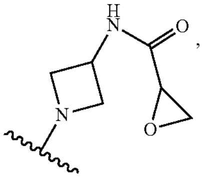
,
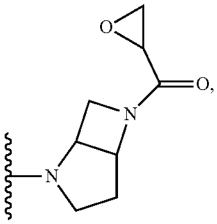

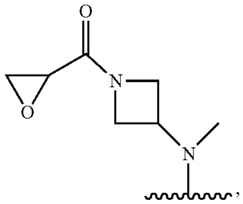
,
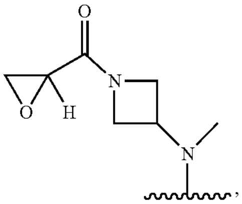
,

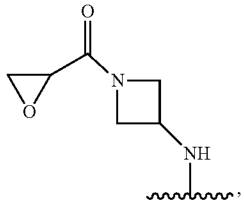
,
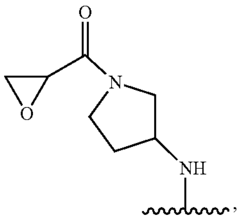
,

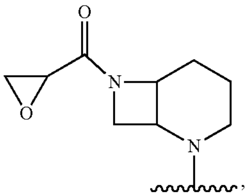
,
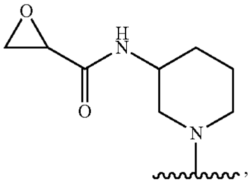
,

-continued

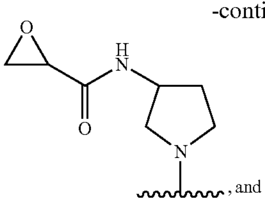
, and
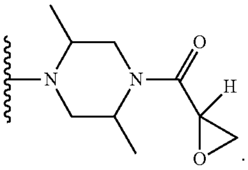
.

Embodiment 69

The compound of embodiment 68, wherein $R^1$ is F.

Embodiment 70

The compound of embodiment 68 or 69, wherein $R^2$ is Cl.

Embodiment 71

The compound of any one of embodiments 1-70, wherein $R^8$ is H.

Embodiment 72

The compound of any one of embodiments 1-70, wherein $R^8$ is OH.

Embodiment 73

The compound of any one of embodiments 1-70, wherein $R^8$ is $NR^aR^b$.

Embodiment 74

The compound of embodiment 73, wherein $NR^aR^b$ is $NH_2$.

Embodiment 75

A compound having a structure selected from:

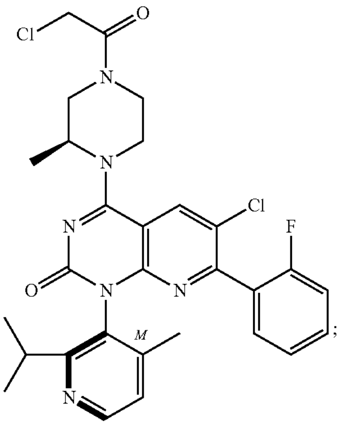
;

-continued
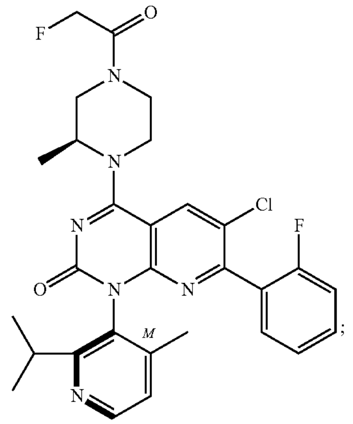
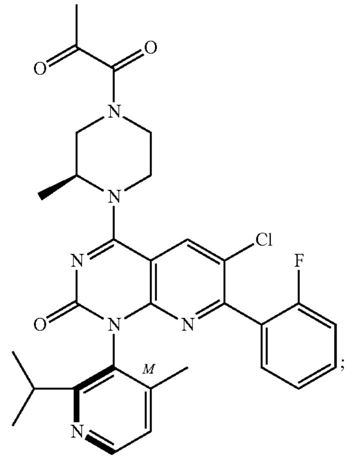
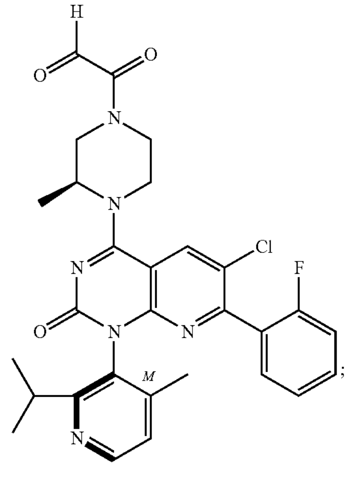
-continued
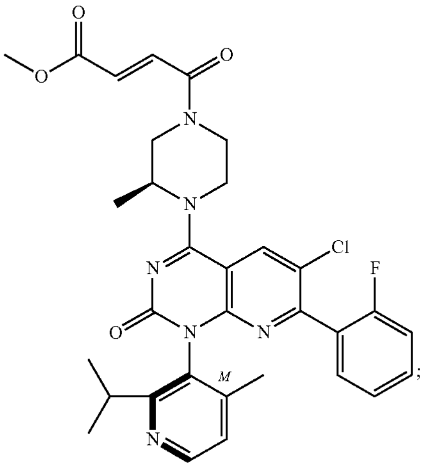
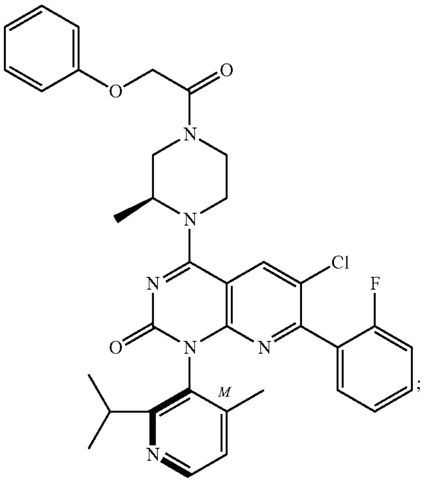
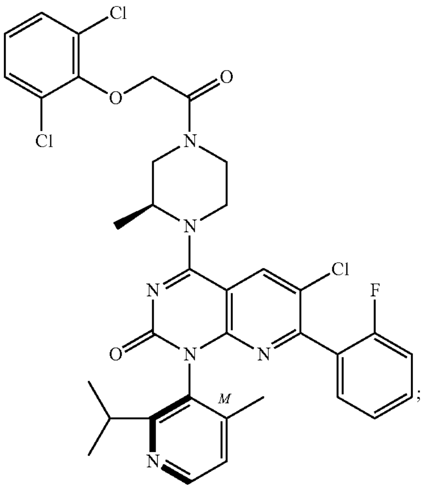

-continued
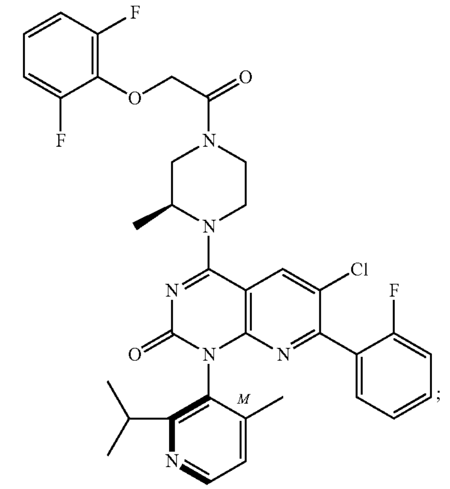
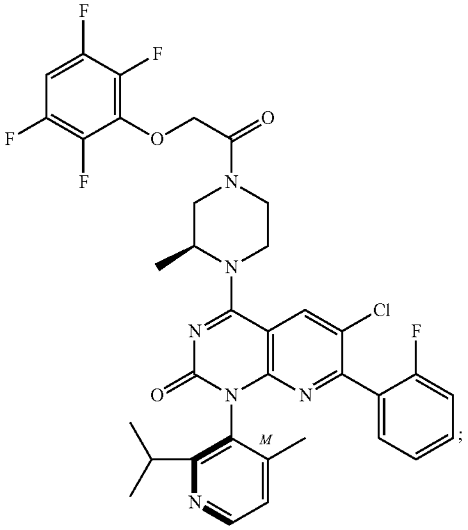
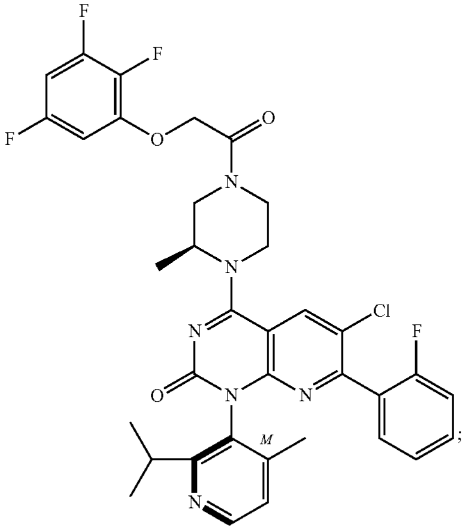
-continued
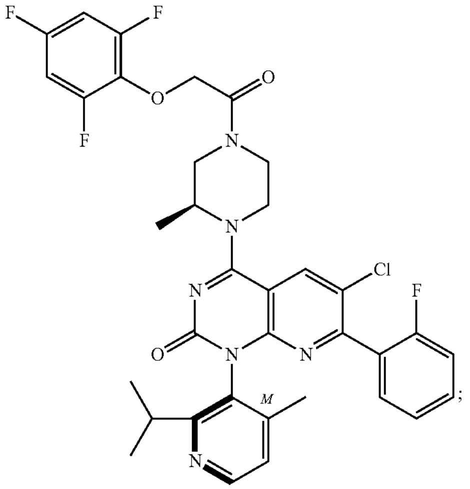
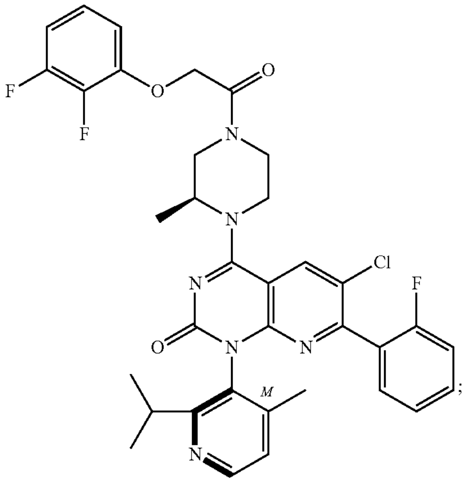
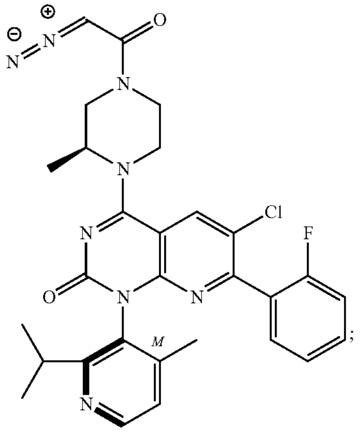

-continued
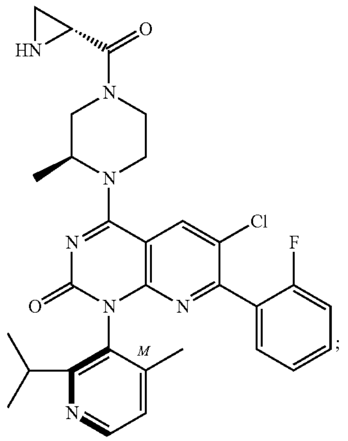
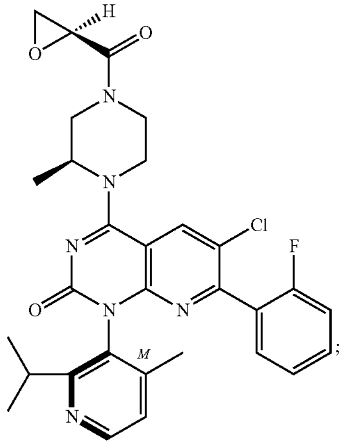
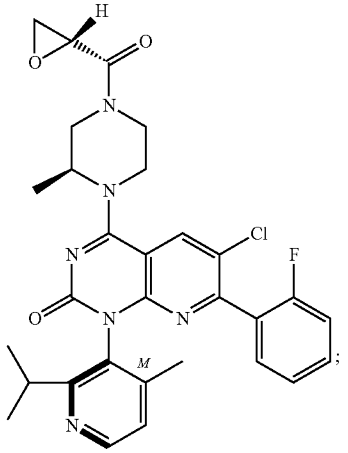
-continued
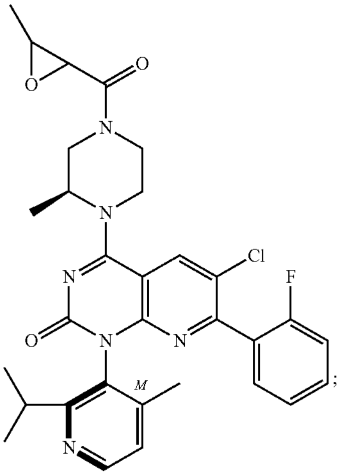
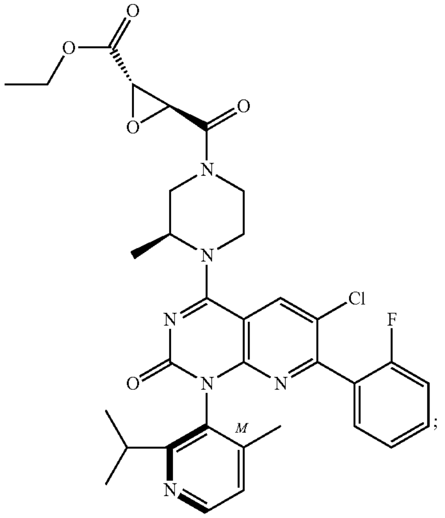
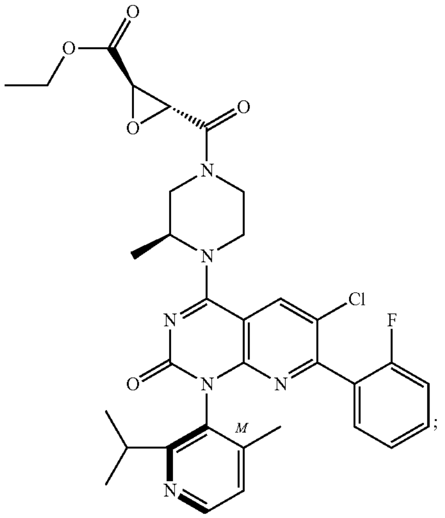

-continued
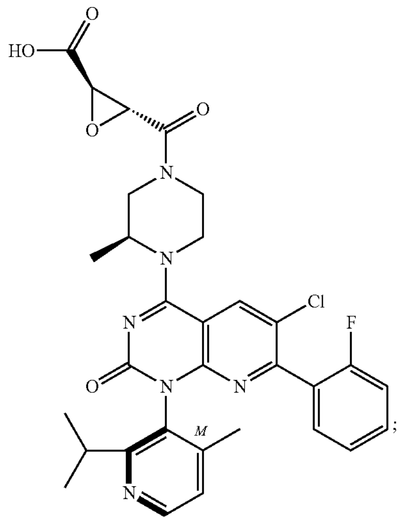
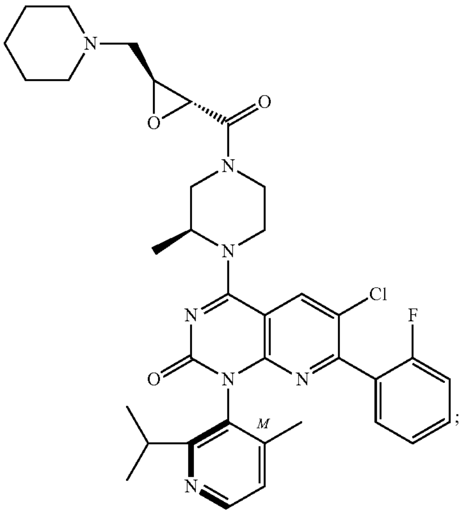
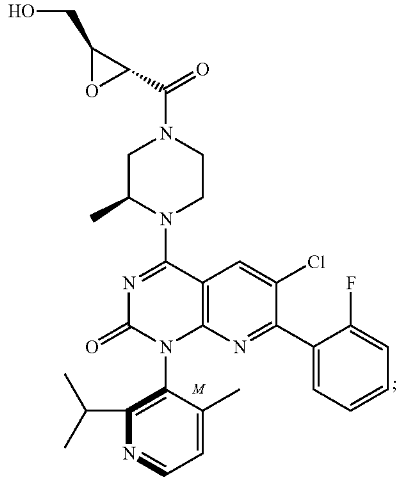
-continued
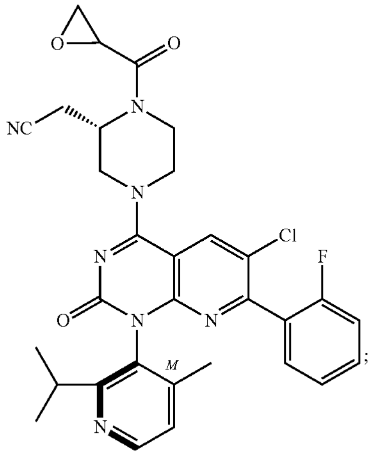
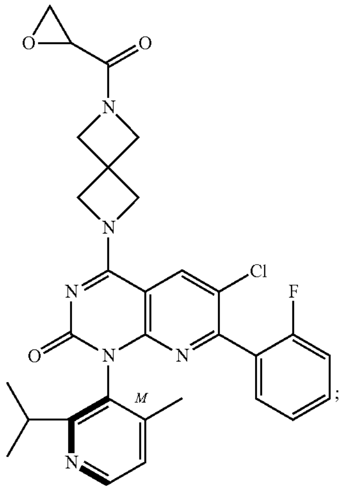
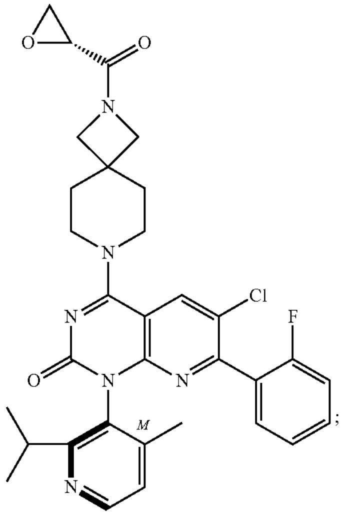

-continued
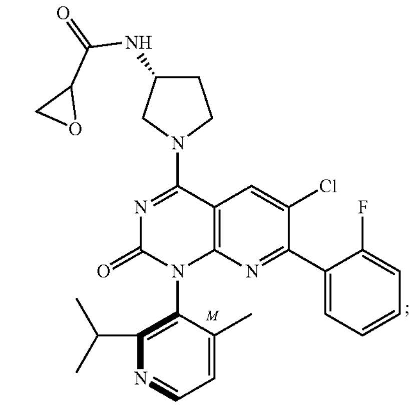
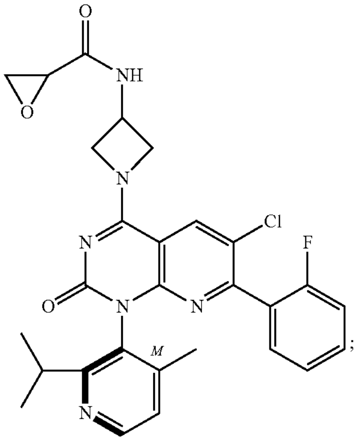
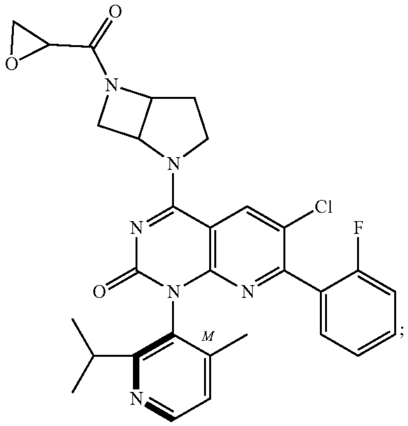
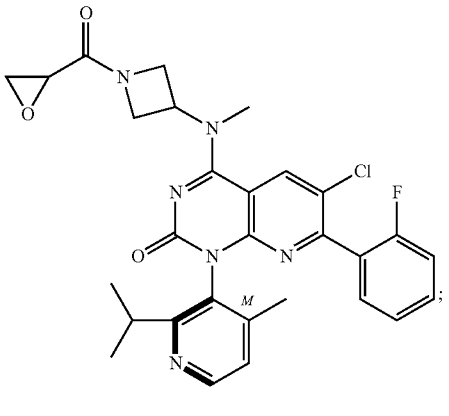
-continued
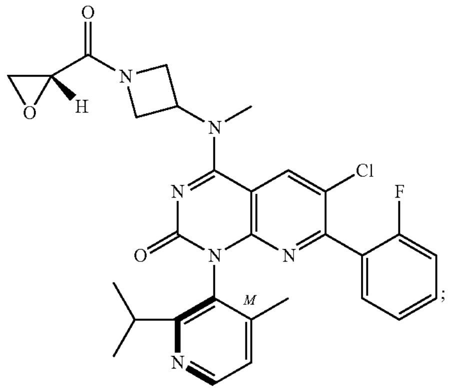
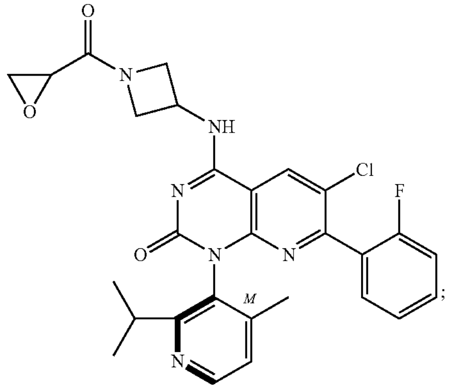
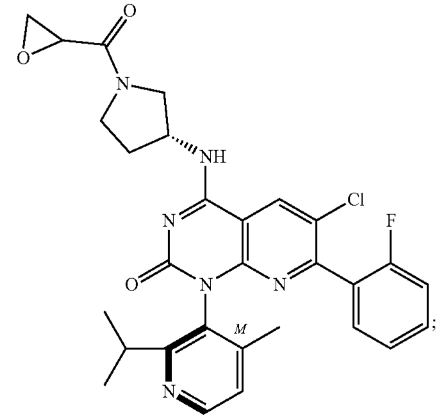
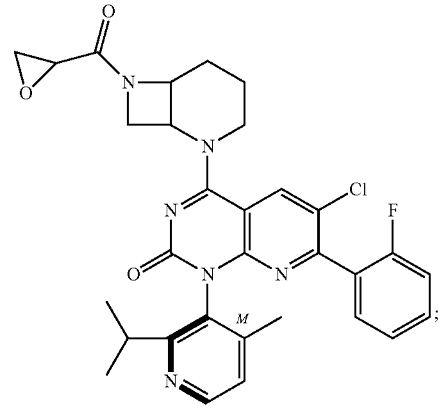

-continued

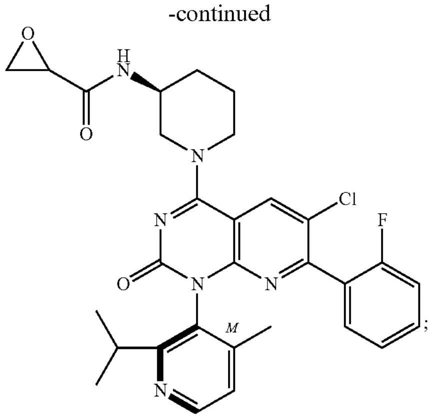

;

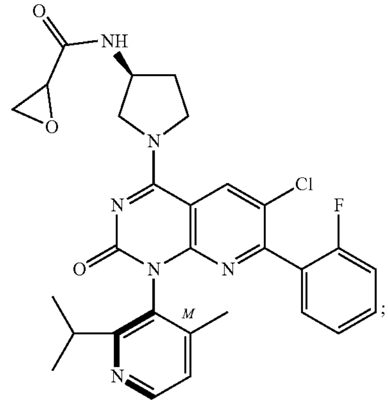

;

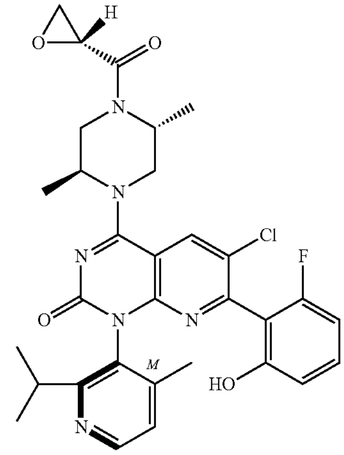

; and

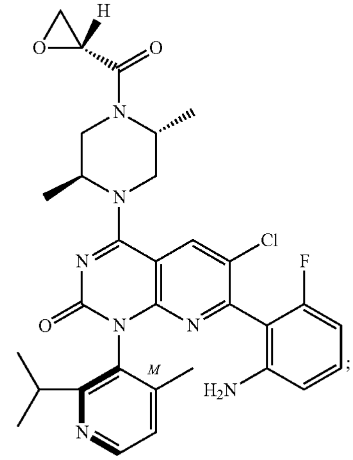

;

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 76

A compound having a structure selected from:

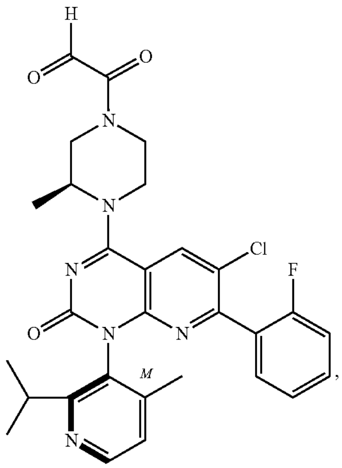

, or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 77

A compound having a structure selected from:

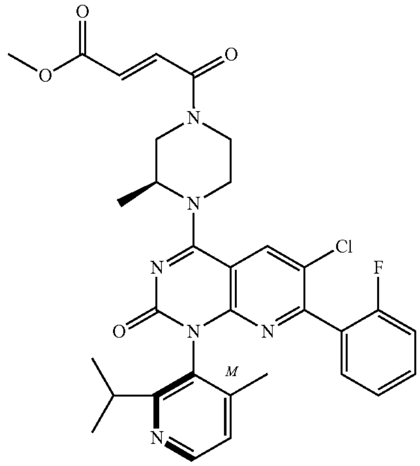

, or a stereoisomer thereof, an atropisomer thereof, a pharmaceutically acceptable salt thereof, a pharmaceutically acceptable salt of the stereoisomer thereof, a pharmaceutically acceptable salt of the atropisomer thereof.

Embodiment 78

A compound having a structure selected from:

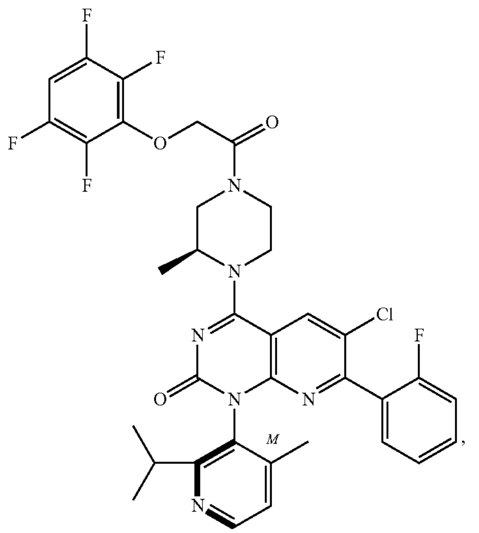

or a stereoisomer thereof, an atropisomer thereof, a pharmaceutically acceptable salt thereof, a pharmaceutically acceptable salt of the stereoisomer thereof, a pharmaceutically acceptable salt of the atropisomer thereof.

Embodiment 79

A compound having a structure selected from:

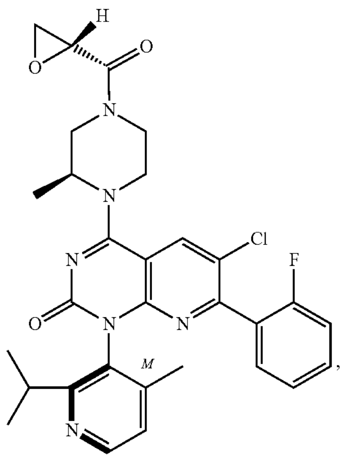

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 80

A compound having a structure selected from:

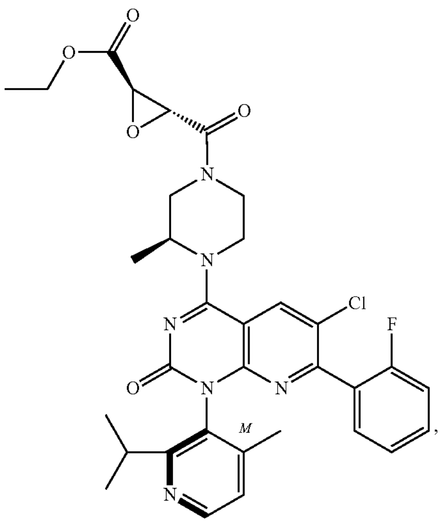

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 81

A compound having a structure selected from:

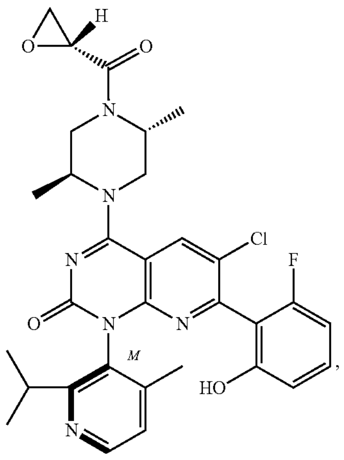

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 82

A compound having a structure selected from:

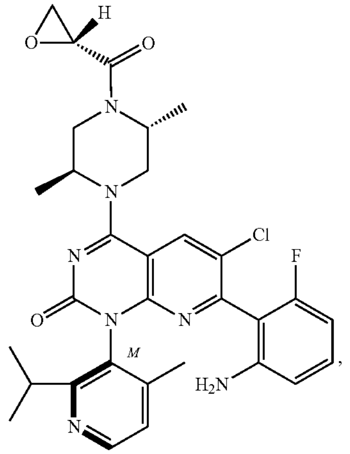

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 83

The compound of any one embodiments 1-80 in the form of a pharmaceutically acceptable salt.

Embodiment 84

A pharmaceutical composition comprising the compound of any one embodiments 1-83 and a pharmaceutically acceptable excipient.

Embodiment 85

A kit for treating cancer, the kit comprising a compound of any one of embodiments 1-84 and an additional pharmaceutical active compound.

Embodiment 86

The kit of embodiment 85 wherein the cancer is a solid tumor.

Embodiment 87

The kit of embodiment 85, wherein the cancer is non-small cell lung cancer.

Embodiment 88

The kit of embodiment 85, wherein the cancer is colorectal cancer.

Embodiment 89

The kit of embodiment 85, wherein the cancer is pancreatic cancer.

Embodiment 90

The kit of embodiment 85, wherein the cancer is a KRAS G12C mutated cancer.

Embodiment 91

The kit of embodiment 85, wherein the cancer is a KRAS G12D mutated cancer.

Embodiment 92

A method of inhibiting KRAS G12C in a cell, comprising contacting the cell with the compound of any one embodiments 1-91.

Embodiment 93

A method of inhibiting KRAS G12D in a cell, comprising contacting the cell with the compound of any one embodiments 1-91.

Embodiment 94

A method of treating cancer in a subject comprising administering to the subject a therapeutically effective amount of the compound of any one embodiments 1-84.

Embodiment 95

The method of embodiment 94 wherein the cancer is a solid tumor cancer.

Embodiment 96

The method of embodiment 94, wherein the cancer is lung cancer, pancreatic cancer, endomentrial cancer, appendicial cancer, small intestine cancer or colorectal cancer.

Embodiment 97

The method of embodiment 96, wherein the cancer is lung cancer.

Embodiment 98

The method of embodiment 96, wherein the lung cancer is non-small cell lung cancer.

Embodiment 99

The method of embodiment 96, wherein the cancer is pancreatic cancer.

Embodiment 100

The method of embodiment 96, wherein the cancer is colorectal cancer.

Embodiment 101

The method of embodiment 96, wherein the cancer is endometrial cancer.

Embodiment 102

The method of embodiment 96, wherein the cancer is appendicial cancer.

Embodiment 103

The method of embodiment 96, wherein the cancer is small intestine cancer.

Embodiment 104

The method of embodiment 94, further comprising administering to the patient in need thereof a therapeutically effective amount of an additional pharmaceutically active compound.

Embodiment 105

The method of embodiment 104, wherein the compound of any one embodiments 1-84 is administered before the additional pharmaceutically active compound.

Embodiment 106

The method of embodiment 96, wherein the compound of any one embodiments 1-84 is administered concurrently with the additional pharmaceutically active compound.

Embodiment 107

The method of embodiment 96, wherein the compound of any one embodiments 1-84 is administered after the additional pharmaceutically active compound.

Embodiment 108

The method of embodiment 104, wherein the additional pharmaceutically active compound is an anti-PD-1 antagonist.

Embodiment 109

The method of embodiment 108, wherein the anti-PD-1 antagonist is nivolumab.

Embodiment 110

The method of embodiment 108, wherein the anti-PD-1 antagonist is pembrolizumab.

Embodiment 111

The method of embodiment 108, wherein the anti-PD-1 antagonist is AMG 404.

Embodiment 112

The method of embodiment 104, wherein the additional pharmaceutically active compound is a MEK inhibitor.

Embodiment 113

The method of embodiment 112, wherein the MEK inhibitor is trametinib.

Embodiment 114

The method of embodiment 104, wherein the additional pharmaceutically active compound is a SHP2 inhibitor.

Embodiment 115

The method of embodiment 114, wherein the SHP2 inhibitor is RMC-4630.

Embodiment 116

Use of a compound according to any one of embodiments 1-84 for treating cancer in a subject.

Embodiment 117

A compound according to any one of embodiments 1-84 in the preparation of a medicament for treating cancer.

Embodiment 118

The compound according to embodiment 116, wherein the cancer is a solid tumor.

Embodiment 119

A compound of any one of embodiments 1-83 or the pharmaceutical composition of embodiment 84 for use as a medicament.

Contemplated halogenating agents include, but are not limited to, chlorine, bromine, N-chlorosuccinimide, and N-bromosuccinimide, optionally in the presence of a catalyst, e.g., iron or aluminum. The ordinarily skilled synthetic chemist will readily understand that other halogenating agents and catalysts can be used.

Contemplated amidating agents include, but are not limited to, N, N'-diisopropylcarbodiimide, N-(3-dimethylaminopropyl)-N'-ethylcarbodiimide, benzotriazol-1-yl-oxytripyrrolidinophosphonium hexafluorophosphate, O-(benzotriazol-1-yl)-N,N,N',N'-tetramethyluronium hexafluorophosphate, thionyl chloride, isobutyl chloroformate, diethyl cyanophosphonate, carbonyl diimidazole, and polyphosphonic anhydride. The ordinarily skilled synthetic chemist will readily understand that other amidating agents can be used.

Contemplated sulfurizing agents include, but are not limited to, sulfur, phosphorus pentasulfide, and Lawesson's reagent. The ordinarily skilled synthetic chemist will readily understand that other sulfurizing agents can be used.

Contemplated oxidants include, but are not limited to, hydrogen peroxide, iodobenzene diacetate, t-butyl hydroperoxide, N-bromosuccinimide, and ammonium peroxodisulfate. The ordinarily skilled synthetic chemist will readily understand that other oxidants can be used.

Contemplated metalating agents include, but are not limited to, bis(pinacolato)diboron, magnesium, zinc, hexamethyldistannane, and n-butyllithium. The ordinarily skilled synthetic chemist will readily understand that other metalating agents and catalysts can be used.

Contemplated activating agents include, but are not limited to, sodium nitrite and t-butyl nitrite. The ordinarily skilled synthetic chemist will readily understand that other activating agents can be used.

Contemplated cross-coupling reactions include, but are not limited to, Suzuki coupling, Negishi coupling, Hiyama coupling, Kumada coupling, and Stille coupling. The ordinarily skilled chemist will readily understand that couplings as shown in the following Methods can be performed under a number of conditions.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable excipients" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 1000 mg/day, about 5 mg/day to about 500 mg/day, about 10 mg/day to about 200 mg/day, about 3 mg/day to about 100 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, G12D KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C or G12D mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C or G12D mutation and if the subject is determined to have the KRAS, HRAS or NRAS G12C or G12D mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C or G12D mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation or a G12D KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C or G12D KRAS, HRAS or NRAS mutations by real-time PCR. In real-time PCR, fluorescent probes specific for the KRAS, HRAS or NRAS G12C or G12D mutation are used. When a mutation is present, the probe binds and fluorescence is detected. In some embodiments, the KRAS, HRAS or NRAS G12C or G12D mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C or G12D KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as a solid tumor cancer, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urachal cancer, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C and or a G12D Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C and/or G12D Mutant KRAS, HRAS or NRAS protein with an effective amount of a compound of the disclosure in solution. In some embodiments, the disclosure provides methods of inhibiting the G12C or G12D Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C or G12D activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C or G12D in said human. The present disclosure provides methods of treating a disease mediated by KRAS, HRAS or NRAS G12C activity in a subject in need of such treatment. The present disclosure provides methods of treating a disease mediated by KRAS, HRAS or NRAS G12D activity in a subject in need of such treatment.

Combination Therapy:

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect. In one aspect, the method comprises administering to the patient in need thereof a therapeutically effective amount of an additional pharmaceutically active compound. In another aspect, the method comprises administering the compound of the present invention before the administration of at least one additional pharmaceutically active compound. In another aspect, the method comprises administering the compound of the present invention concurrently with the administration of at least one additional pharmaceutically active compound. In another aspect, the method comprises administering the compound of the present invention after the administration of at least one additional pharmaceutically active compound.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), venetoclax, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931788, WO 90/05719, WO 99/52910, WO 99/52889, WO 99/29667, WO 99/007675, European Patent Publication EP1786785, European Patent Publication No. EP1181017, United States Publication US20090012085, United States Publication U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing honnone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, such as (RMC-4630), proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4): 565-8, and Paez J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12):1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, trametinib (Mekinist®), CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) *Biochem. J.,* 385 (Pt. 2), 399-408); Akt-1-1,2 (inhibits Ak1 and 2) (Barnett et al. (2005) *Biochem. J.* 385 (Pt. 2), 399-408); API-59CJ-Ome (e.g., Jin et al. (2004) *Br. J. Cancer* 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134(12 Suppl), 3493S-3498S); perifosine (e.g., interferes with Akt membrane localization; Dasmahapatra et al. (2004) *Clin. Cancer Res.* 10(15), 5242-52, 2004); phosphatidylinositol ether lipid analogues (e.g., Gills and Dennis (2004) *Expert. Opin. Investig. Drugs* 13, 787-97); and triciribine (TCN or API-2 or NCI identifier: NSC 154020; Yang et al. (2004) *Cancer Res.* 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

MCI-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

SHP inhibitors include, but are not limited to, SHP099.

Proteasome inhibitors include, but are not limited to, Kyprolis® (carfilzomib), Velcade®(bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory imide drugs (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., *Blood* 110(1):186-192 (2007), Thompson et al., *Clin. Cancer Res.* 13(6):1757-1761 (2007), and Korman et al., International Application No. PCT/JP2006/309606 (publication no. WO 2006/121168 A1), each of which are expressly incorporated by reference herein, include: pembrolizumab (Keytruda®), nivolumab (Opdivo®), Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG 404, AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Synthesis of Disclosed Compounds

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan. Methods described in publications WO2018/119183, WO2018/217651 (corresponding applications also referenced as International Application number PCT/US/2018/033714 and US Patent Publication Number US 2018/0334454) and WO 2019/051291 can be employed in the present invention and are incorporated herein in their entireties for all purposes.

The following Method, as described in WO2018/217651 and its corresponding US 2018/0334454, is explicitly recited herein to manufacture the intermediate (S)-tert-Butyl-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate. To a solution of (S)-tert-butyl 4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate, which is then employed to make the novel Examples of the present invention.

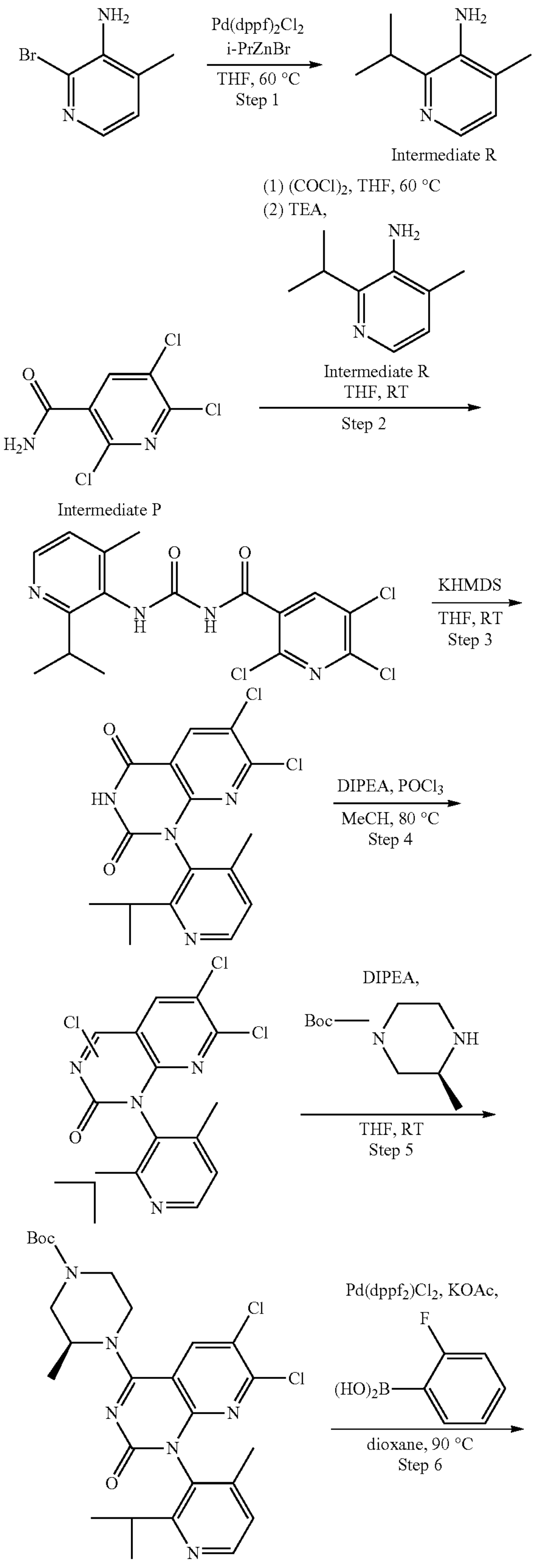

-continued

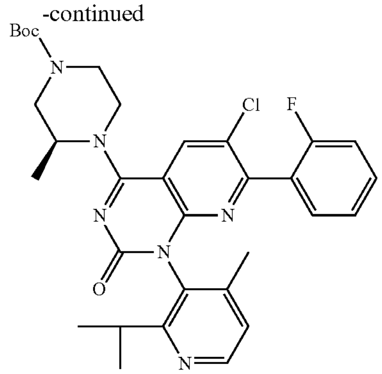

Step 1: 2-Isopropyl-4-methylpyridin-3-amine (Intermediate R). To a slurry of 3-amino-2-bromo-4-picoline (360 mg, 1.9 mmol, Combi-Blocks, San Diego, CA, USA) in THF (4 mL) was added [1,1'-bis(diphenylphosphino)ferrocene]dichloropalladium(II), complex with dichloromethane (79 mg, 0.10 mmol). The resulting slurry was deoxygenated with argon for 2 min and then 2-propylzinc bromide (0.5 M solution in THF, 5.40 mL, 2.7 mmol, Sigma-Aldrich, St. Louis, MO) was added. The resulting solution was heated at 60° C. for 17 h, then the heating was stopped and the reaction was allowed to cool to room temperature. The reaction mixture was quenched with water (10 mL) and 1 N NaOH solution (20 mL) and then was extracted with EtOAc (2×). The combined organic layers were dried over anhydrous sodium sulfate and concentrated. The residue was purified by silica gel chromatography (eluent: 0-15% MeOH/DCM) to provide 2-isopropyl-4-methylpyridin-3-amine. $^1$H NMR (400 MHz, DMSO-d$_6$) δ ppm 7.66 (d, J=4.6 Hz, 1H), 6.78 (d, J=4.8 Hz, 1H), 4.72 (br s, 2H), 3.14-3.25 (m, 1H), 2.08 (s, 3H), 1.14 (d, J=6.8 Hz, 6H). m/z (ESI, +ve ion): 151.1 (M+H)$^+$.

Step 2: 2,5,6-Trichloro-N-((2-isopropyl-4-methylpyridin-3-yl)carbamoyl)nicotinamide. To a −78° C. slurry of 2,5,6-trichloronicotinamide (Intermediate P, 3.10 g, 13.8 mmol) in THE (46 mL) was added oxalyl chloride (2 M solution in DCM, 7.4 mL, 14.7 mmol) slowly via syringe. The resulting slurry was heated at 60° C. for 3.5 h, then heating was stopped and the reaction was cooled to −78° C. Triethylamine (6.0 mL, 42.6 mmol) was added followed by a solution of 2-isopropyl-4-methylpyridin-3-amine (Intermediate R, 2.12 g, 14.1 mmol) via cannula. The resulting slurry was warmed to room temperature and stirred for 1 h, then was partitioned between water (120 mL) and EtOAc (175 mL). The organic layer was dried over anhydrous sodium sulfate and concentrated. The residue was suspended in 9:1 heptane/EtOAc and filtered. The filtered solids were collected to provide 2,5,6-trichloro-N-((2-isopropyl-4-methylpyridin-3-yl)carbamoyl)nicotinamide. $^1$H NMR (400 MHz, DMSO-d$_6$) δ ppm 11.31 (s, 1H), 9.54 (s, 1H), 8.66 (s, 1H), 8.34 (d, J=4.8 Hz, 1H), 7.16 (d, J=5.0 Hz, 1H), 3.24-3.33 (m, 1H), 2.22 (s, 3H), 1.17 (d, J=6.6 Hz, 6H). m/z (ESI, +ve ion): 400.9 (M+H)$^+$.

Step 3: 6,7-Dichloro-1-(2-isopropyl-4-methylpyridin-3-yl)pyrido[2,3-d]pyrimidine-2,4(1H,3H)-dione. To an ice-cooled solution of 2,5,6-trichloro-N-((2-isopropyl-4-methylpyridin-3-yl)carbamoyl)nicotinamide (4.71 g, 11.7 mmol) in THF (55 mL) was added KHMDS (1 M solution in THF, 23.5 mL, 23.5 mmol) slowly via syringe. After 10 min the ice bath was. removed and the resulting solution was stirred for an additional 30 min at room temperature. The reaction was quenched with saturated aqueous ammonium chloride (125 mL) and extracted with EtOAc (250 mL). The organic layer was washed with brine (lx), dried over anhydrous sodium sulfate, and concentrated. The residue was purified by silica gel chromatography (eluent: 0-11% MeOH/DCM) to provide 6,7-dichloro-1-(2-isopropyl-4-methylpyridin-3-yl)pyrido[2,3-d]pyrimidine-2,4(1H,3H)-dione. $^1$H NMR (400 MHz, DMSO-$d_6$) δ ppm 12.27 (br s, 1H), 8.59 (s, 1H), 8.52 (d, J=5.0 Hz, 1H), 7.28 (d, J=5.0 Hz, 1H), 2.82-2.92 (m, 1H), 2.04 (s, 3H), 1.08 (d, J=6.6 Hz, 3H), 1.01 (d, J=6.8 Hz, 3H). m/z (ESI, +ve ion): 365.0 $(M+H)^+$.

Step 4: 4,6,7-Trichloro-1-(2-isopropyl-4-methylpyridin-3-yl)pyrido[2,3-d]pyrimidin-2(1H)-one. To a slurry of 6,7-dichloro-1-(2-isopropyl-4-methylpyridin-3-yl)pyrido[2,3-d]pyrimidine-2,4(1H,3H)-dione (2.52 g, 6.9 mmol) in acetonitrile (45 mL) was added DIPEA (1.80 mL, 10.3 mmol) followed by phosphorus oxychloride (1.58 mL, 10.3 mmol), slowly via syringe. The resulting mixture was heated at 80° C. for 1.75 h, and then was cooled to room temperature and concentrated to provide 4,6,7-trichloro-1-(2-isopropyl-4-methylpyridin-3-yl)pyrido[2,3-d]pyrimidin-2(1H)-one. This material was used without further purification in the following step.

Step 5: (S)-tert-Butyl-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate. To a solution of 4,6,7-trichloro-1-(2-isopropyl-4-methylpyridin-3-yl)pyrido[2,3-d]pyrimidin-2(1H)-one (2.64 g, 6.9 mmol) in THF (40 mL) was added DIPEA (3.61 mL, 20.7 mmol), followed by (S)-4-N-Boc-2-methyl piperazine (2.07 g, 10.3 mmol, Combi-Blocks, Inc., San Diego, CA, USA). The resulting solution was stirred at room temperature for 1.5 h, and then ice water (60 mL) was added. The mixture was stirred for an additional 5 min, then was extracted with EtOAc (3×). The combined organic layers were dried over anhydrous sodium sulfate and concentrated. The residue was purified by silica gel chromatography (eluent: 0-11% MeOH/DCM) to provide (S)-tert-butyl 4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 8.46 (dd, J=11.6, 5.2 Hz, 2H), 7.25 (d, J=4.8 Hz, 1H), 4.79-4.93 (m, 1H), 4.10-4.24 (m, 1H), 3.87-4.05 (m, 1 H), 3.77-3.87 (m, 1H), 3.62-3.76 (m, 1H), 2.99-3.25 (m, 2H), 2.55-2.69 (m, 1H), 1.94 (d, J=2.5 Hz, 3H), 1.45 (s, 9H), 1.32 (br t, J=5.7 Hz, 3H), 1.06 (d, J=6.8 Hz, 3H), 1.00 (d, J=6.6 Hz, 3H). m/z (ESI, +ve ion): 547.2 $(M+H)^+$.

Step 6: (S)-tert-Butyl-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate. To a solution of (S)-tert-butyl 4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (1.02 g, 1.8 mmol) in 1,4-dioxane (17 mL) was added potassium acetate (914 mg, 9.3 mmol) and (2-fluorophenyl)boronic acid (313 mg, 2.2 mmol, Sigma-Aldrich, St. Louis, MO, USA). The mixture was sparged with argon and then [1,1'-bis(diphenylphosphino)ferrocene]dichloropalladium(II), complex with dichloromethane (76 mg, 0.093 mmol) was added. The mixture was again sparged with argon and heated at 90° C. After 30 seconds three drops of water were added to the reaction mixture. Heating was continued at 90° C. for 40 min, and then the reaction was allowed to cool to room temperature. Water (50 mL) and brine (4 mL) were added and the resulting mixture was extracted with EtOAc (2×). The combined organic layers were washed with brine (lx), dried over anhydrous sodium sulfate and concentrated. The residue was purified by silica gel chromatography (eluent: 0-9% MeOH/DCM) to provide (S)-tert-butyl 4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 8.43 (d, J=2.5 Hz, 1H), 8.39 (d, J=4.8 Hz, 1H), 7.47-7.55 (m, 1H), 7.16-7.33 (m, 4H), 4.86-4.97 (m, 1H), 4.21-4.30 (m, 1H), 3.90-4.06 (m, 2H), 3.80-3.89 (m, 1H), 3.67-3.78 (m, 1H), 3.04-3.16 (m, 1H), 2.65-2.75 (m, 1H), 1.93 (s, 3H), 1.48 (s, 9H), 1.36 (br d, J=6.6 Hz, 3H), 1.06 (d, J=6.6 Hz, 3H), 0.94 (dd, J=6.6, 2.1 Hz, 3H). m/z (ESI, +ve ion): 607.0 $(M+H)^+$.

Example 1

(S)-6-Chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one

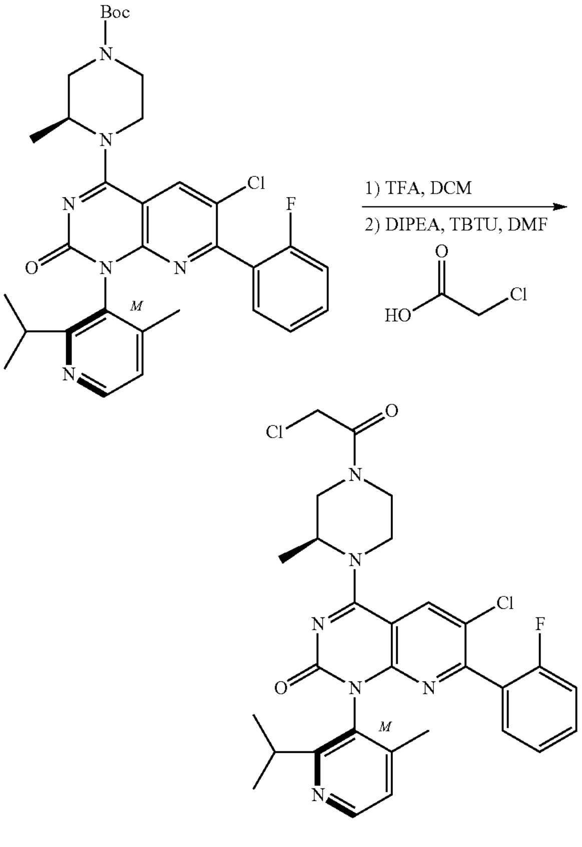

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (US 20180334454 A1) (500 mg, 0.84 mmol) in dichloromethane (3 mL) was treated with trifluoroacetic acid (1.5 mL, 20.1 mmol) at rt and stirred for 15 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.0 $(M+H)^+$.

To a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and chloroacetic acid (156 mg, 1.65 mmol) in DMF (3 mL) at 0° C. was added DIPEA (0.7 mL, 4.12 mmol), followed by TBTU (529 mg, 1.65 mmol). The reaction mixture was stirred at room temperature for 1 h. The resulting mixture was added water (15 mL) and extracted with EtOAc (15 mL×2). The organic extract was washed with satd $NH_4Cl$ (30 mL) and brine (30 mL), and then dried over $MgSO_4$. The solution was filtered and concentrated in vacuo. The crude product was purified by silica gel chromatography (eluent: 0-60% EtOAc-EtOH (3:1)/heptane) to give (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (439 mg, 0.75 mmol, 91% yield, 95% purity) as a light yellow solid. $^{1}H$ NMR (400 MHz, DMSO-$d_6$) δ 8.46 (br d, J=10.8 Hz, 1H), 8.40 (d, J=4.8 Hz, 1 H), 7.44-7.59 (m, 1H), 7.25-7.36 (m, 2H), 7.17-7.24 (m, 2H), 4.87-5.00 (m, 1H), 4.38-4.61 (m, 2H), 4.16-4.36 (m, 2H), 3.63-4.01 (m, 2H), 3.39-3.53 (m, 1H), 3.10-3.27 (m, 1 H), 2.64-2.78 (m, 1H), 1.95 (s, 3H), 1.30-1.47 (m, 3H), 1.08 (d, J=6.6 Hz, 3H), 0.95 (d, J=6.6 Hz, 3H). $^{19}F$ NMR (376 MHz, DMSO-$d_6$) δ ppm −114.03 (d, J=6.1 Hz, 1 F). m/z (ESI, +ve) 582.2 $(M+H)^+$.

Example 2

(S)-6-Chloro-4-(4-(2-fluoroacetyl)-2-methylpiperazin-1-yl)-7-(2-fluorophenyl)-1-(2-isopropyl-4-methylpyridin-3-yl)pyrido[2,3-d]pyrimidin-2(1B)-one

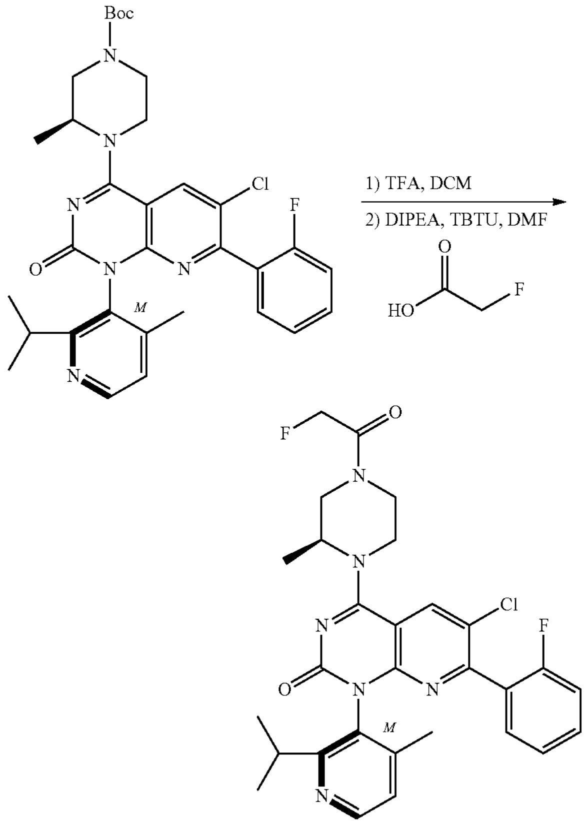

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (US 20180334454 A1) (104 mg, 0.17 mmol) in dichloromethane (1 mL) was treated with trifluoroacetic acid (1 mL, 13.4 mmol) at rt and stirred for 30 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.0 $(M+H)^+$.

To a mixture of (S)-6-chloro-7-(2-fluorophenyl)-1-(2-isopropyl-4-methylpyridin-3-yl)-4-(2-methylpiperazin-1-yl) pyrido[2,3-d]pyrimidin-2(1H)-one and trifluoroacetic acid (1.0 mL, 13.42 mmol) in DMF (1 mL) at 0° C. was added DIPEA (0.2 mL, 0.86 mmol), followed by TBTU (83 mg, 0.26 mmol). The reaction mixture was stirred at 0° C. for 10 min. The resulting mixture was added water (5 mL) and extracted with EtOAc (10 mL×2). The organic extract was washed with satd $NH_4Cl$ (15 mL) and dried over $MgSO_4$. The solution was filtered and concentrated in vacuo. The crude product was purified by silica gel chromatography (eluent: 0-60% EtOAc-EtOH (3:1)/heptane) to give (S)-6-chloro-4-(4-(2-fluoroacetyl)-2-methylpiperazin-1-yl)-7-(2-fluorophenyl)-1-(2-isopropyl-4-methylpyridin-3-yl)pyrido[2,3-d]pyrimidin-2(1H)-one (43.4 mg, 0.08 mmol, 44.7% yield, 96% purity) as a light yellow solid. $^{1}H$ NMR (400 MHz, DMSO-$d_6$) δ 8.30-8.52 (m, 2H), 7.46-7.59 (m, 1H), 7.14-7.37 (m, 4H), 5.07-5.44 (m, 2H), 4.91 (br s, 1H), 4.13-4.39 (m, 2H), 3.49-3.86 (m, 2H), 3.05-3.24 (m, 1H), 2.89 (s, 2H), 1.94 (s, 3H), 1.38 (br dd, J=13.8, 6.5 Hz, 3H), 1.07 (d, J=6.6 Hz, 3 H), 0.94 (d, J=6.6 Hz, 3H). $^{19}F$ NMR (376 MHz, DMSO-$d_6$) δ ppm −114.02 (s, 1 F), −228.53 (br d, J=248.0 Hz, 1 F). m/z (ESI, +ve) 567.0 $(M+H)^+$.

Example 3

(S)-1-(4-(6-Chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)propane-1,2-dione

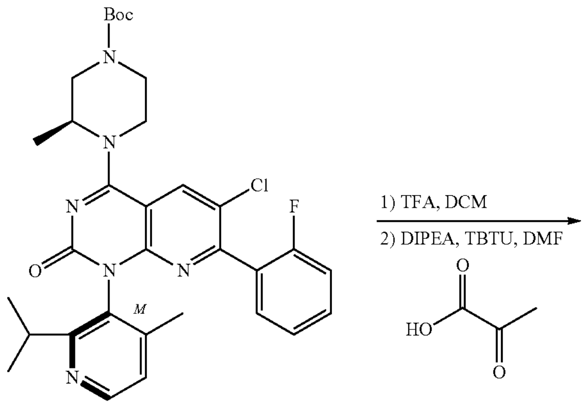

-continued

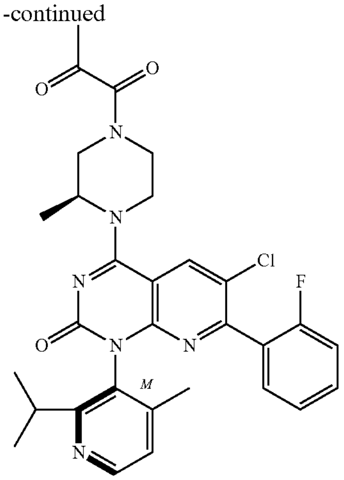

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (96 mg, 0.16 mmol) in dichloromethane (1 mL) was treated with trifluoroacetic acid (1 mL, 13.4 mmol) at rt and stirred for 10 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one in DMF (1 mL) was added a mixture of pyruvic acid (13.9 mg, 0.01 mL, 0.16 mmol, Sigma-Aldrich Corporation) and TBTU (102 mg, 0.32 mmol, Advanced ChemTech) in DMF (1 mL) at 0° C. The reaction mixture was stirred at rt for 1 h. The resulting mixture was added water (5 mL) and extracted with EtOAc (10 mL×2). The organic extract was dried over $Na_2SO_4$. The solution was filtered and concentrated in vacuo. The crude product was purified by silica gel chromatography (eluent: 0-100% EtOAc-MeOH (9:1)/heptane) to give (S)-1-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)propane-1,2-dione (42.5 mg, 0.07 mmol, 46.6% yield, 97% purity) as a light-yellow solid. $^1H$ NMR (400 MHz, DMSO-$d_6$) δ 8.44 (d, J=4.98 Hz, 1H), 8.39 (d, J=4.77 Hz, 1H), 7.46-7.57 (m, 1H), 7.24-7.35 (m, 2H), 7.14-7.23 (m, 2H), 4.81-5.12 (m, 1H), 4.11-4.42 (m, 2H), 3.39-3.85 (m, 3H), 2.69 (s, 2H), 2.43 (d, J=14.51 Hz, 3H), 1.94 (s, 3H), 1.37 (dd, J=6.84, 10.16 Hz, 3H), 1.06 (d, J=6.84 Hz, 3H), 0.94 (d, J=6.63 Hz, 3H). $^{19}F$ NMR (376 MHz, DMSO-$d_6$) δ−114.06 (s, 1F). m/z (ESI): 577.2.0 $(M+H)^+$.

Example 4

(S)-2-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)-2-oxoacetaldehyde

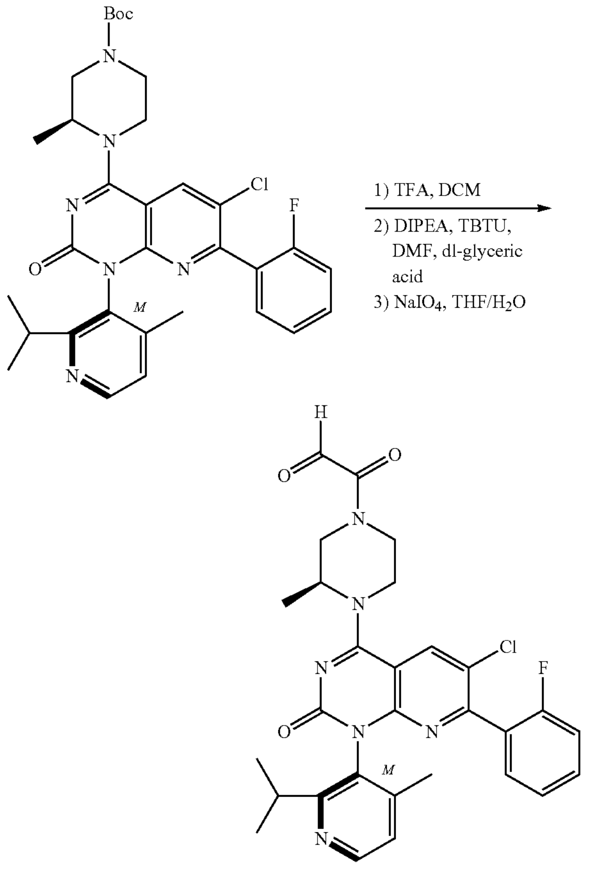

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (207 mg, 0.34 mmol) in dichloromethane (1 mL) was treated with trifluoroacetic acid (1 mL, 13.4 mmol) at rt and stirred for 10 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and dl-glyceric acid (181 mg, 0.68 mmol, TCI America) in DMF (1 mL) was added DIPEA (220 mg, 0.3 mL, 1.71 mmol), followed by TBTU (219 mg, 0.68 mmol, Advanced ChemTech) at 0° C. The reaction mixture was stirred at rt for 16 h. Additional dl-glyceric acid (181 mg, 0.68 mmol) and TBTU (219 mg, 0.68 mmol) were added and the reaction mixture was stirred additional 2 h. The resulting mixture was added 1 M HCl aqueous (5 mL) and extracted with EtOAc (10 mL×2). The organic extract was discarded. The aqueous was basified with 2 N NaOH aqueous to pH=9 and extracted with EtOAc (20 mL×2). The organic extract was dried over Na2$SO_4$. The solution was filtered and concentrated in vacuo. The crude product was purified by silica gel chromatography (eluent: 0-100% EtOAc-MeOH (9:1)/heptane) to give 6-chloro-4-((2S)-4-(2,3-dihydroxypropanoyl)-2-methylpiperazin-1-yl)-7-(2-fluorophenyl)-1-(2-isopropyl-4-methylpyridin-3-yl) pyrido[2,3-d]pyrimidin-2(1H)-one (78 mg, 0.13 mmol, 38.4% yield, 92% purity) as an yellow solid. m/z (ESI): 595.2.0 $(M+H)^+$.

To a solution of 6-chloro-4-((2S)-4-(2,3-dihydroxypropanoyl)-2-methylpiperazin-1-yl)-7-(2-fluorophenyl)-1-(2-isopropyl-4-methylpyridin-3-yl)pyrido[2,3-d]pyrimidin-2 (1H)-one (36 mg, 0.06 mmol) in THF (1.0 mL)/water (0.1 mL) was treated with sodium (meta)periodate (25.9 mg, 0.12 mmol, Sigma-Aldrich Corporation) at rt and stirred for 2.5 h. The resulting mixture was added water (5 mL) and extracted with DCM (10 mL×2). The organic extracts were combined and dried over $Na_2SO_4$. The solution was filtered and concentrated in vacuo. The crude product was purified by silica gel chromatography (eluent: 0-100% EtOAc/EtOH (3:1) in DCM) to give (S)-2-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)-2-oxoacetaldehyde (26.8 mg, 0.05 mmol, 79% yield, 99% purity) as light yellow solid. $^1H$ NMR (400 MHz, DMSO-$d_6$) δ 9.46 (d, J=12.23 Hz, 1H), 8.42-8.51 (m, 1H), 8.39 (d, J=4.77 Hz, 1H), 7.45-7.57 (m, 1H), 7.13-7.37 (m, 4H), 6.39-6.59 (m, 1H), 4.76-5.31 (m, 2H), 4.27-4.39 (m, 1H), 4.16-4.25 (m, 1H), 3.56-3.82 (m, 2H), 2.64-2.79 (m, 1H), 1.94 (s, 3H), 1.26-1.46 (m, 3H), 1.07 (d, J=6.63 Hz, 3H), 0.94 (d, J=6.63 Hz, 3H). $^{19}F$ NMR (376 MHz, DMSO-d6) δ−114.13−-113.92 (m, 1F). m/z (ESI): 581.2.0 $(M+H_2O)^+$.

Example 5

Methyl (S,E)-4-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)-4-oxobut-2-enoate

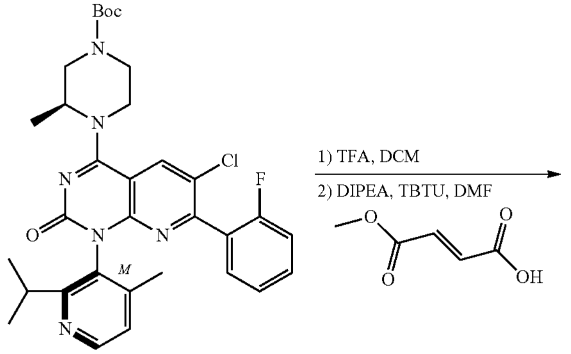

-continued

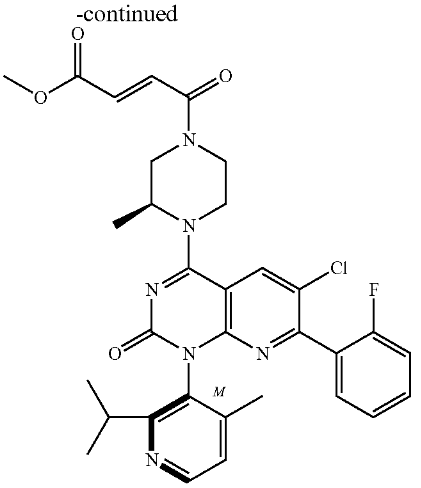

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (108 mg, 0.18 mmol) in dichloromethane (1 mL) was treated with trifluoroacetic acid (1 mL, 13.4 mmol) at rt and stirred for 10 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl) pyrido[2,3-d]pyrimidin-2(1H)-one in DMF (1 mL) was added a mixture of monomethyl fumarate (34.7 mg, 0.27 mmol, TCI America) and TBTU (114 mg, 0.36 mmol) at 0° C. The reaction mixture was stirred at 0° C. for 15 min. The reaction mixture was added water (2 mL). The resulting precipitates was collected by filtration, washed with water and dried to give methyl (S,E)-4-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)-4-oxobut-2-enoate (29.3 mg, 0.05 mmol, 26.6% yield, 94% purity) as an yellow solid. $^1H$ NMR (400 MHz, DMSO-$d_6$) δ 8.44 (d, J=17.4 Hz, 1H), 8.39 (d, J=5.0 Hz, 1H), 7.47-7.62 (m, 2H), 7.24-7.36 (m, 2H), 7.16-7.23 (m, 2H), 6.67 (dd, J=11.1, 15.5 Hz, 1H), 4.96 (ddd, J=3.1, 6.9, 14.9 Hz, 1H), 4.24-4.46 (m, 2H), 3.97-4.18 (m, 1H), 3.79-3.88 (m, 1H), 3.76 (s, 3H), 3.43-3.60 (m, 1H), 3.11-3.25 (m, 1H), 2.62-2.75 (m, 1H), 1.94 (d, J=2.90 Hz, 3H), 1.35 (br d, J=5.18 Hz, 3H), 1.07 (d, J=6.6 Hz, 3H), 0.94 (d, J=6.6 Hz, 3H). $^{19}F$ NMR (376 MHz, DMSO-$d_6$) δ−114.03 (s, 1F). m/z (ESI): 619.2 $(M+H)^+$.

Example 6

(S)-6-Chloro-7-(2-fluorophenyl)-1-(2-isopropyl-4-methylpyridin-3-yl)-4-(2-methyl-4-(2-phenoxy-acetyl)piperazin-1-yl)pyrido[2,3-d]pyrimidin-2(1H)-one

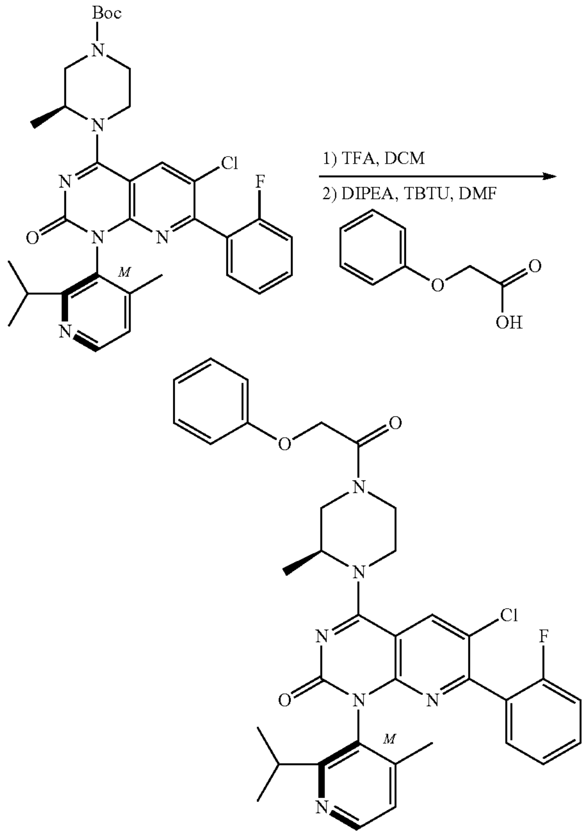

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (114 mg, 0.19 mmol) in dichloromethane (1 mL) was treated with trifluoroacetic acid (1 mL, 13.4 mmol) at rt and stirred for 10 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, nm/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl) pyrido[2,3-d]pyrimidin-2(1H)-one in DMF (1 mL) at 0° C. was added DIPEA (0.16 mL, 0.94 mmol), followed by TBTU (90 mg, 0.28 mmol). The reaction mixture was stirred at 0° C. temperature for 10 min. The resulting mixture was added water (2 mL). The resulting precipitates was collected by filtration, washed with water and dried to give a light yellow solid, which was purified by silica gel chromatography (eluent: 0-100% EtOAc/heptane) to give (S)-6-chloro-7-(2-fluorophenyl)-1-(2-isopropyl-4-methylpyridin-3-yl)-4-(2-methyl-4-(2-phenoxyacetyl)piperazin-1-yl)pyrido[2,3-d] pyrimidin-2(1H)-one (92.4 mg, 0.14 mmol, 77% yield, 99% purity) as a light yellow solid. $^1$H NMR (400 MHz, DMSO-$d_6$) δ ppm 8.44 (br d, J=15.3 Hz, 1H), 8.39 (d, J=4.8 Hz, 1H), 7.46-7.58 (m, 1H), 7.24-7.35 (m, 4H), 7.17-7.23 (m, 2H), 6.92-7.04 (m, 3H), 4.79-5.07 (m, 3H), 4.16-4.38 (m, 2H), 3.40-4.05 (m, 3 H), 3.16-3.25 (m, 1H), 2.64-2.78 (m, 1H), 1.94 (s, 3H), 1.26-1.50 (m, 3H), 1.07 (d, J=6.6 Hz, 3H), 0.95 (d, J=6.6 Hz, 3H). $^{19}$F NMR (376 MHz, DMSO-$d_6$) δ ppm −114.02 (s, 1 F). m/z (ESI, +ve) 641.1 $(M+H)^+$.

Example 7

(S)-6-Chloro-4-(4-(2-(2,6-dichlorophenoxy)acetyl)-2-methylpiperazin-1-yl)-7-(2-fluorophenyl)-1-(2-isopropyl-4-methylpyridin-3-yl)pyrido[2,3-d]pyrimidin-2(1H)-one

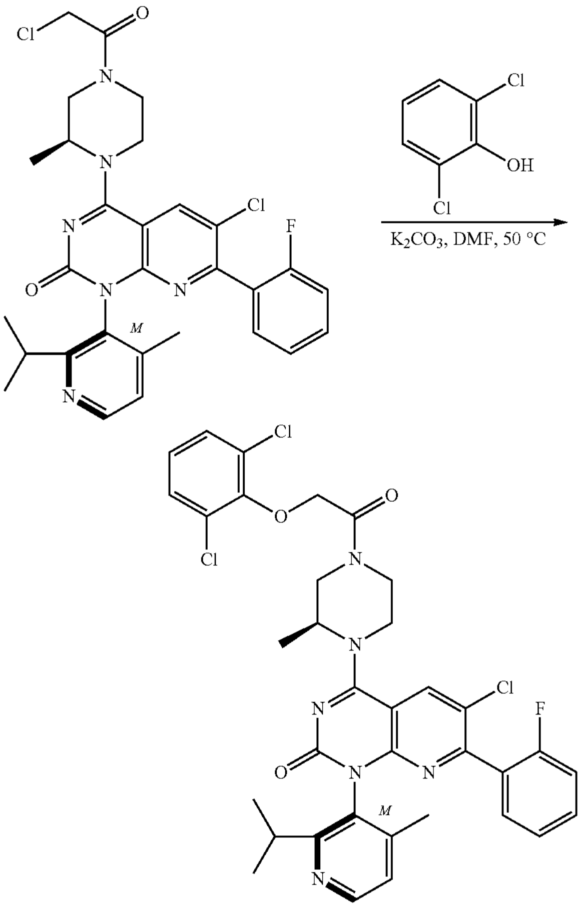

A mixture of (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (Example 1) (88 mg, 0.15 mmol), 2,6-dichlorophenol, 99% (49.2 mg, 0.30 mmol) and potassium carbonate, anhydrous (41.7 mg, 0.30 mmol) in DMF (1 mL) was stirred and heated at 50° C. for 30 min. The resulting mixture was cooled to 0° C., and added water (2 mL). The resulting precipitates was collected by filtration, washed with water and dried to give a light yellow solid which was purified by silica gel chromatography (eluent: 0-100% EtOAc/MeOH (9:1) in heptane) give (S)-6-chloro-4-(4-(2-(2,6-dichlorophenoxy) acetyl)-2-methylpiperazin-1-yl)-7-(2-fluorophenyl)-1-(2-isopropyl-4-methylpyridin-3-yl)pyrido[2,3-d]pyrimidin-2 (1H)-one (6.2 mg, 8.73 μmol, 5.79% yield, 97% purity) as a light yellow solid. $^{1}H$ NMR (400 MHz, DMSO-$d_6$) δ 8.46 (d, J=11.0 Hz, 1H), 8.39 (d, J=5.0 Hz, 1H), 7.53 (d, J=8.1 Hz, 3H), 7.17-7.34 (m, 5 H), 4.89-5.02 (m, 1H), 4.84 (s, 1H), 4.70-4.81 (m, 1H), 4.19-4.37 (m, 2H), 3.42-3.94 (m, 3H), 3.08-3.25 (m, 1H), 2.64-2.75 (m, 1H), 1.94 (s, 3H), 1.40 (br dd, J=13.7, 6.6 Hz, 3H), 1.07 (d, J=6.6 Hz, 3H), 0.95 (d, J=6.6 Hz, 3H). $^{19}F$ NMR (376 MHz, DMSO-$d_6$) δ ppm −114.04 (s, 1 F). m/z (ESI, +ve) 709.0/711.0 (1:1) $(M+H)^+$.

Example 8

(S)-6-Chloro-4-(4-(2-(2,6-difluorophenoxy)acetyl)-2-methylpiperazin-1-yl)-7-(2-fluorophenyl)-1-(2-isopropyl-4-methylpyridin-3-yl)pyrido[2,3-d]pyrimidin-2(1H)-one

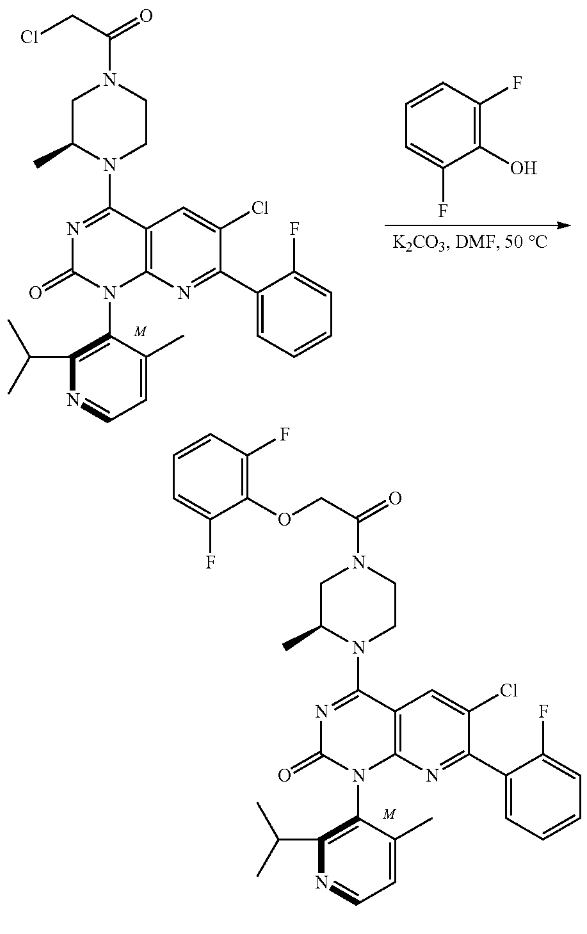

A mixture of (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (Example 1) (50 mg, 0.09 mmol), 2,6-difluorophenol (22.3 mg, 0.17 mmol) and potassium carbonate, anhydrous (23.7 mg, 0.17 mmol) in DMF (1 mL) was stirred and heated at 50° C. for 45 min. The resulting mixture was cooled to 0° C., and added water (2 mL). The resulting precipitates was collected by filtration, washed with water and dried to give (S)-6-chloro-4-(4-(2-(2,6-difluorophenoxy)acetyl)-2-methylpiperazin-1-yl)-7-(2-fluorophenyl)-1-(2-isopropyl-4-methylpyridin-3-yl)pyrido[2,3-d]pyrimidin-2(1H)-one (51.4 mg, 0.08 mmol, 89% yield, 95% purity) as a light yellow solid. $^{1}H$ NMR (400 MHz, DMSO-$d_6$) δ 8.45 (br d, J=14.5 Hz, 1 H), 8.39 (d, J=4.8 Hz, 1H), 7.44-7.58 (m, 1H), 7.24-7.34 (m, 2H), 7.06-7.23 (m, 5H), 4.97-5.17 (m, 2H), 4.92 (br s, 1H), 4.11-4.35 (m, 2H), 3.37-3.99 (m, 3H), 3.07-3.24 (m, 1H), 2.64-2.76 (m, 1H), 1.94 (s, 3H), 1.32-1.46 (m, 3H), 1.07 (d, J=6.6 Hz, 3H), 0.95 (d, J=6.6 Hz, 3H). $^{19}F$ NMR (376 MHz, DMSO-$d_6$) δ−114.03 (s, 1 F), −128.21 (d, J=17.3 Hz, 2 F). m/z (ESI, +ve) 677.8 $(M+H)^+$.

Example 9

(S)-6-chloro-7-(2-fluorophenyl)-1-(2-isopropyl-4-methylpyridin-3-yl)-4-(2-methyl-4-(2-(2,3,5,6-tetrafluorophenoxy)acetyl)piperazin-1-yl)pyrido[2,3-d]pyrimidin-2(1H)-one

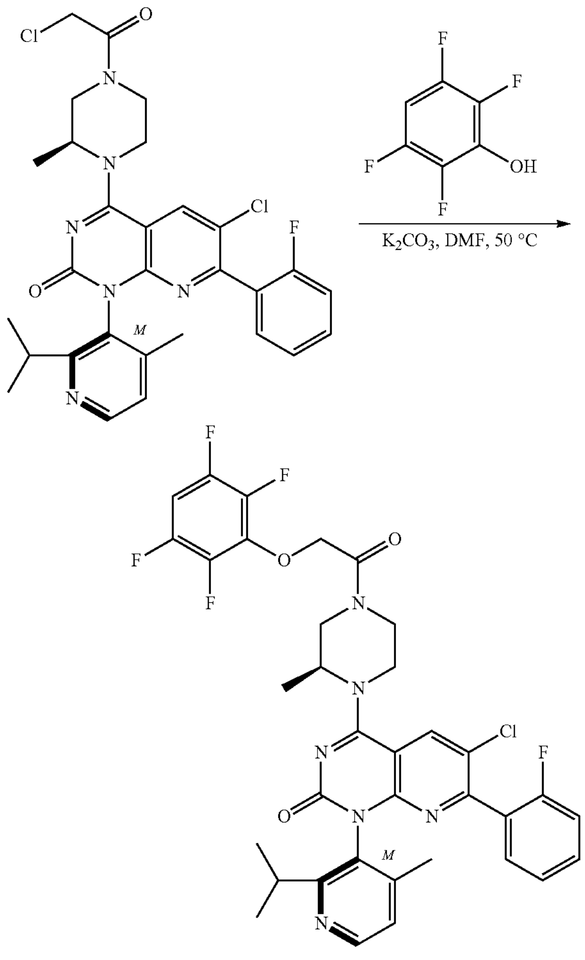

A mixture of (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (50 mg, 0.09 mmol), 2,3,5,6-tetrafluorophenol (28.5 mg, 0.17 mmol) and potassium carbonate, anhydrous (47.4 mg, 0.34 mmol) in DMF (1 mL) was stirred and heated at 50° C. for 45 min. The resulting mixture was cooled to 0° C., and added water (2 mL). The resulting precipitates was collected by filtration, washed with water and dried to give (S)-6-chloro-7-(2-fluorophenyl)-1-(2-isopropyl-4-methylpyridin-3-yl)-4-(2-methyl-4-(2-(2,3,5,6-tetrafluorophenoxy)acetyl)piperazin-1-yl)pyrido[2,3-d]pyrimidin-2(1H)-one (39.8 mg, 0.06 mmol, 65.1% yield, 95% purity) as a white solid. $^1$H NMR (400 MHz, DMSO-$d_6$) δ ppm 8.45 (br d, J=14.9 Hz, 1H), 8.39 (d, J=5.0 Hz, 1H), 7.47-7.64 (m, 2H), 7.24-7.35 (m, 2H), 7.13-7.23 (m, 2H), 5.12-5.41 (m, 2H), 4.87-4.99 (m, 1H), 4.07-4.38 (m, 2H), 3.35-3.91 (m, 3H), 3.02-3.26 (m, 1H), 2.64-2.77 (m, 1H), 1.94 (s, 3H), 1.31-1.47 (m, 3H), 1.07 (d, J=6.6 Hz, 3H), 0.95 (d, J=6.6 Hz, 3H). $^{19}$F NMR (376 MHz, DMSO-$d_6$) δ ppm −114.02 (d, J=2.6 Hz, 1 F), −140.82 (dt, J=21.0, 7.3 Hz, 2 F), −157.29 (td, J=21.2, 8.7 Hz, 2 F). m/z (ESI, +ve) 713.2 $(M+H)^+$.

Example 10

(S)-6-Chloro-7-(2-fluorophenyl)-1-(2-isopropyl-4-methylpyridin-3-yl)-4-(2-methyl-4-(2-(2,3,6-trifluorophenoxy)acetyl)piperazin-1-yl)pyrido[2,3-d]pyrimidin-2(1H)-one

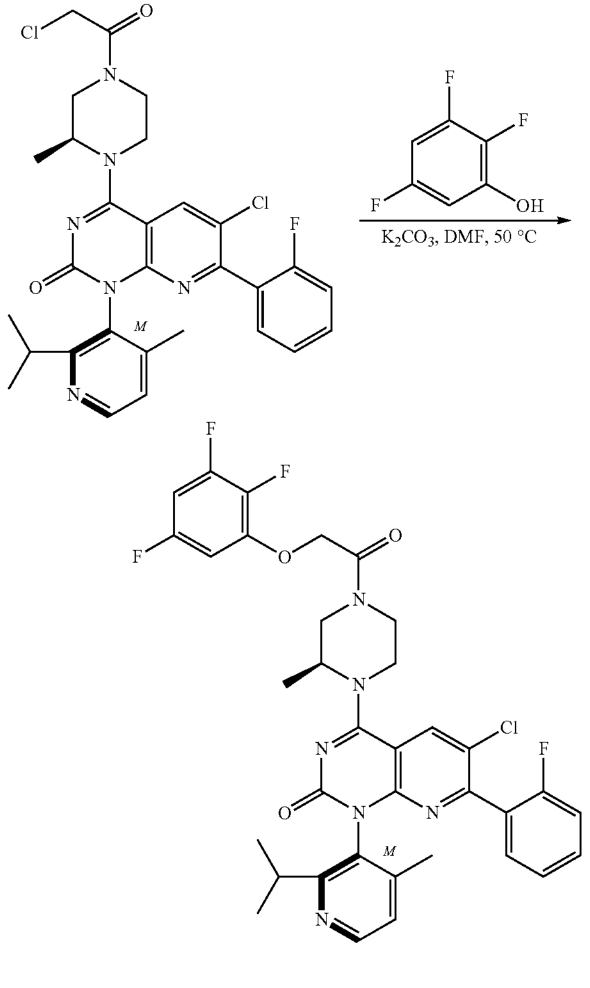

A mixture of (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (50 mg, 0.09 mmol), 2,3,6-trifluorophenol (38.1 mg, 0.26 mmol) and potassium carbonate, anhydrous (47.4 mg, 0.34 mmol) in DMF (1 mL) was stirred and heated at 50° C. for 45 min. The resulting mixture was cooled to 0° C., and added water (2 mL). The resulting precipitates was collected by filtration, washed with water and dried to give (S)-6-chloro-7-(2-fluorophenyl)-1-(2-isopropyl-4-methylpyridin-3-yl)-4-(2-methyl-4-(2-(2,3,6-trifluorophenoxy)acetyl)piperazin-1-yl)pyrido[2,3-d]pyrimidin-2(1H)-one (47.3 mg, 0.068 mmol, 79% yield, 95% purity) as a white solid. $^1$H NMR (400 MHz, DMSO-$d_6$) δ ppm 8.45 (br d, J=14.7 Hz, 1H), 8.39 (d, J=4.8 Hz, 1H), 7.47-7.57 (m, 1H), 7.24-7.36 (m, 2H), 7.12-7.23 (m, 4H), 5.03-5.34 (m, 2H), 4.92 (br d, J=1.2 Hz, 1H), 4.14-4.36 (m, 2H), 3.38-3.95 (m, 3H), 3.04-3.25 (m, 1H), 2.65-2.76 (m, 1H), 1.94 (s, 3H), 1.31-1.45 (m, 3H), 1.07 (d, J=6.6 Hz, 3H), 0.95 (d, J=6.6 Hz, 3H). $^{19}$F NMR (376 MHz, DMSO-$d_6$) δ ppm −114.03 (s, 1 F), −132.56 (ddd, J=26.9, 13.0, 5.2 Hz, 1 F), −141.58 (dd, J=21.7, 13.0 Hz, 1 F), −151.42 (br d, J=21.7 Hz, 1 F). m/z (ESI, +ve) 695.2 $(M+H)^+$.

Example 11

(S)-6-Chloro-7-(2-fluorophenyl)-1-(2-isopropyl-4-methylpyridin-3-yl)-4-(2-methyl-4-(2-(2,4,6-trifluorophenoxy)acetyl)piperazin-1-yl)pyrido[2,3-d]pyrimidin-2(1H)-one

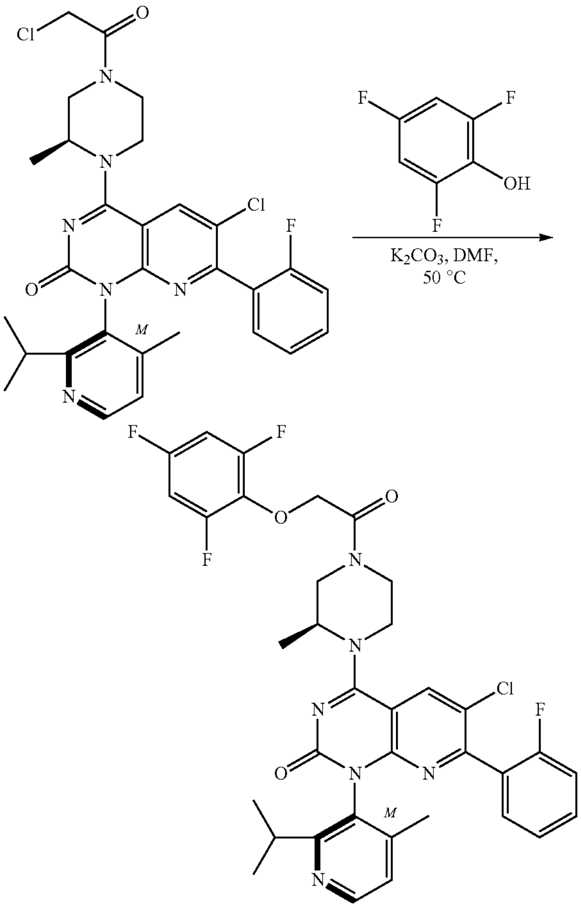

A mixture of (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (54 mg, 0.09 mmol), 2,4,6-trifluorophenol (41.1 mg, 0.28 mmol) and potassium carbonate, anhydrous (64.0 mg, 0.46 mmol) in DMF (1 mL) was stirred and heated at 50° C. for 60 min. The resulting mixture was cooled to 0° C., and added water (2 mL). The resulting precipitates was collected by filtration, washed with water and dried to give (S)-6-chloro-7-(2-fluorophenyl)-1-(2-isopropyl-4-methylpyridin-3-yl)-4-(2-methyl-4-(2-(2,4,6-trifluorophenoxy)acetyl)piperazin-1-yl) pyrido[2,3-d]pyrimidin-2(1H)-one (51.3 mg, 0.07 mmol, 80% yield, 94% purity) as a white solid. $^{1}H$ NMR (400 MHz, DMSO-$d_6$) δ 8.44 (br d, J=15.1 Hz, 1H), 8.39 (d, J=4.8 Hz, 1H), 7.45-7.56 (m, 1 H), 7.23-7.35 (m, 4H), 7.17-7.22 (m, 2H), 4.94-5.11 (m, 2H), 4.92 (br s, 1H), 4.13-4.33 (m, 2H), 3.37-3.96 (m, 3H), 3.04-3.25 (m, 1H), 2.64-2.77 (m, 1H), 1.94 (s, 3H), 1.31-1.46 (m, 3H), 1.07 (d, J=6.6 Hz, 3H), 0.94 (d, J=6.6 Hz, 3H). $^{19}F$ NMR (376 MHz, DMSO-$d_6$) 5-114.03 (s, 1 F), −115.33 (br d, J=13.0 Hz, 1 F), −125.45−−124.18 (m, 2 F). m/z (ESI, +ve) 695.2 $(M+H)^+$.

Example 12

(S)-6-Chloro-7-(2-fluorophenyl)-1-(2-isopropyl-4-methylpyridin-3-yl)-4-(2-methyl-4-(2-(2,3-difluoro-phenoxy)acetyl)piperazin-1-yl)pyrido[2,3-d]pyrimi-din-2(1H)-one

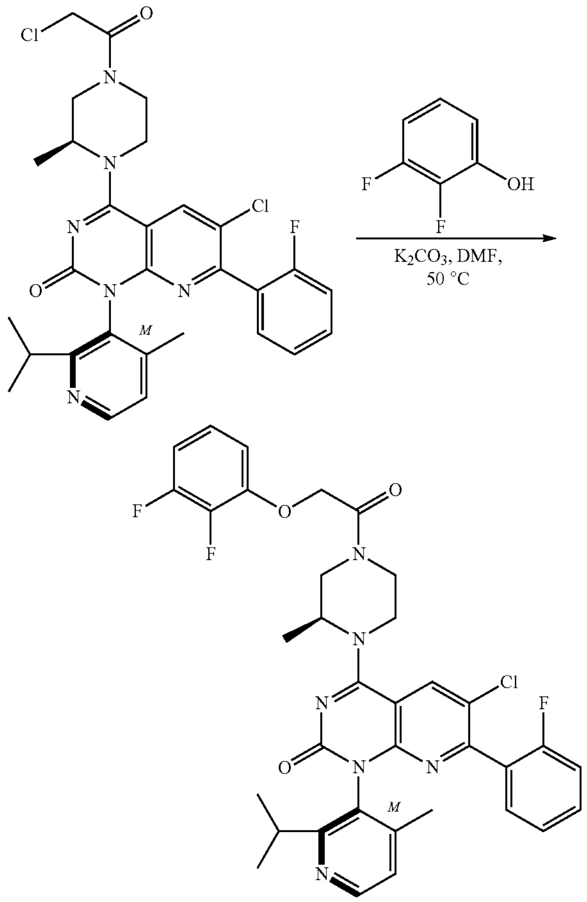

A mixture of (S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H)-one (51 mg, 0.09 mmol), 2,3-difluorophenol (34.1 mg, 0.26 mmol) and potassium carbonate, anhydrous (60.4.0 mg, 0.44 mmol) in DMF (1 mL) was stirred and heated at 50° C. for 4 h. The resulting mixture was cooled to 0° C., and added water (2 mL). The resulting precipitates was collected by filtration, washed with water and dried to give (S)-6-chloro-4-(4-(2-(2,3-difluorophenoxy)acetyl)-2-methylpiperazin-1-yl)-7-(2-fluorophenyl)-1-(2-isopropyl-4-methylpyridin-3-yl)pyrido [2,3-d]pyrimidin-2(1H)-one (38.2 mg, 0.06 mmol, 64.5% yield, 96% purity) as a white solid. $^{1}H$ NMR (400 MHz, DMSO-$d_6$) δ 8.31-8.54 (m, 2H), 7.41-7.58 (m, 1H), 7.08-7.36 (m, 5H), 6.88-7.06 (m, 2H), 5.00-5.31 (m, 2H), 4.93 (br s, 1H), 4.10-4.38 (m, 2H), 3.41-4.01 (m, 3H), 3.06-3.26 (m, 1H), 2.64-2.74 (m, 1H), 1.94 (br s, 3 H), 1.28-1.51 (m, 3H), 1.07 (br d, J=6.2 Hz, 3H), 0.95 (br d, J=6.4 Hz, 3H). $^{19}F$ NMR (376 MHz, DMSO-$d_6$) δ ppm −114.01 (br s, 1 F), −138.60 (br dd, J=20.8, 10.4 Hz, 1 F), −160.51 (br dd, J=53.8, 20.8 Hz, 1 F). m/z (ESI, +ve) 677.2 $(M+H)^+$.

Example 13

(S)-6-Chloro-4-(4-(2-diazoacetyl)-2-methylpiperazin-1-yl)-7-(2-fluorophenyl)-1-(2-isopropyl-4-methylpyridin-3-yl)pyrido[2,3-d]pyrimidin-2(1H)-one

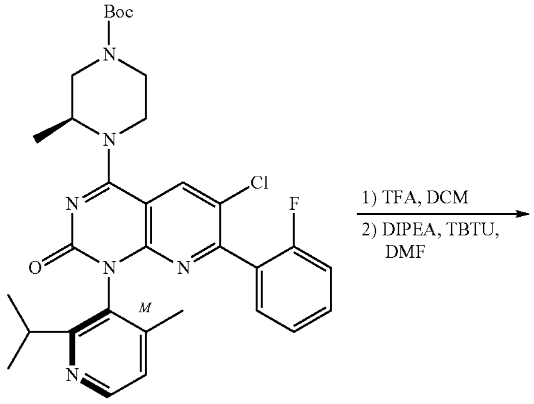

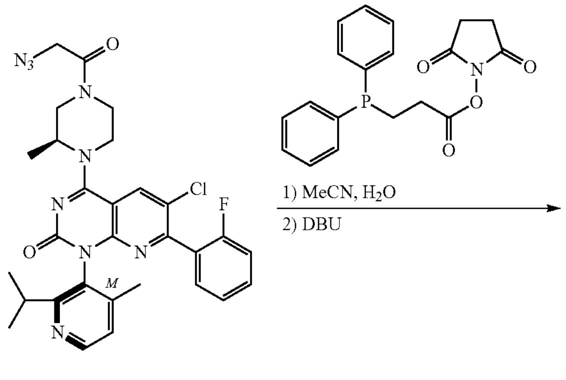

-continued

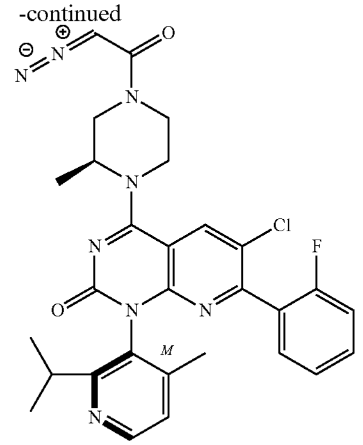

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (210 mg, 0.35 mmol) in dichloromethane (1 mL) was treated with trifluoroacetic acid (1 mL, 13.4 mmol) at rt and stirred for 30 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl) pyrido[2,3-d]pyrimidin-2(1H)-one and 2-azidoacetic acid (52.4 mg, 0.05 mL, 0.52 mmol, Sigma-Aldrich Corporation) in DMF (1 mL) was added DIPEA (224 mg, 0.30 mL, 1.73 mmol, Sigma-Aldrich Corporation), followed by TBTU (167 mg, 0.52 mmol, Advanced ChemTech) at 0° C. The reaction mixture was stirred at room temperature for 3 h. The resulting mixture was added water (5 mL) and extracted with EtOAc (10 mL×2). The organic extract dried over $MgSO_4$. The solution was filtered, concentrated in vacuo and purified by silica gel chromatography (eluent: 0-80% EtOAc/EtOH (3:1) in heptane) to give (S)-4-(4-(2-azidoacetyl)-2-methylpiperazin-1-yl)-6-chloro-7-(2-fluorophenyl)-1-(2-isopropyl-4-methylpyridin-3-yl)pyrido[2,3-d]pyrimidin-2(1H)-one (198 mg, 0.34 mmol, 97% yield, 96% purity) as a white solid. $^1H$ NMR (400 MHz, DMSO-$d_6$) δ 8.32-8.53 (m, 2H), 7.46-7.59 (m, 1H), 7.12-7.35 (m, 4H), 4.82-5.03 (m, 1H), 4.09-4.48 (m, 4H), 3.51-3.89 (m, 3H), 3.06-3.25 (m, 1H), 2.65-2.76 (m, 1H), 1.94 (s, 3H), 1.38 (br dd, J=6.74, 11.92 Hz, 3H), 1.07 (d, J=6.63 Hz, 3H), 0.95 (d, J=6.84 Hz, 3H). m/z (ESI, +ve) 590.2 $(M+H)^+$.

To a solution of (S)-4-(4-(2-azidoacetyl)-2-methylpiperazin-1-yl)-6-chloro-7-(2-fluorophenyl)-1-(2-isopropyl-4-methylpyridin-3-yl)pyrido[2,3-d]pyrimidin-2(1H)-one (94 mg, 0.16 mmol) in acetonitrile (2.0 mL)/water (0.2 mL) was treated with N-succinimidyl 3-(diphenylphosphino)propanoate (67.9 mg, 0.19 mmol, Aurum Pharmatech LLC) at 0° C. and stirred at rt for 4 h. m/z (ESI): 848.2 $(M+H)^+$ was observed. 1,8-diazabicyclo-[5.4.0]undec-7-ene (DBU, 29.1 mg, 0.03 mL, 0.19 mmol, Sigma-Aldrich Corporation) was added and the resulting mixture was stirred at rt for 1 h. The reaction mixture was diluted with sat'd NaCl (10 mL) and extracted with DCM (2×10 mL). The organic extract dried over $MgSO_4$. The solution was filtered, concentrated in vacuo and purified by silica gel chromatography (eluent: 0-10% MeOH in DCM) to give (S)-6-chloro-4-(4-(2-diazoacetyl)-2-methylpiperazin-1-yl)-7-(2-fluorophenyl)-1-(2-isopropyl-4-methylpyridin-3-yl)pyrido[2,3-d]pyrimidin-2(1H)-one (32 mg, 0.06 mmol, 34.9% yield, >95% purity) as a light yellow solid. $^1H$ NMR (400 MHz, DMSO-$d_6$) δ 8.44 (s, 1H), 8.39 (d, J=4.8 Hz, 1H), 7.55-7.47 (m, 1H), 7.34-7.24 (m, 2H), 7.23-7.16 (m, 2H), 6.13 (s, 1H), 4.98-4.84 (m, 1H), 4.27 (br d, J=13.6 Hz, 1H), 4.08 (q, J=5.2 Hz, 1H), 3.74 (br t, J=10.9 Hz, 1H), 3.49-3.35 (m, 1H), 3.26-3.08 (m, 2H), 2.76-2.67 (m, 1H), 1.94 (s, 3H), 1.36 (d, J=6.7 Hz, 3H), 1.07 (d, J=6.7 Hz, 3H), 0.94 (d, J=6.7 Hz, 3H). $^{19}F$ NMR (376 MHz, DMSO-$d_6$) δ-114.02 (s, 1F). m/z (ESI): 575.0 $(M+H)^+$.

Example 14

4-((S)-4-((R)-Aziridine-2-carbonyl)-2-methylpiperazin-1-yl)-6-chloro-7-(2-fluorophenyl)-1-(2-isopropyl-4-methylpyridin-3-yl)pyrido[2,3-d]pyrimidin-2(1H)-one

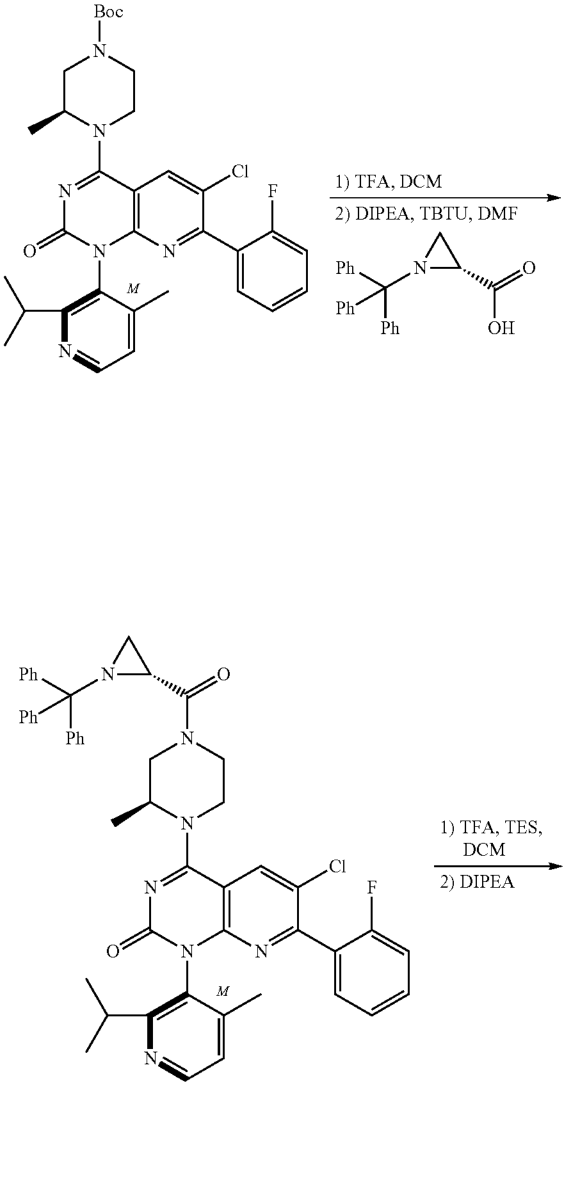

-continued

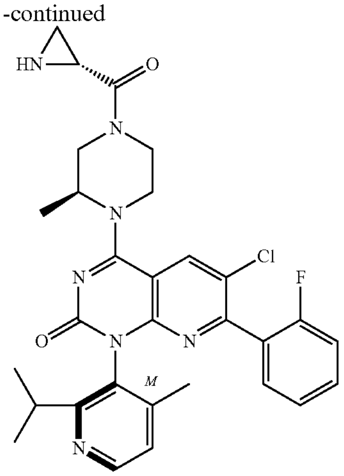

To a solution of tert-butyl (S)-4-(6-chloro-7-(2-fluorophe-nyl)-1-(2-isopropyl-4-methylpyridin-3-yl)-2-oxo-1,2-dihy-dropyrido[2,3-d]pyrimidin-4-yl)-3-methylpiperazine-1-car-boxylate (106.8 mg, 0.18 mmol) in dichloromethane (1 mL) was treated with trifluoroacetic acid (1 mL, 13.4 mmol) at rt and stirred for 15 min. The reaction mixture was concen-trated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-iso-propyl-4-methylpyridin-3-yl)-4-(2-methylpiperazin-1-yl) pyrido[2,3-d]pyrimidin-2(1H)-one and (R)-1-tritylaziridine-2-carboxylic acid (87 mg, 0.26 mmol) in DMF (1 mL) was added DIPEA (0.15 mL, 0.90 mmol, Sigma-Aldrich Corpo-ration), followed by TBTU (85 mg, 0.26 mmol, Advanced ChemTech) at 0° C. The reaction mixture was stirred at room temperature for 20 min. The resulting mixture was added water (5 mL). The resulting precipitates were collected by filtration, washed with water and dried to give to give 6-chloro-7-(2-fluorophenyl)-1-(2-isopropyl-4-methylpyri-din-3-yl)-4-((S)-2-methyl-4-((R)-1-tritylaziridine-2-carbo-nyl)piperazin-1-yl)pyrido[2,3-d]pyrimidin-2(1H)-one as a light yellow solid. m/z (ESI, +ve) 817.4 $(M+H)^+$.

To a solution of 6-chloro-7-(2-fluorophenyl)-1-(2-isopro-pyl-4-methylpyridin-3-yl)-4-((S)-2-methyl-4-((R)-1-trity-laziridine-2-carbonyl)piperazin-1-yl)pyrido[2,3-d]pyrimi-din-2(1H1)-one (144 mg, 0.18 mmol) was treated with triethylsilane (0.08 mL, 0.70 mmol) at 0° C., followed by trifluoroacetic acid (0.11 mL, 1.41 mmol) and stirred for 5 min. The reaction went to completion. The reaction mixture was diluted with EtOAc (15 mL) and washed with brine (15 mL). The organic extract was dried over $MgSO_4$. The solution was filtered, concentrated in vacuo and purified by silica gel chromatography (eluent: 0-100% EtOAc-MeOH (9:1)/heptane) to give 4-((S)-4-((R)-aziridine-2-carbonyl)-2-methylpiperazin-1-yl)-6-chloro-7-(2-fluorophenyl)-1-(2-isopropyl-4-methylpyridin-3-yl)pyrido[2,3-d]pyrimidin-2(1H)-one (15 mg, 0.03 mmol, 14.8% yield, 97% purity) as a light yellow solid. $^{1}H$ NMR (400 MHz, DMSO-$d_6$) δ 8.47 (s, 1H), 8.40 (d, J=5.0 Hz, 1H), 7.48-7.58 (m, 1H), 7.16-7.37 (m, 5H), 4.89-5.06 (m, 1H), 4.01-4.43 (m, 4H), 3.45-4.00 (m, 4H), 2.65-2.78 (m, 2H), 1.95 (s, 3H), 1.38 (br d, J=6.4 Hz, 3H), 1.08 (d, J=6.6 Hz, 3H), 0.96 (br d, J=6.6 Hz, 3H). $^{19}F$ NMR (376 MHz, DMSO-$d_6$) δ−114.03 (s, 1 F). m/z (ESI, +ve) 575.2 $(M+H)^+$.

Example 15

6-Chloro-7-(2-fluorophenyl)-1-(2-isopropyl-4-methylpyridin-3-yl)-4-((S)-2-methyl-4-((S)-oxirane-2-carbonyl)piperazin-1-yl)pyrido[2,3-d]pyrimidin-2(1H)-one

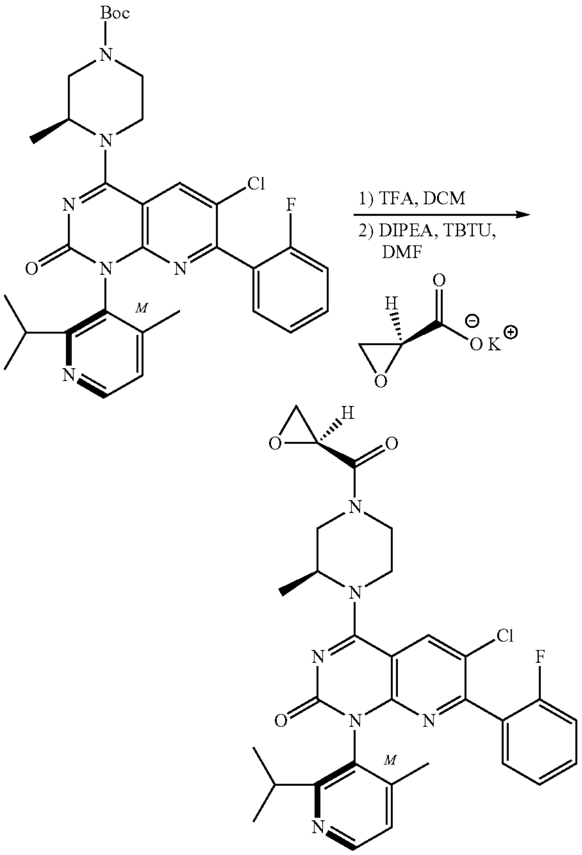

To a solution of tert-butyl (S)-4-(6-chloro-7-(2-fluorophe-nyl)-1-(2-isopropyl-4-methylpyridin-3-yl)-2-oxo-1,2-dihy-dropyrido[2,3-d]pyrimidin-4-yl)-3-methylpiperazine-1-car-boxylate (100 mg, 0.17 mmol) in dichloromethane (1 mL) was treated with trifluoroacetic acid (1 mL, 13.4 mmol) at rt and stirred for 30 min. The reaction mixture was concen-trated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-iso-propyl-4-methylpyridin-3-yl)-4-(2-methylpiperazin-1-yl) pyrido[2,3-d]pyrimidin-2(1H)-one and potassium (S)-oxi-rane-2-carboxylate (31.2 mg, 0.25 mmol) in DMF (1 mL) was added DIPEA (0.14 mL, 0.78 mmol, Sigma-Aldrich Corporation), followed by TBTU (79 mg, 0.25 mmol, Advanced ChemTech) at 0° C. The reaction mixture was stirred at room temperature for 1 h. The resulting mixture was added water (5 mL) and extracted with EtOAc (10 mL×2). The organic extract was washed with sat'd $NH_4Cl$ (15 mL) and dried over $MgSO_4$. The solution was filtered, concentrated in vacuo and purified by silica gel chromatog-raphy (eluent: 0-100% EtOAc-MeOH (9:1)/heptane) to give 6-chloro-7-(2-fluorophenyl)-1-(2-isopropyl-4-methylpyri-din-3-yl)-4-((S)-2-methyl-4-((S)-oxirane-2-carbonyl)piperazin-1-yl)pyrido[2,3-d]pyrimidin-2(1H)-one (48.8 mg, 0.09 mmol, 51.3% yield, 96% purity) as an yellow solid. $^1$H NMR (400 MHz, DMSO-$d_6$) δ 8.45 (d, J=12.0 Hz, 1H), 8.39 (d, J=4.8 Hz, 1H), 7.45-7.58 (m, 1H), 7.24-7.36 (m, 2H), 7.15-7.23 (m, 2H), 4.96 (br d, J=1.9 Hz, 1H), 4.10-4.38 (m, 3H), 3.93 (dt, J=16.6, 3.2 Hz, 1H), 3.48-3.86 (m, 2H), 3.04-3.26 (m, 1H), 2.80-3.03 (m, 2H), 2.63-2.75 (m, 1H), 1.94 (s, 3 H), 1.29-1.48 (m, 3H), 1.07 (d, J=6.6 Hz, 3H), 0.95 (d, J=6.6 Hz, 3H). $^{19}$F NMR (376 MHz, DMSO-$d_6$) δ−114.02 (s, 1 F). m/z (ESI, +ve) 577.3 $(M+H)^+$.

Example 16

6-Chloro-7-(2-fluorophenyl)-1-(2-isopropyl-4-methylpyridin-3-yl)-4-((S)-2-methyl-4-((R)-oxirane-2-carbonyl)piperazin-1-yl)pyrido[2,3-d]pyrimidin-2(1H)-one

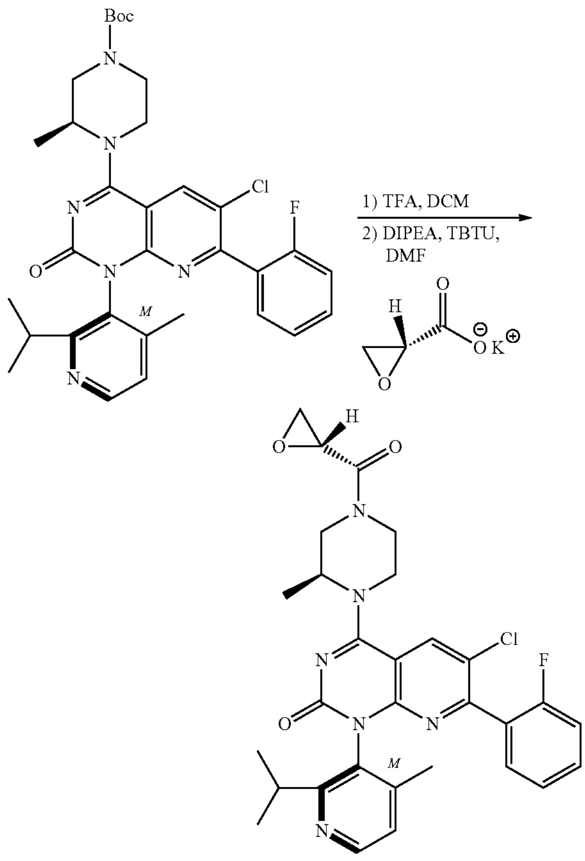

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (94 mg, 0.16 mmol) in dichloromethane (1 mL) was treated with trifluoroacetic acid (1 mL, 13.4 mmol) at rt and stirred for 30 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and potassium (R)-oxirane-2-carboxylate (29.3 mg, 0.23 mmol) in DMF (1 mL) was added DIPEA (0.14 mL, 0.78 mmol, Sigma-Aldrich Corporation), followed by TBTU (75 mg, 0.23 mmol, Advanced ChemTech) at 0° C. The reaction mixture was stirred at room temperature for 1 h. The resulting mixture was added water (5 mL) and extracted with EtOAc (10 mL×2). The organic extract was washed with sat'd $NH_4Cl$ (15 mL) and dried over $MgSO_4$. The solution was filtered, concentrated in vacuo and purified by silica gel chromatography (eluent: 0-100% EtOAc-MeOH (9:1)/heptane) to give 6-chloro-7-(2-fluorophenyl)-1-(2-isopropyl-4-methylpyridin-3-yl)-4-((S)-2-methyl-4-((R)-oxirane-2-carbonyl)piperazin-1-yl)pyrido[2,3-d]pyrimidin-2(1H)-one (31.2 mg, 0.05 mmol, 34.9% yield, 96% purity) as an yellow solid. $^1$H NMR (400 MHz, DMSO-$d_6$) δ 8.46 (d, J=6.0 Hz, 1H), 8.40 (d, J=4.8 Hz, 1H), 7.48-7.58 (m, 1H), 7.26-7.34 (m, 2H), 7.16-7.25 (m, 2H), 4.97 (br d, J=3.7 Hz, 1H), 4.15-4.37 (m, 2H), 3.83-4.13 (m, 2H), 3.45-3.78 (m, 1 H), 3.05-3.28 (m, 2H), 2.94-3.02 (m, 1H), 2.79-2.88 (m, 1H), 2.63-2.76 (m, 1H), 1.95 (s, 3H), 1.38 (dd, J=9.1, 6.8 Hz, 3H), 1.08 (d, J=6.8 Hz, 3H), 0.96 (d, J=6.8 Hz, 3H). $^{19}$F NMR (376 MHz, DMSO-$d_6$) δ−114.02 (d, J=3.5 Hz, 1 F). m/z (ESI, +ve) 577.3 $(M+H)^+$.

Example 17

6-Chloro-7-(2-fluorophenyl)-1-(2-isopropyl-4-methylpyridin-3-yl)-4-((S)-2-methyl-4-((2R,3S)-3-methyloxirane-2-carbonyl)piperazin-1-yl)pyrido[2,3-d]pyrimidin-2(1H)-one and 6-chloro-7-(2-fluorophenyl)-1-(2-isopropyl-4-methylpyridin-3-yl)-4-((S)-2-methyl-4-((2S,3R)-3-methyloxirane-2-carbonyl)piperazin-1-yl)pyrido[2,3-d]pyrimidin-2(1H)-one

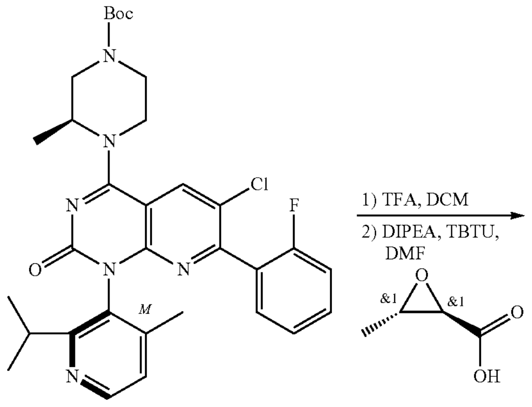

-continued

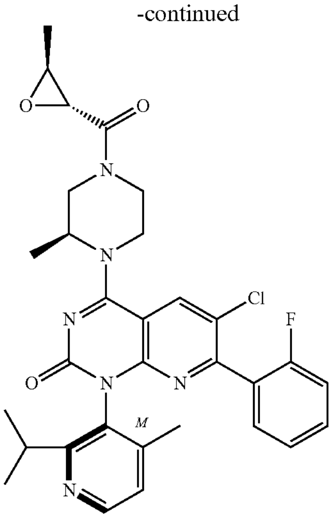

+

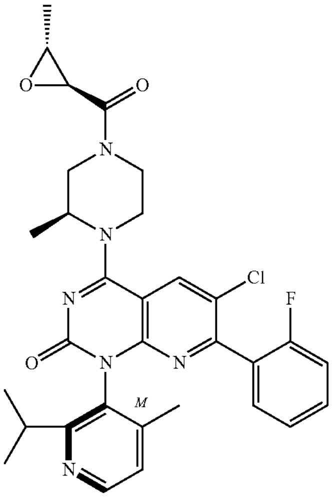

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (100 mg, 0.17 mmol) in dichloromethane (1 mL) was treated with trifluoroacetic acid (1 mL, 13.4 mmol) at rt and stirred for 30 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and Rac-(2R,3S)-3-methyl-2-oxiranecarboxylic acid, trans (33.6 mg, 0.33 mmol, Enamine) in DMF (1 mL) was added DIPEA (0.14 mL, 0.78 mmol, Sigma-Aldrich Corporation), followed by TBTU (106 mg, 0.33 mmol, Advanced ChemTech) at 0° C. and stirred at 0° C. for 30 min. The resulting mixture was added water (5 mL) and extracted with EtOAc (10 mL×2). The organic extract was washed with sat'd $NH_4Cl$ (15 mL) and dried over $MgSO_4$. The solution was filtered, concentrated in vacuo and purified by silica gel chromatography (eluent: 0-100% EtOAc-MeOH (7:3)/heptane) to give a mixture of 6-chloro-7-(2-fluorophenyl)-1-(2-isopropyl-4-methylpyridin-3-yl)-4-((S)-2-methyl-4-((2R,3S)-3-methyloxirane-2-carbonyl)piperazin-1-yl)pyrido[2,3-d]pyrimidin-2(1H)-one and 6-chloro-7-(2-fluorophenyl)-1-(2-isopropyl-4-methylpyridin-3-yl)-4-((S)-2-methyl-4-((2S,3R)-3-methyloxirane-2-carbonyl)piperazin-1-yl)pyrido[2,3-d]pyrimidin-2(1H)-one (1:1 ratio, 78.5 mg, 0.13 mmol, 81% yield, 98% purity) as a light yellow solid. $^1H$ NMR (400 MHz, DMSO-$d_6$) δ 8.43-8.48 (m, 1H), 8.40 (d, J=5.02 Hz, 1H), 7.48-7.58 (m, 1H), 7.25-7.36 (m, 2H), 7.18-7.24 (m, 2H), 4.96 (br s, 1H), 3.97-4.40 (m, 3H), 3.66-3.90 (m, 3H), 3.00-3.26 (m, 2H), 2.64-2.74 (m, 1H), 1.95 (s, 3H), 1.29-1.49 (m, 6H), 1.08 (d, J=6.69 Hz, 3H), 0.95 (d, J=6.69 Hz, 3H). $^{19}F$ NMR (376 MHz, DMSO-$d_6$) δ−114.03 (s, 1F). m/z (ESI, +ve) 591.2 $(M+H)^+$.

Example 18

Ethyl (2S,3S)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylate

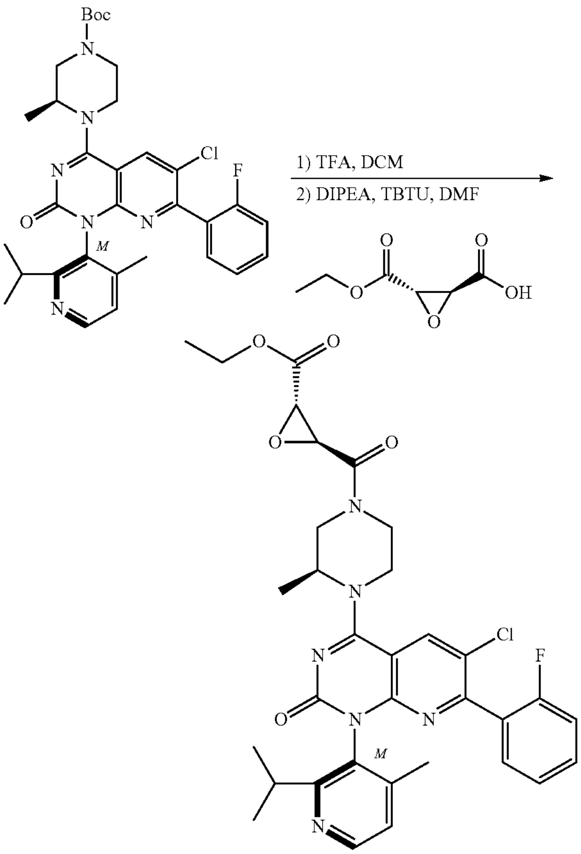

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (95 mg, 0.16 mmol) in dichloromethane (1 mL) was treated with trifluoroacetic acid (1 mL, 13.4 mmol) at rt and stirred for 15 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of (S)-6-chloro-7-(2-fluorophenyl)-1-(2-isopropyl-4-methylpyridin-3-yl)-4-(2-methylpiperazin-1-yl)

pyrido[2,3-d]pyrimidin-2(1H)-one and (2S,3S)-3-(ethoxy-carbonyl)oxirane-2-carboxylic acid (50.1 mg, 0.31 mmol, Carbosynth Ltd.) in DMF (1 mL) was added DIPEA (0.14 mL, 0.78 mmol, Sigma-Aldrich Corporation), followed by TBTU (100 mg, 0.31 mmol, Advanced ChemTech) at 0° C. The reaction mixture was stirred at room temperature for 1 h. The resulting mixture was added water (5 mL) and extracted with EtOAc (10 mL×2). The organic extract was dried over $MgSO_4$. The solution was filtered, concentrated in vacuo and purified by silica gel chromatography (eluent: 0-100% EtOAc-MeOH (9:1)/heptane) to give ethyl (2S,3S)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylate (12.2 mg, 0.02 mmol, 12% yield, 96% purity) as a light yellow solid. $^1H$ NMR (400 MHz, DMSO-$d_6$) δ 8.45 (d, J=13.1 Hz, 1H), 8.39 (d, J=5.0 Hz, 1H), 7.45-7.57 (m, 1H), 7.16-7.35 (m, 4H), 4.95 (br d, J=5.6 Hz, 1H), 4.04-4.37 (m, 6H), 3.49-3.88 (m, 3H), 3.06-3.27 (m, 1H), 2.65-2.75 (m, 1H), 1.94 (d, J=2.5 Hz, 3H), 1.33-1.46 (m, 3H), 1.21-1.30 (m, 3H), 1.07 (d, J=6.4 Hz, 3H), 0.95 (d, J=6.6 Hz, 3H). $^{19}F$ NMR (376 MHz, DMSO-$d_6$) δ−114.03 (d, J=1.73 Hz, 1F). m/z (ESI, +ve) 649.2 $(M+H)^+$.

Example 19 and 20

Ethyl (2R,3R)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylate (19) and (2R,3R)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylic Acid (20)

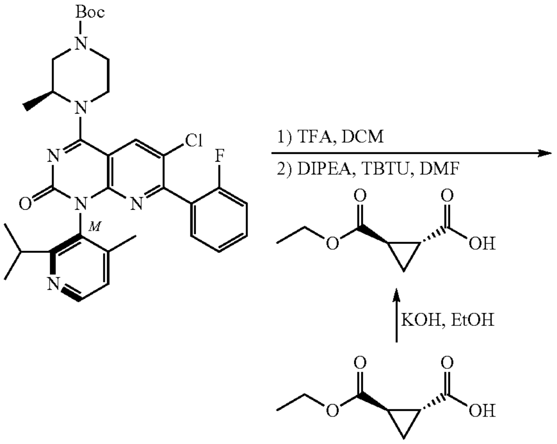

-continued

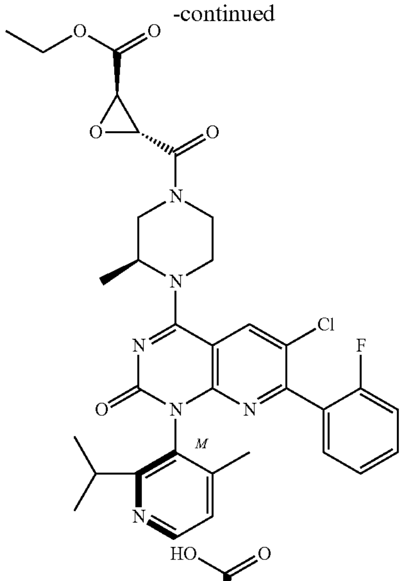

+

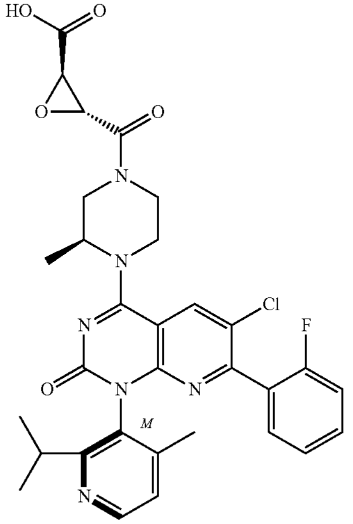

To an ice cooled solution of (2R,3R)-diethyl 2,3-epoxysuccinate (250 mg, 1.33 mmol, Sigma-Aldrich Corporation) in ethanol (3 mL) was added dropwise a solution of potassium hydroxide (89 mg, 1.594 mmol, VWR International, LLC) in ethanol (2.0 mL) over 2 minutes. After this addition the reaction mixture was allowed to stir at 0° C. for 3 h. The resulting reaction mixture became a gel-like mixture. The cooling bath was then removed and the reaction mixture was stirred for further 16 h at room temperature. Afterwards the ethanol was removed in vacuo leaving an off white solid. This salt was then taken up with 10 mL of water and washed three times with dichloride methane. The aqueous phase was acidified by addition of 2 M HCl to pH 3 and extracted with ethyl acetate (10 mL×3). The combined organic phase was dried over $MgSO_4$, filtered, and concentrated in vacuo. After drying the pure product (2R,3R)-3-(ethoxycarbonyl)oxirane-2-carboxylic acid (170 mg, 1.06 mmol, 80% yield) was obtained as a colorless oil. $^1H$ NMR (400 MHz, CDCl3) δ 8.41-9.03 (brs, 1H), 4.29 (ttd, J=3.6, 7.1, 10.7 Hz, 2H), 3.72-3.73 (m, 1H), 3.70-3.72 (m, 1H), 1.33 (t, J=7.2 Hz, 3H). [Ref: ACS Chemical Biology, 5(3), 279-285; 2010]

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (105 mg, 0.17 mmol) in dichloromethane (1 mL) was treated with trifluoroacetic acid (1 mL, 13.4 mmol) at rt and stirred for 15 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of TBTU (111 mg, 0.35 mmol, Advanced ChemTech) and (2R,3R)-3-(ethoxycarbonyl)oxirane-2-carboxylic acid (55.4 mg, 0.35 mmol) in DMF (1 mL) was added DIPEA (0.09 mL, 0.52 mmol, Sigma-Aldrich Corporation) at 0° C. and stirred for 5 min. The resulting mixture was added to a mixture of the above (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and DIPEA (0.09 mL, 0.52 mmol) in DMF (1 mL) at 0° C. and stirred at room temperature for 16 h. The resulting mixture was added water (5 mL) and extracted with EtOAc (10 mL×2). The organic extract was dried over $MgSO_4$. The solution was filtered, concentrated in vacuo and purified by silica gel chromatography (eluent: 0-100% EtOAc-MeOH (9:1)/heptane) to give ethyl (2R,3R)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylate (39.5 mg, 0.06 mmol, 35.2% yield, 90% purity) as a white solid. $^1H$ NMR (400 MHz, DMSO-$d_6$) δ 8.45 (d, J=8.1 Hz, 1H), 8.39 (d, J=5.0 Hz, 1H), 7.46-7.56 (m, 1H), 7.18-7.35 (m, 4H), 4.95 (br d, J=2.5 Hz, 1H), 4.13-4.37 (m, 6H), 3.42-3.80 (m, 3H), 3.05-3.21 (m, 1H), 2.63-2.78 (m, 1H), 1.94 (d, J=1.9 Hz, 3H), 1.37 (dd, J=6.8, 9.7 Hz, 3H), 1.26 (dt, J=3.5, 7.1 Hz, 3H), 1.07 (d, J=6.6 Hz, 3H), 0.95 (d, J=6.6 Hz, 3H). $^{19}F$ NMR (377 MHz, DMSO-$d_6$) δ−114.03 (s, 1F). m/z (ESI, +ve) 649.0 $(M+H)^+$.

The aqueous layer was acidified with 2N HCl to pH=1-2 and extracted with DCM (10 mL×2). The organic extract was dried over $MgSO_4$. The solution was filtered, concentrated in vacuo and purified by silica gel chromatography (eluent: 0-15% MeOH (with 2% AcOH)/DCM) to give (2R,3R)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylic acid (6.5 mg, 10.5 μmol, 6% yield, 93% purity) as a white solid. $^1H$ NMR (400 MHz, DMSO-$d_6$) δ 11.92 (s, 1H), 8.45 (d, J=3.94 Hz, 1H), 8.39 (d, J=4.98 Hz, 1H), 7.47-7.54 (m, 1H), 7.24-7.34 (m, 2H), 7.16-7.23 (m, 2H), 4.92-5.00 (m, 1H), 4.27-4.35 (m, 2H), 4.14-4.20 (m, 1H), 3.86-4.08 (m, 3H), 3.69-3.78 (m, 1H), 3.51 (br s, 1H), 2.69-2.77 (m, 1H), 1.91 (s, 3H), 1.37 (br dd, J=6.74, 14.82 Hz, 3H), 1.07 (d, J=6.63 Hz, 3H), 0.95 (d, J=6.63 Hz, 3H). $^{19}F$ NMR (377 MHz, DMSO-$d_6$) δ−114.03 (s, 1F). m/z (ESI, +ve) 621.2 $(M+H)^+$.

Example 21

6-Chloro-7-(2-fluorophenyl)-1-(2-isopropyl-4-methylpyridin-3-yl)-4-((S)-2-methyl-4-((2R,3S)-3-(piperidin-1-ylmethyl)oxirane-2-carbonyl)piperazin-1-yl)pyrido[2,3-d]pyrimidin-2(1H)-one

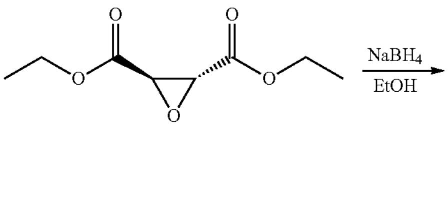

-continued

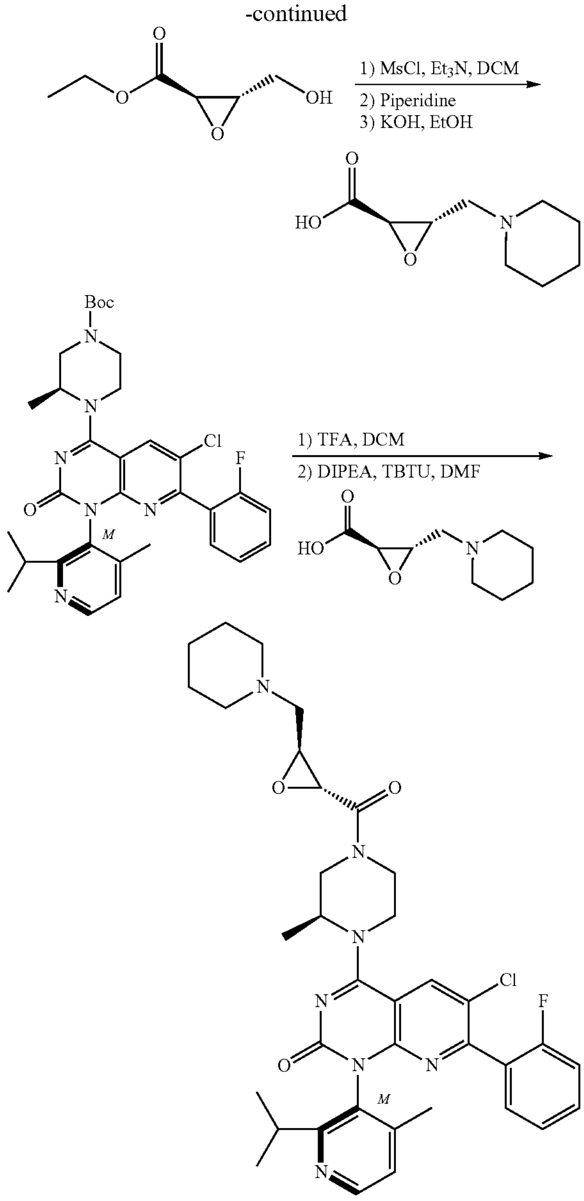

To an ice cooled solution of (2R,3R)-diethyl 2,3-epoxysuccinate (900 mg, 4.78 mmol, Sigma-Aldrich Corporation) in ethanol (3 mL) was added sodium borohydride (145 mg, 3.83 mmol, Sigma-Aldrich Corporation). After this addition the reaction mixture was allowed to stir in ice bath for 2 h. The reaction mixture was quenched with water slowly (1.0 mL) and then acidified by addition of 2 M HCl aqueous to pH 6-7. Afterwards the ethanol was removed under reduced pressure leaving an off white solid. This salt was then taken up with 15 mL of water and washed three times with dichloride methane. The aqueous phase was acidified by addition of concentrated hydrochloric acid to pH 3 and extracted four times with DCM. The combined organic phase was dried over magnesium sulphate and concentrated under reduced pressure to give ethyl (2R,3S)-3-(hydroxymethyl)oxirane-2-carboxylate (413.8 mg, 2.83 mmol, 59.2% yield) as a yellow oil. $^1H$ NMR (400 MHz, $CDCl_3$) δ 4.18-4.33 (m, 2H), 4.01 (ddd, J=2.18, 5.08, 13.06 Hz, 1H), 3.72-3.81 (m, 1H), 3.54 (d, J=2.07 Hz, 1H), 3.39

(td, J=2.10, 3.27 Hz, 1H), 1.64 (dd, J=5.18, 8.09 Hz, 1H), 1.31 (t, J=7.15 Hz, 3H). (Ref: *J. Org. Chem.* 2005, 70, 5643-5654.)

To an ice cooled solution of ethyl (2R,3S)-3-(hydroxymethyl)oxirane-2-carboxylate (410 mg, 2.81 mmol) in dichloromethane (12 mL) was added triethylamine (0.59 mL, 4.21 mmol, Sigma-Aldrich Corporation). After 5 min, the reaction mixture was treated with methanesulfonyl chloride (0.33 mL, 4.21 mmol, Sigma-Aldrich Corporation) and stirred for 10 min at 0° C. and for 2 h at room temperature. Then the solvent was evaporated. The resulting yellow paste was dissolved in N, N-dimethylformamide (12.00 mL), and potassium iodide (23.3 mg, 0.14 mmol, Fisher Scientific UK) was added. The yellow solution was cooled to 0° C. before the dropwise addition of piperidine (0.83 mL, 8.42 mmol, Spectrum Chemicals & Laboratory Products). The resulting suspension solution was slowly warmed to room temperature and stirred for 24 h. The resulting reaction mixture was diluted with saturated aqueous $NaHCO_3$ (10 mL) and extracted with DCM (20 mL×2). The organic extract was dried over $MgSO_4$. The solution was filtered, concentrated in vacuo and purified by silica gel chromatography (eluent: 0-4% MeOH/DCM) to give ethyl (2R,3S)-3-(piperidin-1-ylmethyl)oxirane-2-carboxylate (90.2 mg, 0.423 mmol, 15.07% yield) as a brown oil. $^1H$ NMR (400 MHz, $CDCl_3$) δ 4.19-4.33 (m, 2H), 3.35-3.44 (m, 1H), 3.24 (d, J=1.87 Hz, 1H), 2.82 (br s, 1H), 2.43-2.68 (m, 4H), 2.38 (dd, J=6.63, 13.68 Hz, 1H), 1.64 (br s, 4H), 1.46 (br s, 2H), 1.30 (t, J=7.15 Hz, 3H). m/z (ESI): 214.2 $(M+H)^+$. (Ref: *J. Med. Chem.* 2010, 53, 2038-2050.)

To an ice cooled solution of ethyl (2R,3S)-3-(piperidin-1-ylmethyl)oxirane-2-carboxylate (90 mg, 0.422 mmol) in ethanol (1.5 mL) was added drop wise a solution of potassium hydroxide (28.4 mg, 0.506 mmol, VWR International, LLC) in ethanol (1.5 mL) over 2 minutes. After this addition the reaction mixture was allowed to stir in ice for 2 h and at room temperature for 17 h. The resulting reaction mixture became a brown solution. Afterwards the ethanol was removed under reduced pressure leaving a brown oil which was used in the next step without purification. m/z (ESI): 186.2 $(M+H)^+$.

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (93 mg, 0.15 mmol) in dichloromethane (1 mL) was treated with trifluoroacetic acid (1 mL, 13.4 mmol) at rt and stirred for 15 min. The reaction mixture was concentrated in vacuo to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of TBTU (98 mg, 0.31 mmol, Advanced ChemTech) and (2R,3S)-3-(piperidin-1-ylmethyl)oxirane-2-carboxylic acid (78 mg, 0.42 mmol) in N, N-dimethylformamide (1 mL) at 0° C. was added DIPEA (0.13 mL, 0.77 mmol, Sigma-Aldrich Corporation) and stirred for 5 min. The above mixture was added to a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and DIPEA (0.13 mL, 0.77 mmol) in N, N-dimethylformamide (1 mL) at 0° C. The reaction mixture was stirred at room temperature for 3 h. The resulting mixture was added water (5 mL) and extracted with EtOAc (20 mL×2). The organic extract was dried over $MgSO_4$. The solution was filtered, concentrated in vacuo and purified by silica gel chromatography (eluent: 0-10% MeOH/DCM) to give 6-chloro-7-(2-fluorophenyl)-1-(2-isopropyl-4-methylpyridin-3-yl)-4-((S)-2-methyl-4-((2R,3S)-3-(piperidin-1-ylmethyl)oxirane-2-carbonyl)piperazin-1-yl)pyrido[2,3-d]pyrimidin-2(1H)-one (56.3 mg, 0.08 mmol, 54.5% yield, >99% purity) as a light-yellow solid. $^1H$ NMR (400 MHz, DMSO-$d_6$) δ 8.45 (d, J=7.11 Hz, 1H), 8.39 (d, J=4.81 Hz, 1H), 7.47-7.55 (m, 1H), 7.24-7.34 (m, 2H), 7.17-7.24 (m, 2H), 4.90-5.02 (m, 1H), 3.96-4.36 (m, 3H), 3.36-3.94 (m, 4H), 3.02-3.24 (m, 2H), 2.68-2.80 (m, 2H), 2.36-2.46 (m, 3H), 2.23-2.32 (m, 1H), 1.94 (s, 3H), 1.52 (br d, J=2.30 Hz, 4H), 1.30-1.42 (m, 5H), 1.07 (d, J=6.69 Hz, 3H), 0.95 (d, J=6.69 Hz, 3H). $^{19}F$ NMR (376 MHz, DMSO-$d_6$) δ-114.02 (d, J=4.34 Hz, 1F). m/z (ESI, +ve) 674.2 $(M+H)^+$.

Example 22

6-Chloro-7-(2-fluorophenyl)-4-((S)-4-((2R,3S)-3-(hydroxymethyl)oxirane-2-carbonyl)-2-methylpiperazin-1-yl)-1-(2-isopropyl-4-methylpyridin-3-yl)pyrido[2,3-d]pyrimidin-2(1H)-one

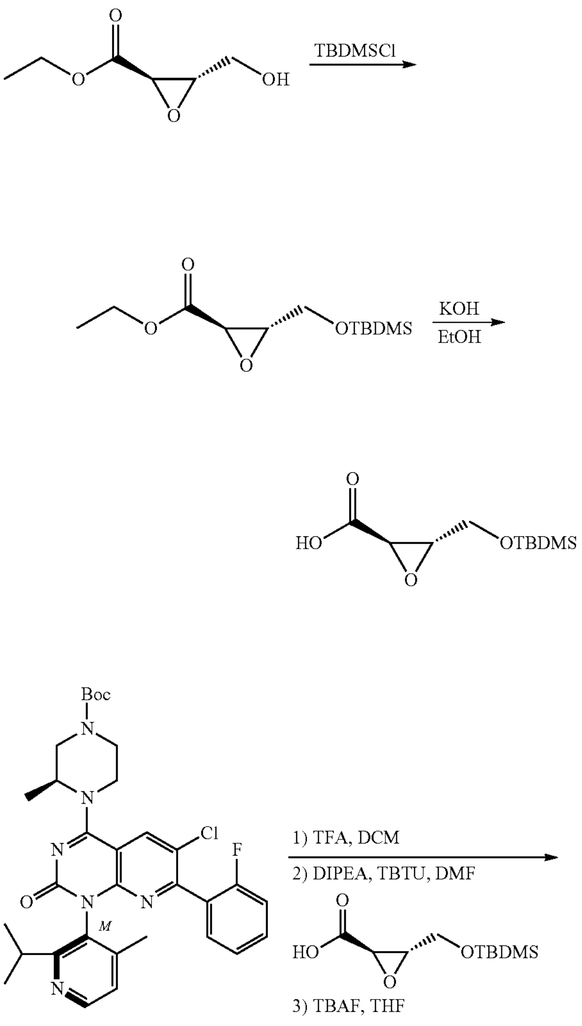

-continued

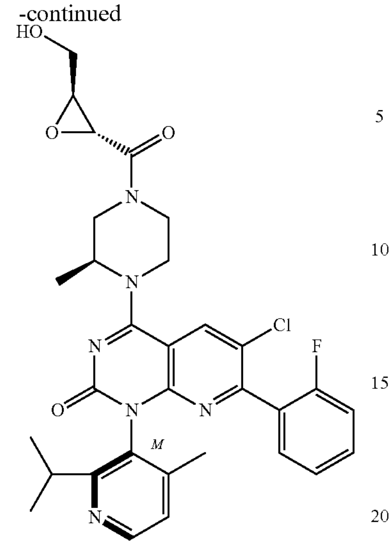

To a mixture of ethyl (2R,3S)-3-(hydroxymethyl)oxirane-2-carboxylate (300 mg, 2.05 mmol) and imidazole (280 mg, 4.11 mmol, Sigma-Aldrich Corporation) in tetrahydrofuran (4 mL) was added (1,1-dimethylethyl)dimethylsilyl chloride (309 mg, 2.053 mmol, Combi-Blocks Inc.). After this addition the reaction mixture was allowed to stir at room temperature for 1 h. The reaction mixture was quenched with water (5 mL) and extracted with DCM (10 mL×4). The combined organic phase was dried over $MgSO_4$. The solution was filtered, concentrated in vacuo and purified by silica gel chromatography (eluent: 0-10% EtOAc/heptanes) to give ethyl (2R,3S)-3-(((tert-butyldimethylsilyl)oxy)methyl) oxirane-2-carboxylate (415.1 mg, 1.59 mmol, 78% yield) as a colorless oil. $^1$H NMR (400 MHz, $CDCl_3$) δ 4.09-4.25 (m, 2H), 3.80-3.89 (m, 1H), 3.68-3.75 (m, 1H), 3.36 (d, J=1.87 Hz, 1H), 3.25 (td, J=2.33, 3.42 Hz, 1H), 1.24 (t, J=7.15 Hz, 3H), 0.83 (s, 9H), 0.00 (d, J=3.32 Hz, 6H). m/z (ESI): 261.2 $(M+H)^+$.

To an ice cooled solution of ethyl (2R,3S)-3-(((tert-butyldimethylsilyl)oxy)methyl)oxirane-2-carboxylate (410 mg, 1.57 mmol) in ethanol (1.5 mL) was added dropwise a solution of potassium hydroxide (106 mg, 1.89 mmol, VWR International, LLC) in ethanol (1.5 mL) over 2 minutes. After this addition the reaction mixture was allowed to stir in ice bath for 5 min and at room temperature for 24 h. The resulting reaction mixture became a brown solution. Afterwards the ethanol was removed under reduced pressure leaving potassium (2R,3S)-3-(((tert-butyldimethylsilyl)oxy) methyl)oxirane-2-carboxylate as a light yellow solid, which was used in the next step without purification. m/z (ESI): 186.2 $(M+H)^+$.

To a solution of tert-butyl (S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (103 mg, 0.17 mmol) in dichloromethane (1 mL) was treated with trifluoroacetic acid (1.0 mL, 13.4 mmol) at rt and stirred for 15 min. The reaction went to completion and concentrated to afford (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one, m/z (ESI, +ve) 507.2 $(M+H)^+$.

To a mixture of TBTU (109 mg, 0.34 mmol, Advanced ChemTech) and potassium (2R,3S)-3-(((tert-butyldimethylsilyl)oxy)methyl)oxirane-2-carboxylate (138 mg, 0.51 mmol) in N, N-dimethylformamide (1 mL) at 0° C. was added DIPEA (0.15 mL, 0.85 mmol) and stirred for 5 min. The above mixture was added to a mixture of (S)-6-chloro-7-(2-fluorophenyl)-1-(2-isopropyl-4-methylpyridin-3-yl)-4-(2-methylpiperazin-1-yl)pyrido[2,3-d]pyrimidin-2(1H)-one and DIPEA (0.15 mL, 0.85 mmol) in N, N-dimethylformamide (1 mL) at 0° C. The reaction mixture was stirred at room temperature for 30 min. The resulting mixture was added water (5 mL) and extracted with EtOAc (20 mL×2). The organic extract dried over $MgSO_4$. The solution was filtered, concentrated in vacuo and purified by silica gel chromatography (eluent: 0-10% MeOH/DCM) to give 4-((S)-4-((2R,3S)-3-(((tert-butyldimethylsilyl)oxy)methyl) oxirane-2-carbonyl)-2-methylpiperazin-1-yl)-6-chloro-7-(2-fluorophenyl)-1-(2-isopropyl-4-methylpyridin-3-yl)pyrido [2,3-d]pyrimidin-2(1H)-one (101 mg, 0.14 mmol, 83% yield) as a light-yellow solid. m/z (ESI): 721.2 $(M+H)^+$.

4-((S)-4-((2R,3S)-3-(((tert-butyldimethylsilyl)oxy) methyl)oxirane-2-carbonyl)-2-methylpiperazin-1-yl)-6-chloro-7-(2-fluorophenyl)-1-(2-isopropyl-4-methylpyridin-3-yl)pyrido[2,3-d]pyrimidin-2(1H)-one (101 mg, 0.14 mmol) was dissolved in THE (1.0 mL) and treated with TBAF (tetrabutylammonium fluoride solution, 1.0 M in tetrahydrofuran, 0.34 mL, 0.34 mmol, Sigma-Aldrich Corporation) at 0° C. and stirred at room temperature for 5 h. The reaction mixture was diluted with water (10 mL) and extracted with DCM (3×10 mL). The organic extract was washed with dried over $MgSO_4$. The solution was filtered, concentrated in vacuo and purified by silica gel chromatography (eluent: 0-10% MeOH/DCM) to give 6-chloro-7-(2-fluorophenyl)-4-((S)-4-((2R,3S)-3-(hydroxymethyl)oxirane-2-carbonyl)-2-methylpiperazin-1-yl)-1-(2-isopropyl-4-methylpyridin-3-yl)pyrido[2,3-d]pyrimidin-2(1H)-one (8.1 mg, 0.01 mmol, 7.9% yield, 99% purity) as a light-yellow solid. $^1$H NMR (400 MHz, DMSO-$d_6$) δ 8.45 (d, J=6.06 Hz, 1H), 8.39 (d, J=5.02 Hz, 1H), 7.47-7.57 (m, 1H), 7.24-7.35 (m, 2H), 7.17-7.24 (m, 2H), 4.97-5.07 (m, 1H), 4.89-4.97 (m, 1H), 4.24-4.38 (m, 2H), 4.18 (br d, J=13.17 Hz, 1H), 3.90-4.04 (m, 1H), 3.80 (d, J=2.09 Hz, 1H), 3.65-3.76 (m, 2H), 3.49-3.58 (m, 1H), 3.03-3.26 (m, 2H), 2.68-2.77 (m, 1H), 1.94 (s, 3H), 1.37 (t, J=7.11 Hz, 3H), 1.07 (d, J=6.69 Hz, 3H), 0.95 (d, J=6.69 Hz, 3H). $^{19}$F NMR (376 MHz, DMSO-$d_6$) δ-114.02 (s, 1F). m/z (ESI): 607.2 $(M+H)^+$.

Example 23

2-((2S)-4-(6-Chloro-7-(2-fluorophenyl)-1-(2-isopropyl-4-methylpyridin-3-yl)-2-oxo-1,2-dihydropyrido [2,3-d]pyrimidin-4-yl)-1-(oxirane-2-carbonyl)piperazin-2-yl)acetonitrile

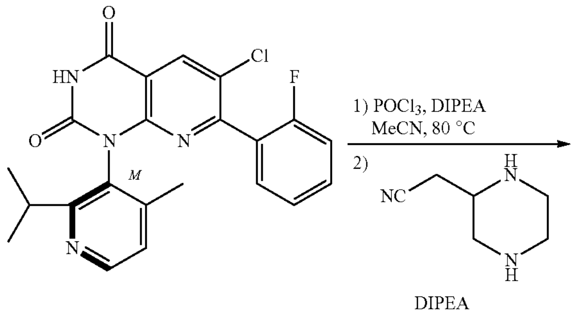

-continued

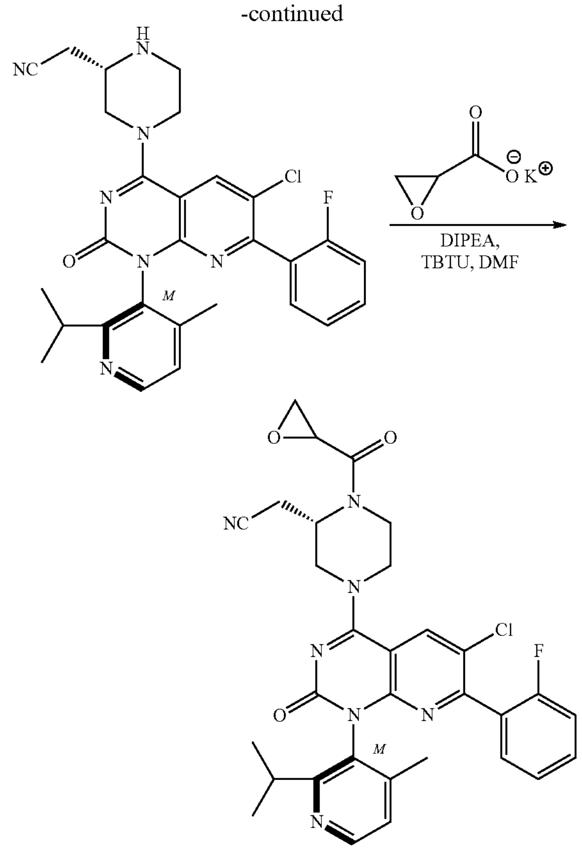

To a mixture of 6-chloro-7-(2-fluorophenyl)-1-(2-isopropyl-4-methylpyridin-3-yl)pyrido[2,3-d]pyrimidine-2,4(1H,3H)-dione (WO 2019051291 A1) (200 mg, 0.47 mmol) and DIPEA (0.12 mL, 0.71 mmol) in acetonitrile (10 mL) was added phosphorous oxychloride (0.07 mL, 0.71 mmol, Sigma-Aldrich Corporation) at room temperature and then stirred at 80° C. for 30 min. The reaction mixture was concentrated to afford 4,6-dichloro-7-(2-fluorophenyl)-1-(2-isopropyl-4-methylpyridin-3-yl)pyrido[2,3-d]pyrimidin-2(1H)-one as a brown solid. m/z (ESI): 443.0 $(M+H)^+$.

To a mixture of 4,6-dichloro-7-(2-fluorophenyl)-1-(2-isopropyl-4-methylpyridin-3-yl)pyrido[2,3-d]pyrimidin-2(1H)-one and DIPEA (0.24 mL, 1.42 mmol) in acetonitrile (10 mL) was added (S)-2-(piperazin-2-yl)acetonitrile hydrochloride (152 mg, 0.94 mmol, AstaTech Inc.) and stirred at room temperature for 1.5 h. The crude reaction mixture was concentrated and purified by silica gel chromatography (eluent: 0-10% MeOH (with 2 N $NH_3$)/DCM) to give (S)-2-(4-(6-chloro-7-(2-fluorophenyl)-1-(2-isopropyl-4-methylpyridin-3-yl)-2-oxo-1,2-dihydropyrido[2,3-d]pyrimidin-4-yl)piperazin-2-yl)acetonitrile (250 mg, 96% purity) as an yellow foam. m/z (ESI, +ve) 532.1 (M+H)

To a mixture of (S)-2-(4-(6-chloro-7-(2-fluorophenyl)-1-(2-isopropyl-4-methylpyridin-3-yl)-2-oxo-1,2-dihydropyrido[2,3-d]pyrimidin-4-yl)piperazin-2-yl)acetonitrile (250 mg, 0.470 mmol) and potassium 2-oxiranecarboxylate (89 mg, 0.71 mmol, Enamine) in DMF (2 mL) was added DIPEA (121 mg, 0.16 mL, 0.94 mmol), followed by TBTU (226 mg, 0.71 mmol, Advanced ChemTech) at 0° C. The reaction mixture was stirred at room temperature for 18 h. The resulting mixture was added water (5 mL) and extracted with EtOAc (10 mL×2). The organic extract was dried over $MgSO_4$. The solution was filtered, concentrated in vacuo and purified by silica gel chromatography (eluent: 0-50% EtOAc/EtOH (3:1)/heptane) to give 2-((2S)-4-(6-chloro-7-(2-fluorophenyl)-1-(2-isopropyl-4-methylpyridin-3-yl)-2-oxo-1,2-dihydropyrido[2,3-d]pyrimidin-4-yl)-1-(oxirane-2-carbonyl)piperazin-2-yl)acetonitrile (77.6 mg, 0.13 mmol, 27.4% yield, 95% purity) as a light yellow solid. $^1H$ NMR (400 MHz, DMSO-$d_6$) δ 8.63 (s, 1H), 8.40 (d, 1H, J=5.0 Hz), 7.5-7.6 (m, 11H), 7.3-7.3 (m, 2H), 7.2-7.2 (m, 2H), 4.8-5.1 (m, 1H), 4.1-4.5 (m, 3H), 3.9-4.0 (m, 1H), 3.7-3.9 (m, 1H), 3.5-3.7 (m, 1H), 3.4-3.4 (m, 1H), 3.0-3.2 (m, 3H), 2.7-2.9 (m, 2H), 1.92 (s, 3H), 1.07 (d, 3H, J=6.8 Hz), 0.93 (d, 3H, J=6.6 Hz). $^{19}F$ NMR (DMSO-$d_6$, 376 MHz) δ−114.4--114.1 (m, 1F). m/z (ESI): 602.2 $(M+H)^+$.

Example 24

6-Chloro-7-(2-fluorophenyl)-1-(2-isopropyl-4-methylpyridin-3-yl)-4-(6-(oxirane-2-carbonyl)-2,6-diazaspiro[3.3]heptan-2-yl)pyrido[2,3-d]pyrimidin-2(1B)-one

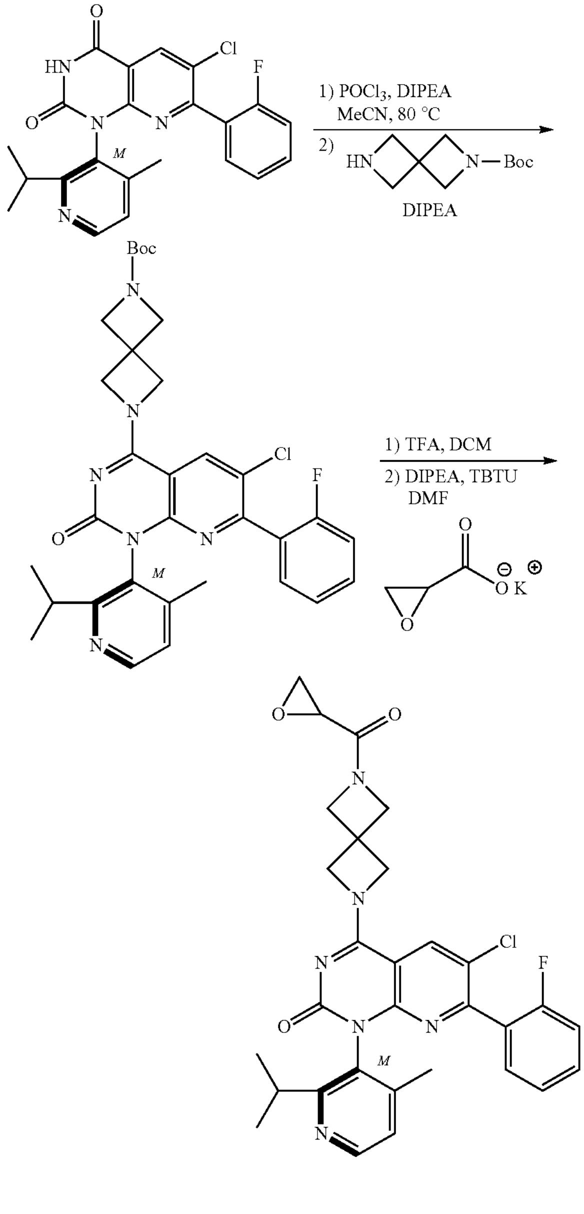

To a mixture of 6-chloro-7-(2-fluorophenyl)-1-(2-isopropyl-4-methylpyridin-3-yl)pyrido[2,3-d]pyrimidine-2,4(1H,3H)-dione (WO 2019051291 A1) (272 mg, 0.64 mmol) and DIPEA (0.12 mL, 0.96 mmol) in acetonitrile (3 mL) was added phosphorous oxychloride (0.09 mL, 0.96 mmol, Sigma-Aldrich Corporation) at room temperature and then stirred at 80° C. for 1 h. The reaction mixture was concentrated to afford 4,6-dichloro-7-(2-fluorophenyl)-1-(2-isopropyl-4-methylpyridin-3-yl)pyrido[2,3-d]pyrimidin-2(1H)-one as a brown solid. m/z (ESI): 443.0 $(M+H)^+$.

To a mixture of 74,6-dichloro-7-(2-fluorophenyl)-1-(2-isopropyl-4-methylpyridin-3-yl)pyrido[2,3-d]pyrimidin-2(1H)-one and DIPEA (0.17 mL, 0.96 mmol) in acetonitrile (3 mL) was added 2-boc-2,6-diazaspiro[3.3]heptane (210 mg, 1.06 mmol, AstaTech, Inc) and stirred at room temperature for 10 min. The crude reaction mixture was concentrated and purified by silica gel chromatography (eluent: 0-60% EtOAc/EtOH (3:1)/heptane) to give tert-butyl 6-(6-chloro-7-(2-fluorophenyl)-1-(2-isopropyl-4-methylpyridin-3-yl)-2-oxo-1,2-dihydropyrido[2,3-d]pyrimidin-4-yl)-2,6-diazaspiro[3.3]heptane-2-carboxylate (141 mg, 36.4% yield, 88% purity) as a light yellow foam. $^1$H NMR (400 MHz, DMSO-$d_6$) δ 8.36 (d, J=4.8 Hz, 1H), 8.27 (s, 1H), 7.4-7.6 (m, 1H), 7.2-7.3 (m, 2H), 7.1-7.2 (m, 2H), 5.09 (br s, 2H), 4.48 (br s, 2H), 4.12 (br s, 4H), 2.6-2.7 (m, 1H), 1.91 (s, 3H), 1.40 (s, 9H), 1.05 (d, J=6.7 Hz, 3H), 0.91 (d, J=6.7 Hz, 3H). $^{19}$F NMR (376 MHz, DMSO-$d_6$) 5-114.56 (s, 1F). m/z (ESI, +ve) 605.2 $(M+H)^+$.

To a solution of tert-butyl 6-(6-chloro-7-(2-fluorophenyl)-1-(2-isopropyl-4-methylpyridin-3-yl)-2-oxo-1,2-dihydropyrido[2,3-d]pyrimidin-4-yl)-2,6-diazaspiro[3.3]heptane-2-carboxylate (140 mg, 0.23 mmol) in dichloromethane (1 mL) was treated with trifluoroacetic acid (1.0 mL) at room temperature and stirred for 30 min. The reaction went to completion and concentrated to afford 6-chloro-7-(2-fluorophenyl)-1-(2-isopropyl-4-methylpyridin-3-yl)-4-(2,6-diazaspiro[3.3]heptan-2-yl)pyrido[2,3-d]pyrimidin-2(1H)-one, m/z (ESI, +ve) 505.2 $(M+H)^+$.

To a mixture of above 6-chloro-7-(2-fluorophenyl)-1-(2-isopropyl-4-methylpyridin-3-yl)-4-(2,6-diazaspiro[3.3]heptan-2-yl)pyrido[2,3-d]pyrimidin-2(1H)-one and potassium 2-oxiranecarboxylate (58.4 mg, 0.46 mmol, Enamine) in DMF (1 mL) was added DIPEA (0.20 mL, 1.16 mmol), followed by TBTU (149 mg, 0.46 mmol, Advanced ChemTech) at 0° C. The reaction mixture was stirred at room temperature for 2 h. The resulting mixture was added water (5 mL) and extracted with EtOAc (10 mL×2)., The organic extract was dried over $MgSO_4$. The solution was filtered, concentrated in vacuo and purified by silica gel chromatography (eluent: 0-50% EtOAc/EtOH (3:1)/heptane) to give 6-chloro-7-(2-fluorophenyl)-1-(2-isopropyl-4-methylpyridin-3-yl)-4-(6-(oxirane-2-carbonyl)-2,6-diazaspiro[3.3]heptan-2-yl)pyrido[2,3-d]pyrimidin-2(1H)-one (6 mg, 10.4 μmol, 4.51% yield, 96% purity) as a white solid. $^1$H NMR (400 MHz, DMSO-$d_6$) δ 8.37 (d, J=4.8 Hz, 1H), 8.28 (s, 1H), 7.5-7.5 (m, 1H), 7.3-7.3 (m, 2H), 7.2-7.3 (m, 1H), 7.17 (dd, J=0.7, 4.9 Hz, 1H), 5.12 (br d, J=2.3 Hz, 2H), 4.59 (br s, 2H), 4.52 (br s, 2H), 4.20 (br d, J=1.7 Hz, 2H), 3.48 (dd, J=2.6, 4.3 Hz, 1H), 2.91 (dd, J=4.4, 6.5 Hz, 1H), 2.82 (dd, J=2.5, 6.5 Hz, 1H), 2.6-2.7 (m, 1H), 1.91 (s, 3H), 1.05 (d, J=6.7 Hz, 3H), 0.92 (d, J=6.7 Hz, 3H). $^{19}$F NMR (DMSO-$d_6$, 376 MHz) δ-114.57 (s, 1F). m/z (ESI): 575.0 $(M+H)^+$.

Example 25

(R)-6-chloro-7-(2-fluorophenyl)-1-(2-isopropyl-4-methylpyridin-3-yl)-4-(2-(oxirane-2-carbonyl)-2,7-diazaspiro[3.5]nonan-7-yl)pyrido[2,3-d]pyrimidin-2(1H)-one

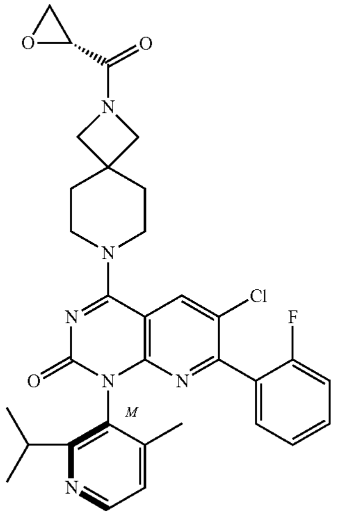

The title compound (67.3 mg, 0.11 mmol, 47% yield, 97% purity, light yellow solid) was prepared analogous to compound 24, replacing 2-boc-2,6-diazaspiro[3.3]heptane with 2-(tert-butoxycarbonyl)-2,7-diazaspiro[3.5]nonane (Combi-Blocks Inc.) in the step-2 and replacing potassium 2-oxiranecarboxylate with potassium (R)-oxirane-2-carboxylate (*Aurum* Pharmatech LLC) in the step-4. $^1$H NMR (400 MHz, DMSO-$d_6$) δ 8.42 (s, 1H), 8.39 (d, J=5.02 Hz, 1H), 7.47-7.57 (m, 1H), 7.25-7.35 (m, 2H), 7.18-7.25 (m, 2H), 4.11-4.21 (m, 2H), 3.87 (br s, 4H), 3.77 (s, 2H), 3.49 (dd, J=2.51, 4.18 Hz, 1H), 2.89-2.94 (m, 1H), 2.84 (dd, J=2.51, 6.27 Hz, 1H), 2.67-2.75 (m, 1H), 1.96-2.00 (m, 4H), 1.93 (s, 3H), 1.07 (d, J=6.90 Hz, 3H), 0.95 (d, J=6.69 Hz, 3H). $^{19}$F NMR (376 MHz, DMSO-$d_6$) δ-114.02 (d, J=4.34 Hz, 1F). m/z (ESI): 603.2 $(M+H)^+$.

Example 26

N—((R)-1-(6-Chloro-7-(2-fluorophenyl)-1-(2-isopropyl-4-methylpyridin-3-yl)-2-oxo-1,2-dihydropyrido[2,3-d]pyrimidin-4-yl)pyrrolidin-3-yl)oxirane-2-carboxamide

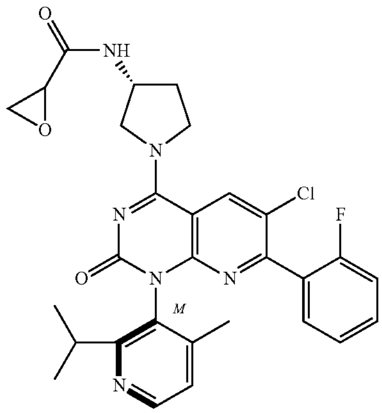

The title compound (122.7 mg, 0.22 mmol, 59.6% yield, 96% purity, light yellow solid) was prepared analogous to compound 24, replacing 2-boc-2,6-diazaspiro[3.3]heptane with (R)-3-(boc-amino)pyrrolidine (Ontario Chemical, Inc.) in the step-2. $^{1}$H NMR (400 MHz, DMSO-$d_6$) δ 8.64 (br s, 1H), 8.50 (br d, J=6.3 Hz, 1H), 8.37 (d, J=4.8 Hz, 1H), 7.5-7.5 (m, 1H), 7.2-7.3 (m, 2H), 7.2-7.2 (m, 2H), 4.46 (br s, 1H), 3.8-4.2 (m, 3H), 3.4-3.5 (m, 1H), 3.39 (dd, J=2.5, 4.2 Hz, 1H), 2.91 (dd, J=4.4, 6.3 Hz, 1H), 2.83 (dd, J=2.5, 6.3 Hz, 1H), 2.7-2.8 (m, 111), 2.21 (br d, J=3.3 Hz, 1H), 2.06 (br d, J=5.4 Hz, 1H), 1.91 (s, 3H), 1.07 (dd, J=0.7, 6.8 Hz, 3H), 0.92 (d, J=6.7 Hz, 3H). $^{19}$F NMR (376 MHz, DMSO-$d_6$) δ−114.8−−114.6 (m, 1F). m/z (ESI): 563.0 $(M+H)^+$.

Example 27

N—((R)-1-(6-Chloro-7-(2-fluorophenyl)-1-(2-isopropyl-4-methylpyridin-3-yl)-2-oxo-1,2-dihydropyrido[2,3-d]pyrimidin-4-yl)pyrrolidin-3-yl)oxirane-2-carboxamide

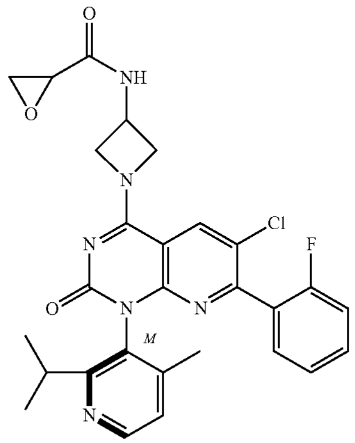

The title compound (88.4 mg, 0.16 mmol, 42.8% yield, 96% purity, light yellow solid) was prepared analogous to compound 24, replacing 2-boc-2,6-diazaspiro[3.3]heptane with 3-N-boc-amino-azetidine (AstaTech, Inc) in the step-2. $^{1}$H NMR (400 MHz, DMSO-$d_6$) δ 8.85 (br d, J=6.5 Hz, 1H), 8.37 (d, J=4.8 Hz, 1H), 8.30 (s, 1H), 7.5-7.6 (m, 1H), 7.2-7.3 (m, 2H), 7.2-7.2 (m, 2H), 5.19 (br dd, J=2.0, 7.8 Hz, 1H), 4.7-4.8 (m, 2H), 4.59 (br dd, J=2.7, 6.1 Hz, 1H), 4.2-4.4 (m, 1H), 3.44 (dd, J=2.5, 4.4 Hz, 1H), 2.97 (dd, J=4.5, 6.2 Hz, 1H), 2.85 (dd, J=2.5, 6.1 Hz, 1H), 2.6-2.7 (m, 1H), 1.92 (s, 3H), 1.06 (d, J=6.7 Hz, 3H), 0.92 (d, J=6.7 Hz, 3H). $^{19}$F NMR (376 MHz, DMSO-$d_6$) δ−114.55 (s, 1F). m/z (ESI): 549.2 $(M+H)^+$.

Example 28

6-Chloro-7-(2-fluorophenyl)-1-(2-isopropyl-4-methylpyridin-3-yl)-4-(6-(oxirane-2-carbonyl)-2,6-diazabicyclo[3.2.0]heptan-2-yl)pyrido[2,3-d]pyrimidin-2(1,H)-one

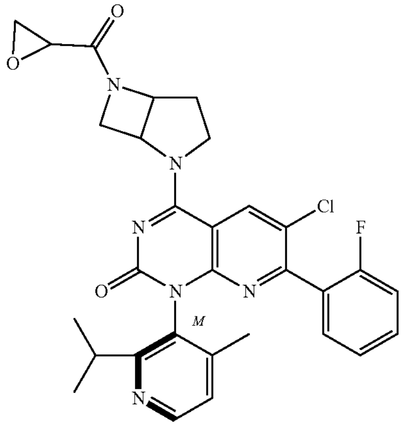

The title compound (12.4 mg, 0.02 mmol, 16.1% yield, 93% purity, white solid) was prepared analogous to compound 24, replacing 2-boc-2,6-diazaspiro[3.3]heptane with 6-boc-2,6-diazabicyclo[3.2.0]heptane (Aurum Pharmatech LLC) in the step-2. $^{1}$H NMR (400 MHz, DMSO-$d_6$) δ 8.55 (br s, 1H), 8.38 (d, J=4.8 Hz, 1H), 7.5-7.6 (m, 1H), 7.2-7.3 (m, 2H), 7.2-7.2 (m, 2H), 5.38 (br s, 1H), 5.29 (br d, J=2.7 Hz, 1H), 5.0-5.1 (m, 1H), 4.5-4.8 (m, 2H), 4.2-4.4 (m, 2H), 3.6-3.7 (m, 1H), 3.4-3.5 (m, 1H), 2.8-3.0 (m, 2H), 2.7-2.7 (m, 1H), 1.93 (d, J=8.2 Hz, 3H), 1.0-1.1 (m, 3H), 0.92 (d, J=6.7 Hz, 3H). $^{19}$F NMR (376 MHz, DMSO-$d_6$) δ−114.7−−114.0 (m, 1F). m/z (ESI): 575.1 $(M+H)^+$.

Example 29

6-Chloro-7-(2-fluorophenyl)-1-(2-isopropyl-4-methylpyridin-3-yl)-4-(methyl(1-(oxirane-

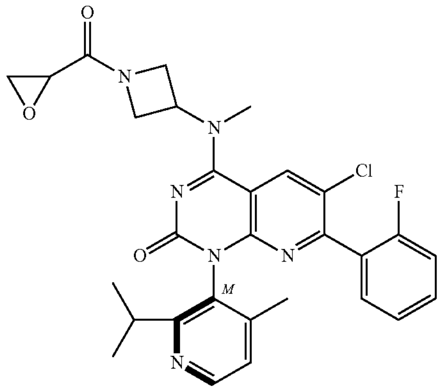

The title compound (12.4 mg, 0.02 mmol, 16.1% yield, 93% purity, white solid) was prepared analogous to compound 24, replacing 2-boc-2,6-diazaspiro[3.3]heptane with tert-butyl 3-(methylamino)azetidine-1-carboxylate (AstaTech, Inc) in the step-2. $^1$H NMR (400 MHz, DMSO-$d_6$) δ 8.55 (br d, J=2.3 Hz, 1H), 8.40 (br d, J=4.2 Hz, 1H), 7.4-7.5 (m, 1H), 7.2-7.3 (m, 4H), 4.6-4.8 (m, 1H), 3.9-4.5 (m, 1H), 3.6-3.9 (m, 4H), 3.11 (br s, 2H), 2.8-3.0 (m, 3H), 2.8-2.8 (m, 1H), 2.0-2.1 (m, 3H), 1.0-1.1 (m, 3H), 0.9-1.0 (m, 3H). $^{19}$F NMR (376 MHz, DMSO-$d_6$) δ−114.9−−114.5 (m, 1F). m/z (ESI): 563.0 (M+H)$^+$.

Example 30

(R)-6-chloro-7-(2-fluorophenyl)-1-(2-isopropyl-4-methylpyridin-3-yl)-4-(methyl(1-(oxirane-2-carbonyl)azetidin-3-yl)amino)pyrido[2,3-d]pyrimidin-2(1H)-one

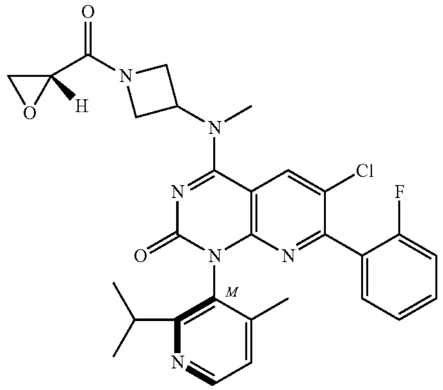

The title compound (12.4 mg, 0.02 mmol, 16.1% yield, 93% purity, white solid) was prepared analogous to compound 24, replacing 2-boc-2,6-diazaspiro[3.3]heptane with tert-butyl 3-(methylamino)azetidine-1-carboxylate (AstaTech, Inc) in the step-2 and replacing potassium 2-oxiranecarboxylate with potassium (R)-oxirane-2-carboxylate (*Aurum* Pharmatech LLC) in the step-4. $^1$H NMR (400 MHz, DMSO-$d_6$) δ 8.55 (s, 1H), 8.40 (d, J=4.8 Hz, 1H), 7.4-7.5 (m, 1H), 7.1-7.3 (m, 4H), 4.5-4.8 (m, 1H), 4.0-4.3 (m, 1H), 3.6-4.0 (m, 4H), 3.11 (d, J=4.0 Hz, 2H), 2.8-3.0 (m, 3H), 2.80 (br dd, J=3.3, 6.1 Hz, 1H), 2.0-2.1 (m, 3H), 1.1-1.1 (m, 3H), 0.9-1.0 (m, 3H). $^{19}$F NMR (376 MHz, DMSO-$d_6$) δ−114.03 (d, J=1.73 Hz, 1F). m/z (ESI): 563.2 (M+H)$^+$.

Example 31

6-Chloro-7-(2-fluorophenyl)-1-(2-isopropyl-4-methylpyridin-3-yl)-4-((1-(oxirane-2-carbonyl)azetidin-3-yl)amino)pyrido[2,3-d]pyrimidin-2(1H)-one

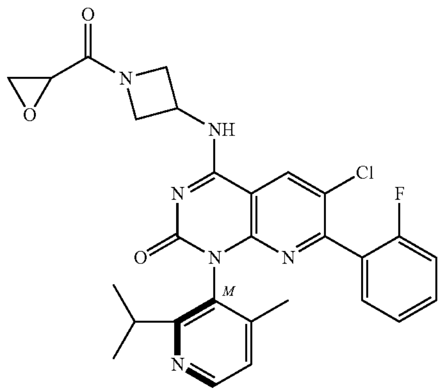

The title compound (30.5 mg, 0.06 mmol, 24.7% yield, 97% purity, white solid) was prepared analogous to compound 24, replacing 2-boc-2,6-diazaspiro[3.3]heptane with tert-butyl 3-aminoazetidine-1-carboxylate (Enamine) in the step-2. $^1$H NMR (400 MHz, DMSO-$d_6$) δ 9.31 (br s, 1H), 8.99 (d, J=3.6 Hz, 1H), 8.37 (d, J=4.8 Hz, 1H), 7.4-7.6 (m, 1H), 7.2-7.3 (m, 2H), 7.2-7.2 (m, 1H), 7.2-7.2 (m, 1H), 4.9-5.1 (m, 1H), 4.7-4.8 (m, 1H), 4.3-4.4 (m, 2H), 4.0-4.2 (m, 1H), 3.5-3.6 (m, 1H), 2.9-3.0 (m, 1H), 2.8-2.9 (m, 1H), 2.7-2.7 (m, 1H), 1.92 (s, 3H), 1.0-1.1 (m, 3H), 0.92 (d, J=6.7 Hz, 3H). $^{19}$F NMR (376 MHz, DMSO-$d_6$) δ−114.68 (s, 1F). m/z (ESI): 549.2 (M+H)$^+$.

Example 32

6-Chloro-7-(2-fluorophenyl)-1-(2-isopropyl-4-methylpyridin-3-yl)-4-(((3R)-1-(oxirane-2-carbonyl)pyrrolidin-3-yl)amino)pyrido[2,3-d]pyrimidin-2(1H)-one

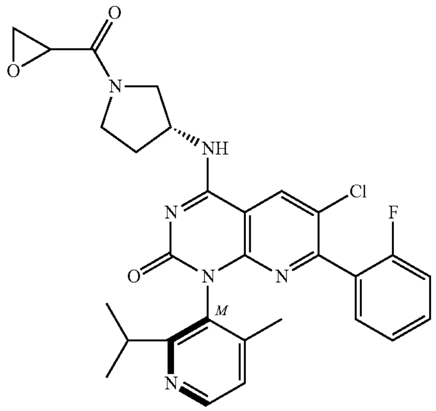

The title compound (82.7 mg, 0.15 mmol, 30% yield, 96% purity, white solid) was prepared analogous to compound 24, replacing 2-boc-2,6-diazaspiro[3.3]heptane with (R)-(+)-N-boc-3-aminopyrrolidine (CNH Technologies, Inc.) in the step-2. $^1$H NMR (400 MHz, DMSO-$d_6$) δ9.0-9.1 (m, 1H), 8.7-8.9 (m, 1H), 8.37 (d, J=4.8 Hz, 1H), 7.5-7.5 (m, 1H), 7.2-7.3 (m, 2H), 7.1-7.2 (m, 2H), 4.7-5.0 (m, 1H), 3.8-4.2 (m, 2H), 3.5-3.8 (m, 3H), 2.9-3.0 (m, 1H), 2.8-2.9 (m, 1H), 2.7-2.8 (m, 1H), 2.0-2.4 (m, 2H), 1.93 (s, 3H), 1.06 (d, J=6.7 Hz, 3H), 0.92 (dd, J=2.5, 6.7 Hz, 3H). $^{19}$F NMR (376 MHz, DMSO-$d_6$) δ−114.8−−114.6 (m, 1F). m/z (ESI): 563.2 (M+H)$^+$.

Example 33

6-Chloro-7-(2-fluorophenyl)-1-(2-isopropyl-4-methylpyridin-3-yl)-4-(7-(oxirane-2-carbonyl)-2,7-diazabicyclo[4.2.0]octan-2-yl)pyrido[2,3-d]pyrimidin-2(1H)-one

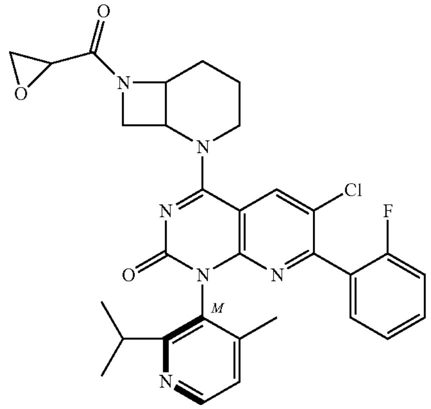

The title compound (91.8 mg, 0.16 mmol, 77% yield, 96% purity, light yellow solid) was prepared analogous to compound 24, replacing 2-boc-2,6-diazaspiro[3.3]heptane with 7-boc-2,7-diazabicyclo[4.2.0]octane (Aurum Pharmatech LLC) in the step-2. $^1$H NMR (400 MHz, DMSO-$d_6$) δ 8.56 (br s, 1H), 8.40 (d, J=4.8 Hz, 1H), 7.4-7.6 (m, 1H), 7.2-7.3 (m, 2H), 7.2-7.2 (m, 2H), 4.86 (ddd, J=2.5, 7.8, 10.3 Hz, 1H), 3.6-4.5 (m, 6H), 2.9-3.0 (m, 2H), 2.8-2.9 (m, 1H), 2.1-2.2 (m, 1H), 2.04 (d, J=8.1 Hz, 3H), 1.82 (br d, J=1.9 Hz, 1H), 1.4-1.7 (m, 2H), 1.1-1.1 (m, 3H), 0.9-1.0 (m, 3H). $^{19}$F NMR (376 MHz, DMSO-$d_6$) δ−115.0−−114.5 (m, 1F). m/z (ESI): 589.1 $(M+H)^+$.

Example 34

N—((S)-1-(6-Chloro-7-(2-fluorophenyl)-1-(2-isopropyl-4-methylpyridin-3-yl)-2-oxo-1,2-dihydropyrido[2,3-d]pyrimidin-4-yl)piperidin-3-yl)oxirane-2-carboxamide

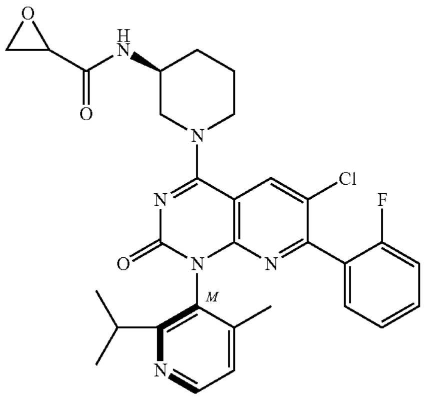

The title compound (168 mg, 0.29 mmol, 70.8% yield, 95% purity, light yellow solid) was prepared analogous to compound 24, replacing 2-boc-2,6-diazaspiro[3.3]heptane with (S)-3-boc-aminopiperidine (Aurum Pharmatech LLC) in the step-2. $^1$H NMR (400 MHz, DMSO-$d_6$) δ 8.53 (d, J=2.1 Hz, 1H), 8.38 (d, J=4.8 Hz, 1H), 8.24-8.37 (m, 1H), 7.46-7.55 (m, 1H), 7.24-7.34 (m, 2H), 7.16-7.23 (m, 2H), 4.13-4.34 (m, 2H), 3.95-4.02 (m, 1H), 3.33-3.52 (m, 3H), 2.88 (ddd, J=13.1, 6.3, 4.4 Hz, 1H), 2.72-2.83 (m, 1H), 2.59-2.69 (m, 1H), 1.97-2.02 (m, 2H), 1.94 (s, 3H), 1.61-1.86 (m, 2H), 1.06 (d, J=6.7 Hz, 3H), 0.94 (d, J=6.7 Hz, 3 H). $^{19}$F NMR (376 MHz, DMSO-$d_6$) δ−114.09 (d, J=12.1 Hz, 1 F). m/z (ESI): 577.2 $(M+H)^+$.

Example 35

N—((S)-1-(6-chloro-7-(2-fluorophenyl)-1-(2-isopropyl-4-methylpyridin-3-yl)-2-oxo-1,2-dihydropyrido[2,3-d]pyrimidin-4-yl)pyrrolidin-3-yl)oxirane-2-carboxamide

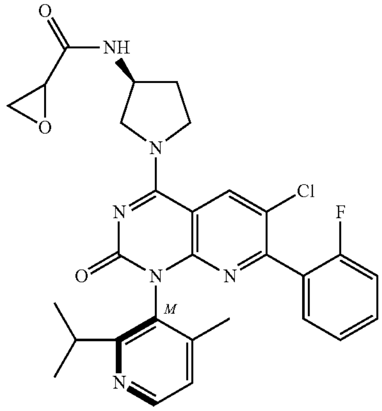

The title compound (117 mg, 0.21 mmol, 48.4% yield, 95% purity, light yellow solid) was prepared analogous to compound 24, replacing 2-boc-2,6-diazaspiro[3.3]heptane with (S)-(−)-3-(boc-amino)pyrrolidine (CNH Technologies, Inc.) in the step-2. $^1$H NMR (400 MHz, DMSO-$d_6$) δ 8.64 (br s, 1H), 8.48 (br d, J=6.7 Hz, 1H), 8.37 (d, J=4.8 Hz, 1H), 7.5-7.5 (m, 11H), 7.2-7.3 (m, 2H), 7.2-7.2 (m, 2H), 4.46 (br d, J=4.2 Hz, 1H), 3.7-4.1 (m, 3H), 3.4-3.5 (m, 1H), 3.39 (dd, J=2.4, 4.3 Hz, 1H), 2.91 (dd, J=4.4, 6.3 Hz, 1H), 2.83 (ddd, J=1.1, 2.4, 6.3 Hz, 1H), 2.6-2.7 (m, 1H), 2.1-2.3 (m, 1H), 2.04 (br d, J=5.2 Hz, 1H), 1.94 (s, 3H), 1.0-1.1 (m, 3H), 0.92 (d, J=6.7 Hz, 3H). $^{19}$F NMR (376 MHz, DMSO-$d_6$) δ−114.30 (s, 1F). m/z (ESI): 563.2 $(M+H)^+$.

Example 36

6-Chloro-4-((2S,5R)-2,5-dimethyl-4-((R)-oxirane-2-carbonyl)piperazin-1-yl)-7-(2-fluoro-6-hydroxyphenyl)-1-(2-isopropyl-4-methylpyridin-3-yl)pyrido[2,3-d]pyrimidin-2(1H)-one

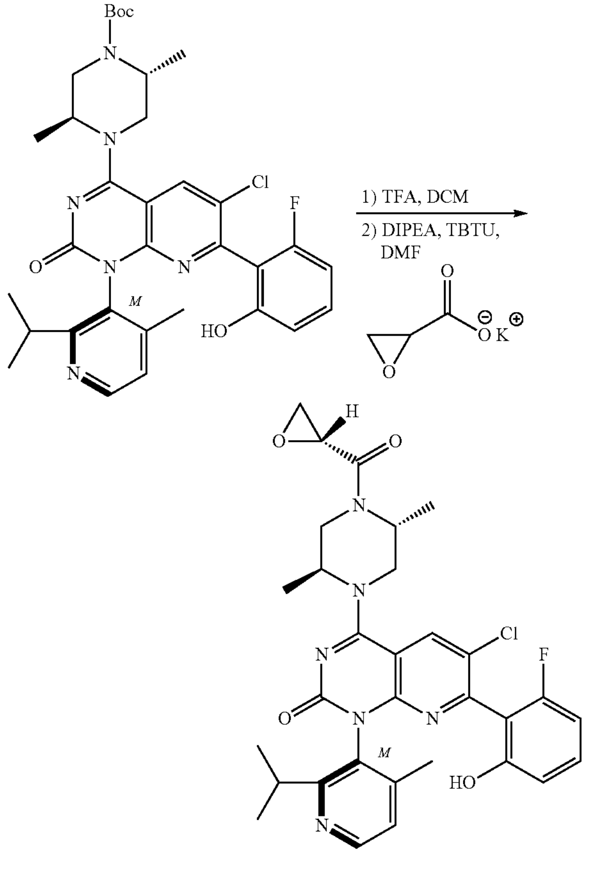

To a solution of tert-butyl (2R,5S)-4-(6-chloro-7-(2-fluoro-6-hydroxyphenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (WO 2019051291 A1) (140 mg, 0.22 mmol) in dichloromethane (1 mL) was treated with TFA (1.0 mL) at rt and stirred for 10 min. The reaction went to completion and concentrated to afford 6-chloro-4-((2S,5R)-2,5-dimethylpiperazin-1-yl)-7-(2-fluoro-6-hydroxyphenyl)-1-(2-isopropyl-4-methylpyridin-3-yl)pyrido[2,3-d]pyrimidin-2(1H)-one, m/z (ESI, +ve) 537.2 $(M+H)^+$.

To a mixture of 6-chloro-4-((2S,5R)-2,5-dimethylpiperazin-1-yl)-7-(2-fluoro-6-hydroxyphenyl)-1-(2-isopropyl-4-methylpyridin-3-yl)pyrido[2,3-d]pyrimidin-2(1H)-one and potassium (R)-oxirane-2-carboxylate (41.6 mg, 0.33 mmol, Aurum Pharmatech LLC) in N, N-dimethylformamide (1 mL) was added DIPEA (0.19 mL, 1.10 mmol), followed by TBTU (106 mg, 0.33 mmol, Advanced ChemTech) at 0° C. The reaction mixture was stirred at room temperature for 1 h. The resulting mixture was added water (10 mL) and extracted with EtOAc (20 mL×2). The organic extract was dried over $MgSO_4$. The solution was filtered, concentrated in vacuo and purified by silica gel chromatography (eluent: 0-100% EtOAc-MeOH (9:1)/heptane) to give 6-chloro-4-((2S,5R)-2,5-dimethyl-4-((R)-oxirane-2-carbonyl)piperazin-1-yl)-7-(2-fluoro-6-hydroxyphenyl)-1-(2-isopropyl-4-methylpyridin-3-yl)pyrido[2,3-d]pyrimidin-2(1H)-one (39.5 mg, 0.07 mmol, 29.6% yield, 96% purity) as an yellow solid. $^1H$ NMR (400 MHz, DMSO-$d_6$) δ 10.01-10.24 (m, 1H), 8.43 (br s, 1H), 8.38 (d, J=4.77 Hz, 1H), 7.20-7.28 (m, 1H), 7.18 (d, J=4.77 Hz, 1H), 6.62-6.74 (m, 2H), 4.86 (br d, J=1.24 Hz, 1H), 4.57-4.74 (m, 1H), 4.04-4.32 (m, 2H), 3.79-3.95 (m, 3H), 2.93-3.01 (m, 1H), 2.83 (dd, J=2.38, 6.32 Hz, 1H), 2.65-2.76 (m, 1H), 1.91 (br s, 3H), 1.29-1.39 (m, 4H), 1.19-1.29 (m, 2H), 1.07 (d, J=6.84 Hz, 3H), 0.94 (br d, J=6.43 Hz, 3H). $^{19}F$ NMR (376 MHz, DMSO-$d_6$) δ−115.83 (br d, J=267.89 Hz, 1F). m/z (ESI, +ve) 607.2 $(M+H)^+$.

Example 37

7-(2-Amino-6-fluorophenyl)-6-chloro-4-((2S,5R)-2,5-dimethyl-4-((R)-oxirane-2-carbonyl)piperazin-1-yl)-1-(2-isopropyl-4-methylpyridin-3-yl)pyrido[2,3-d]pyrimidin-2(1H)-one

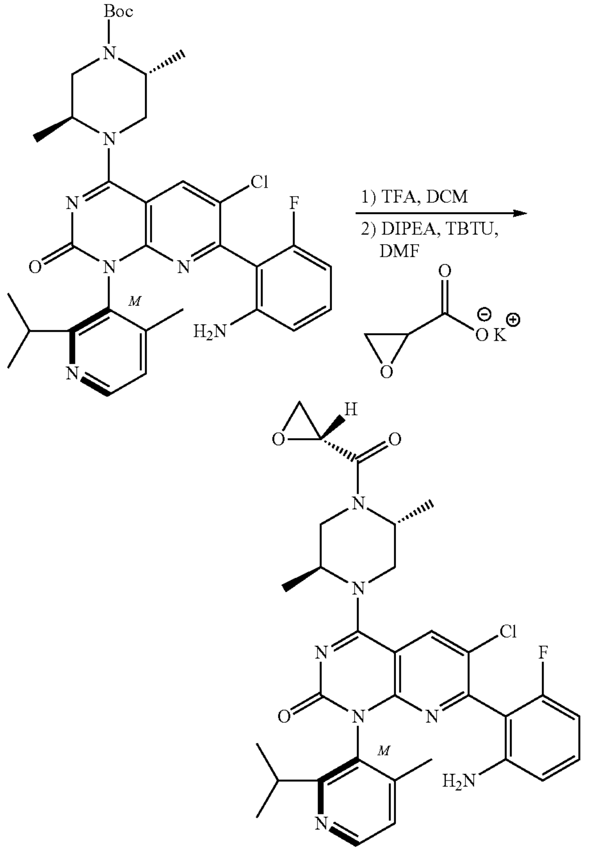

To a solution of tert-butyl (2R,5S)-4-(7-(2-amino-6-fluorophenyl)-6-chloro-1-(2-isopropyl-4-methylpyridin-3-yl)-2-oxo-1,2-dihydropyrido[2,3-d]pyrimidin-4-yl)-2,5-dimethylpiperazine-1-carboxylate (WO 2019051291 A1) (260 mg, 0.41 mmol) in dichloromethane (1 mL) was treated with trifluoroacetic acid (1 mL) at room temperature and stirred for 10 min. The reaction went to completion and concentrated to afford 7-(2-amino-6-fluorophenyl)-6-chloro-4-((2S,5R)-2,5-dimethylpiperazin-1-yl)-1-(2-isopropyl-4-methylpyridin-3-yl)pyrido[2,3-d]pyrimidin-2(1H)-one, m/z (ESI, +ve) 536.2 $(M+H)^+$.

To a mixture of 7-(2-amino-6-fluorophenyl)-6-chloro-4-((2S,5R)-2,5-dimethylpiperazin-1-yl)-1-(2-isopropyl-4-methylpyridin-3-yl)pyrido[2,3-d]pyrimidin-2(1H)-one and potassium (R)-oxirane-2-carboxylate (77 mg, 0.613 mmol, Aurum Pharmatech LLC) in N, N-dimethylformamide (1 mL) was added DIPEA (0.36 mL, 2.04 mmol), followed by TBTU (197 mg, 0.61 mmol, Advanced ChemTech) at 0° C. The reaction mixture was stirred at room temperature for 1 h. The resulting mixture was added water (10 mL) and extracted with EtOAc (20 mL×2). The organic extract was dried over $MgSO_4$. The solution was filtered, concentrated in vacuo and purified by silica gel chromatography (eluent: 0-100% EtOAc-MeOH (9:1)/heptane) to give 7-(2-amino-6-fluorophenyl)-6-chloro-4-((2S,5R)-2,5-dimethyl-4-((R)-oxirane-2-carbonyl)piperazin-1-yl)-1-(2-isopropyl-4-methylpyridin-3-yl)pyrido[2,3-d]pyrimidin-2(1H)-one (173 mg, 0.29 mmol, 69.9% yield, 99% purity) as an yellow solid. $^1H$ NMR (400 MHz, DMSO-$d_6$) δ ppm 8.44 (s, 1H), 8.39 (d, J=4.8 Hz, 1H), 7.19 (d, J=4.8 Hz, 1H), 7.05 (q, J=7.5 Hz, 1H), 6.45 (d, J=8.3 Hz, 1H), 6.26-6.38 (m, 1H), 5.06-5.16 (m, 2H), 4.80-4.92 (m, 1H), 4.56-4.77 (m, 1H), 4.01-4.22 (m, 2H), 3.86-3.99 (m, 2H), 2.97 (dd, J=6.0, 4.6 Hz, 1H), 2.79-2.88 (m, 1H), 2.57-2.73 (m, 1H), 1.81-2.03 (m, 3H), 1.23-1.41 (m, 5H), 1.14-1.21 (m, 2H), 0.87-1.10 (m, 6H). $^{19}F$ NMR (376 MHz, DMSO-$d_6$) δ ppm −115.83-−115.48 (m, 1 F). m/z (ESI, +ve) 606.2 $(M+H)^+$.

Table 1: Biochemical and Cellular Activity of Compounds

For compounds in Table 1, the following assay conditions were employed:

Coupled Nucleotide Exchange Assay: Purified GDP-bound KRAS protein (aa 1-169), containing either G12C or G12D, as well as C118A amino acid substitutions and an N-terminal His-tag, was pre-incubated in assay buffer (25 mM HEPES pH 7.4, 10 mM $MgCl_2$, and 0.01% Triton X-100) with a compound dose-response titration for either 5 min or 20 hours (see Table 15). Following compound pre-incubation, purified SOS protein (aa 564-1049) and GTP (Roche 10106399001) were added to the assay wells and incubated for an additional 30 min. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 10 minutes. The assay plates were then read on a PerkinElmer EnVision Multilabel Reader, using AlphaScreen® technology, and data were analyzed using a 4-parameter logistic model to calculate $IC_{50}$ values.

Phospho-ERK1/2 MSD Assay: MIA PaCa-2 (ATCC® CRL-1420™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 cells were seeded in 96-well cell culture plates at a density of 25,000 cells/well and incubated at 37° C., 5% $CO_2$. A compound dose-response titration was diluted in growth media, added to appropriate wells of a cell culture plate, and then incubated at 37° C., 5% $CO_2$ for 2 or 4 hours (see Table 15). Following compound treatment, cells were washed with ice-cold Dulbecco's phosphate-buffered saline, no $Ca^{2+}$ or $Mg^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate $IC_{50}$ values.

GDP-KRAS G12D RF-MS Assay: MS assays were performed in the following buffer: 25 mM HEPES pH 7.4, 20 mM $MgCl_2$, 10 mM NaCl, 3% DMSO, 0.0005% CHAPS with 100 μM GDP made fresh and added to the assay buffer. The final concentration of KRAS G12D was 2 uM. Assay incubation times were 20 h and the inhibitor concentration was 100 μM. Greiner polypropylene clear V-bottom plates were used for the mass spectrometry assays. Typically, the reaction was initiated by addition of KRAS G12D to a well containing inhibitor followed by Rapidfire MS analysis. Relative % Bound values at the various incubation times were used to estimate a kobs value at 100 uM inhibitor.

Instrumentation

RapidFire Sample Liquid handling System: The RapidFire liquid handling unit used was the RF 360 model. Solvents were delivered by Agilent 1260 Infinity pumps. The instrument control software was the Agilent RapidFire High Throughput MS-system software (v4.0.12333.14274). A single C4 Type A (Agilent technologies, G9203) SPE-cartridge was used for these experiments. A volume of 10 μL (sample loop determined) was removed from each well of a 384-well plate by using an aspiration time of 300 ms. The sample load/wash time was 6000 ms at a flow rate of 1.25 mL/min ($H_2O$, 0.1% v/v formic acid, 0.05% v/v trifluoroacetic acid); elution time was 7000 ms (acetonitrile, 0.1% v/v formic acid, 0.05% v/v trifluoroacetic acid); re-equilibration time was 700 ms at a flow rate of 1.25 mL/min ($H_2O$, 0.1% v/v formic acid, 0.05% v/v trifluoroacetic acid).

Mass Spectrometry: Mass spectrometric data was acquired on an Agilent 6530 quadrupole time-of-flight (ToF) MS system, operated with a dual Agilent Jet Spray (AJS) ion source, in positive ionization mode. The instrument parameters were as follows: gas temperature 350° C.; drying gas 5 L/min; nebulizer 60 psi; sheath gas 350° C.; sheath gas flow 11 L/min; capillary 3.5 kV (0.037 μA); nozzle 1.75 kV; fragmentor 200 V; skimmer 75 V; octapole RF 800 V peak-to-peak. Data was acquired at the rate of 5 spectra/s. The mass scale was calibrated using the Agilent positive ion tune mix, over the m/z range 300-3200. The instrument control software was Agilent MassHunter Workstation Data Acquisition (vB.05.01).

Mass Spectrometry Data Processing and Informatics: All data processing was performed using a HP Z620, 64-bit, 12-processor, Windows 7 PC, using a combination of Agilent MassHunter Qualitative Analysis (B.05.00) Agilent RapidFire control software (v4.0.12333.14070) and the Agilent DA Reprocessor Offline Utilities B.05.00, Build 162. The SPE-MS data acquired from the RapidFire-MS system is typically a single SPE-MS data file composed of multiple injection events. For effective charge state extraction, SPE-peak integration and subsequent MS-spectral deconvolution, the single SPE-MS data file is split into single injection events. This is typically performed off-line and achieved through the RapidFire User Interface software, using the Agilent RapidFire control software (v4.0.12333.14070) using the Convert MS Data option. Once the individual injection-event MS-data files have been produced, they are all batch processed using the DA Reprocessor Offline Utilities (B.05.00, Build 162, Agilent). For batch processing a method file was created using Agilent MassHunter Qualitative Analysis B.05.00. The details of this method file are contained within the BioConfirm Workflow and are as follows: Integrate (MS), Integrator Selection: General, smooth option selected; detector point sampling 1; start threshold 5.0; stop threshold 0.0; filtering 5 point; peak location, top. Extract (MS): Peak Spectrum Extraction (MS) within m/z 800-1400. Deconvolute (MS) Maximum Entropy: mass range 19,000-21,000 Daltons; Mass step 1.0 Da; S/N threshold 20.0; Use limited m/z range 800-1400; adduct proton; isotope peak width automatic; minimum consecutive charge states 5.

Once the individual injection event MS-files are processed using the method file described above, a single report file is generated for each injection event MS-file, in the form of an Excel spreadsheet. Relevant protein molecular weight and intensity values, contained within specific cells in the spread sheet are extracted from the Excel report/results file using a custom routine written within Pipeline Pilot (BIOVIA) and used to calculate percent-of-control (POC) and percent-bound (%-Bound) values in the form of a concatenated output file (text, tab delimited in format; Figure S4*a*). POC=(Unmodified Protein Peak Intensity/Control Protein Peak Intensity)×100 and % Bound=(Expected Protein Adduct Peak Intensity/Control Protein Peak Intensity)×100. Relative % Bound=% Bound/(POC+% Bound)×100 is a normalized measure of covalent binding that accounts for sample variability or compound effects on ionization or detection efficiencies. These values are then input into Amgen's data analysis suite (Genedata) for further data analysis and then finally loaded into Amgen's central database. The specific input files for the Pipeline Pilot script are the Excel report/result file directory; the compound molecular weight file (Amgen registry compound number and expected covalent modification) and the Injection Sequence File (RFTIME file; not shown), which is produced during the RapidFire-MS acquisition and contains the injection sequence, injection position and the plate bar code (which corresponds with the 384-well plate map dispensed by the Amgen Sample Bank). Additional information that is manually input to the Pipeline Pilot routine via a user interface are the protein's molecular weight (average molecular weight in Da) and the molecular weight variance, typically 0.01% (±2 Da for a 19.5 kDa protein).

TABLE 1

| Ex # | GDP KRAS G12C 5 min Coupled Exchange IC50 IP (μM) | GDP KRAS G12C 20 h Coupled Exchange IC50 IP (μM) | basal p-ERK 2 h MIA PaCa-2 (G12C) IC50 IP (μM) | GDP KRAS G12D 20 h Coupled Exchange IC50 IP (μM) | GDP-KRAS G12D RF-MS 100 μM 20 h Relative % Bound (%) |
|---|---|---|---|---|---|
| 1 | 1.29 | 0.026 | nda | >250 | nda |
| 2 | >250 | 13.4 | nda | >250 | nda |
| 3 | nda | 31.3 | nda | >250 | nda |
| 4 | 0.61 | 0.039 | 0.711 | >250 | nda |
| 5 | 0.095 | 0.026 | 0.061 | >250 | nda |
| 6 | >250 | 131 | nda | >250 | nda |
| 7 | >250 | 26.2 | nda | >250 | nda |
| 8 | >250 | 24 | nda | >250 | nda |
| 9 | 33.9 | 2.45 | nda | >250 | nda |
| 10 | 38.3 | 1.84 | nda | >250 | nda |
| 11 | 69.8 | 5.45 | nda | >250 | nda |
| 12 | 35.7 | 2.02 | nda | >250 | nda |
| 13 | 8.59 | 0.54 | nda | >250 | nda |
| 14 | 88.3 | 1.56 | nda | >250 | nda |
| 15 | 74.1 | 0.83 | nda | >250 | nda |
| 16 | 3.78 | 0.027 | nda | 190 | 3.4 |
| 17 | 17.8 | 0.096 | nda | >250 | nda |
| 18 | 23.9 | 0.53 | nda | >250 | nda |
| 19 | 0.216 | 0.005 | 0.096 | >250 | 3.4 |
| 20 | nda | 1 | nda | >250 | nda |
| 21 | 1.12 | 0.005 | nda | >250 | nda |
| 22 | 6.26 | 0.064 | nda | >250 | nda |
| 23 | >250 | 0.431 | nda | >250 | nda |
| 24 | 222 | 41.6 | nda | >250 | nda |
| 25 | nda | 7.15 | nda | >250 | nda |
| 26 | 194 | 2.99 | nda | >250 | nda |
| 27 | 4.41 | 0.018 | nda | >250 | nda |
| 28 | 193 | 0.647 | nda | >250 | nda |
| 29 | 13.8 | 0.227 | nda | >250 | nda |
| 30 | >250 | >31.3 | nda | >250 | 1.4 |
| 31 | 146 | 1.57 | nda | >250 | 2.2 |
| 32 | 101 | 1.85 | nda | >250 | 3.1 |
| 33 | 60.9 | 0.261 | nda | >250 | 2 |
| 34 | >250 | >250 | nda | >250 | 2.9 |
| 35 | 167 | 1.36 | nda | >250 | 3.4 |
| 36 | 0.653 | 0.024 | nda | >250 | 8.1 |
| 37 | 0.56 | 0.015 | nda | >250 | 15.8 |

"nda" = no data available

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed:

1. A compound having a structure of formula (I)

(I)

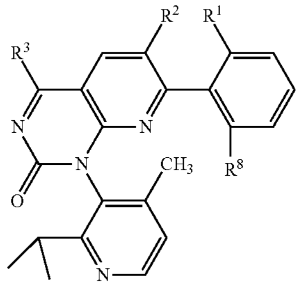;

wherein $R^1$ is H, halo, or —$CH_3$;

$R^2$ is H, halo, or —$CH_3$;

$R^3$ is

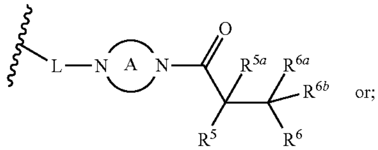 or;

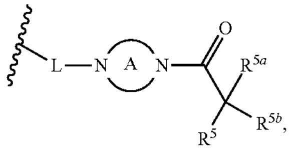, ring A is a monocyclic 4-7 membered ring or a bicyclic, bridged, fused, or spiro 6-11 membered ring;

L is a bond;

$R^5$ is H, halo, an —$C_{1-6}$ alkyl, —$C_{2-6}$ alkynyl, —$C_{0-6}$ alkylene-O—$C_{1-6}$ alkyl, —$C_{1-6}$ alkylene-O—$C_{1-4}$alkyl, —$C_{1-6}$ alkylene-OH, —$C_{1-6}$ haloalkyl, —$C_{1-6}$ alkyleneamine, —$C_{0-6}$ alkylene-amide, —C(O)OH, —C(O)O$C_{1-4}$alkyl, —$C_{0-6}$ alkylene-O—$C_{6-14}$ aryl, —$C_{0-3}$ alkylene-C(O)$C_{1-4}$ alkylene-OH, cycloalkyl, heterocycloalkyl, aryl, heteroaryl, —$C_{0-3}$ alkylene-$C_{3-14}$ cycloalkyl, —$C_{0-3}$ alkylene-$C_{2-14}$ heterocycloalkyl, —$C_{0-3}$ alkylene-$C_{6-14}$ aryl, —$C_{0-3}$ alkylene-$C_{2-14}$ heteroaryl, or cyano;

$R^{5a}$ is selected from H, —$C_{1-6}$ alkyl, —$C_{2-6}$ alkynyl, —$C_{1-6}$ alkylene-O—$C_{1-4}$ alkyl, —$C_{1-6}$ alkylene-OH, —$C_{1-6}$ haloalkyl, —$C_{1-6}$ alkyleneamine, —$C_{0-6}$ alkylene-amide, —C(O)OH, —C(O)O$C_{1-4}$ alkyl, —$C_{0-6}$ alkylene-O—$C_{6-14}$ aryl, —$C_{0-3}$ alkylene-C(O)$C_{1-4}$ alkylene-OH, cycloalkyl, heterocycloalkyl, aryl, heteroaryl, —$C_{0-3}$ alkylene-$C_{3-14}$ cycloalkyl, —$C_{0-3}$ alkylene-$C_{2-14}$ heterocycloalkyl, —$C_{0-3}$ alkylene-$C_{6-14}$ aryl, or —$C_{0-3}$ alkylene-$C_{2-14}$ heteroaryl;

$R^{5b}$ is selected from H, —$C_{1-6}$ alkyl, —$C_{2-6}$ alkynyl, —$C_{1-6}$ alkylene-O—$C_{1-4}$ alkyl, —$C_{1-6}$ alkylene-OH, —$C_{1-6}$ haloalkyl, —$C_{1-6}$ alkyleneamine, —$C_{0-6}$ alkylene-amide, —C(O)OH, —C(O)O$C_{1-4}$alkyl, —$C_{0-6}$ alkylene-O—$C_{6-14}$ aryl, —$C_{0-3}$ alkylene-C(O)$C_{1-4}$ alkylene-OH, cycloalkyl, heterocycloalkyl, aryl, heteroaryl, —$C_{0-3}$ alkylene-$C_{3-14}$ cycloalkyl, —$C_{0-3}$ alkylene-$C_{2-14}$ heterocycloalkyl, —$C_{0-3}$ alkylene-$C_{6-14}$ aryl, or —$C_{0-3}$ alkylene-$C_{2-14}$ heteroaryl;

or $R^{5a}$ and $R^{5b}$ together, may represent an =O or =N=N;

$R^6$ is H, halo, —$C_{1-6}$ alkyl, —$C_{2-6}$ alkynyl, —$C_{1-6}$ alkylene-O—$C_{1-4}$ alkyl, —$C_{1-6}$ alkylene-OH, —$C_{1-6}$ haloalkyl, —$C_{1-6}$ alkyleneamine, —$C_{0-6}$ alkylene-amide, —C(O)OH, —C(O)O$C_{1-4}$ alkyl, —$C_{0-6}$ alkylene-O—$C_{6-14}$ aryl, —$C_{0-3}$ alkylene-C(O)$C_{1-4}$ alkylene-OH, cycloalkyl, heterocycloalkyl, aryl, heteroaryl, —$C_{0-3}$ alkylene-$C_{3-14}$ cycloalkyl, —$C_{0-3}$ alkylene-$C_{2-14}$ heterocycloalkyl, —$C_{0-3}$ alkylene-$C_{6-14}$ aryl, or —$C_{0-3}$ alkylene-$C_{2-14}$ heteroaryl;

$R^{5a}$ and $R^{6a}$, together with the atoms to which they are attached, may form a 3-6 membered ring that optionally includes one or two heteroatoms selected from O, S or N;

$R^{6a}$ is H or —$C_{1-6}$ alkyl;

$R^{6b}$ is H, —$C_{1-6}$ alkyl, —$C_{2-6}$ alkynyl, —$C_{1-6}$ alkylene-O—$C_{1-4}$ alkyl, —$C_{1-6}$ alkylene-OH, —$C_{1-6}$ haloalkyl, —$C_{1-6}$ alkyleneamine, —$C_{0-6}$ alkylene-amide, —C(O)OH, —C(O)O$C_{1-4}$ alkyl, —$C_{0-6}$ alkylene-O—$C_{6-14}$ aryl, —$C_{0-3}$ alkylene-C(O)$C_{1-4}$ alkylene-OH, cycloalkyl, heterocycloalkyl, aryl, heteroaryl, —$C_{0-3}$ alkylene-$C_{3-14}$ cycloalkyl, —$C_{0-3}$ alkylene-$C_{2-14}$ heterocycloalkyl, —$C_{0-3}$ alkylene-$C_{6-14}$ aryl, —$C_{0-3}$ alkylene-$C_{2-14}$ heteroaryl, or cyano;

or $R^{6a}$ and $R^{6b}$ together, may represent an =O;

$R^8$ is H, OH, or $N^aR^b$;

wherein $R^a$ and $R^b$ are each independently H, halo, —$C_{1-6}$ alkyl, or —$C_{2-6}$ alkynyl;

wherein the ring A or the —$C_{1-6}$ alkyl, —$C_{2-6}$ alkynyl, —$C_{1-6}$ alkylene-O—$C_{1-4}$ alkyl, —$C_{1-6}$ alkylene-OH, —$C_{1-6}$ haloalkyl, —$C_{1-6}$ alkyleneamine, —$C_{0-6}$ alkylene-amide, —C(O)O$C_{1-4}$ alkyl, —$C_{1-6}$ alkylene-O-aryl, —$C_{0-3}$ alkylene-C(O)$C_{1-4}$ alkylene-OH, cycloalkyl, heterocycloalkyl, aryl, heteroaryl, —$C_{0-3}$ alkylene-$C_{3-14}$ cycloalkyl, —$C_{0-3}$ alkylene-$C_{2-14}$ heterocycloalkyl, —$C_{0-3}$ alkylene-$C_{6-14}$ aryl, or —$C_{0-3}$ alkylene-$C_{2-14}$ heteroaryl groups of any of the $R^5$, $R^{5a}$, $R^{5b}$, $R^6$, $R^{6a}$, $R^{6b}$, and $R^8$ may be unsubstituted or substituted with 1, 2, 3, or 4 substituents, as allowed, independently selected from halo, —$C_{1-6}$ alkyl, —O—$C_{1-6}$ alkyl, —OH, or —$C_{1-6}$ alkyl-CN;

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

2. The compound or salt of claim 1, having the structure:

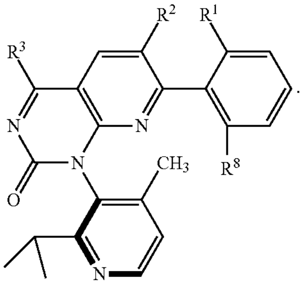

3. The compound or salt of claim 1, wherein ring A is a monocyclic 4-7 membered ring.

4. The compound or salt of claim 1, wherein ring A is a bicyclic ring.

5. The compound or salt of claim 1, wherein ring A is a spiro 6-11 membered ring.

6. The compound or salt of claim 1, wherein $R^1$ is F or Cl.

7. The compound or salt of claim 1, wherein $R^5$ is H, halo, —$C_{1-6}$ alkyl, or —$C_{0-6}$ alkylene-O—$C_{6-14}$ aryl.

8. The compound or salt of claim 1, wherein $R^{5a}$ is selected from H, —$C_{1-6}$ alkyl, —$C_{1-6}$ alkylene-OH, —C(O)OH, —C(O)O$C_{1-4}$ alkyl, and —$C_{0-3}$ alkylene-$C_{2-14}$ heterocycloalkyl.

9. The compound or salt of claim 1, wherein $R^6$ is H, halo, or —$C_{1-6}$ alkyl.

10. The compound or salt of claim 1, wherein $R^{6b}$ is H, —$C_{1-6}$ alkyl, $C_{1-6}$ alkylene-OH, —C(O)OH, —C(O)O$C_{1-4}$ alkyl, or —$C_{0-3}$ alkylene-$C_{2-14}$ heterocycloalkyl.

11. The compound or salt of claim 1, wherein $R^{6a}$ and $R^{6b}$ form a ═O.

12. The compound or salt of claim 1, wherein $R^{6a}$ is H, or —$C_{1-6}$ alkyl.

13. The compound or salt of claim 1, wherein $R^{5b}$ is selected from H, —$C_{1-6}$ alkyl, —$C_{1-6}$ alkylene-OH, —C(O)OH, —C(O)O$C_{1-4}$ alkyl, or —$C_{0-3}$ alkylene-$C_{2-14}$ heterocycloalkyl.

14. The compound or salt of claim 1, wherein $R^3$ is,

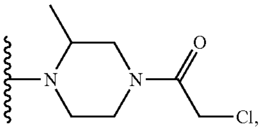
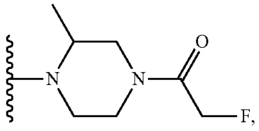
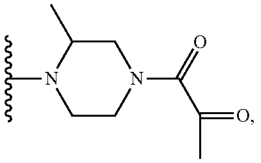
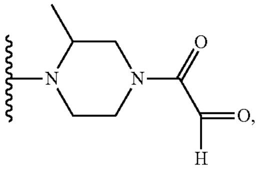
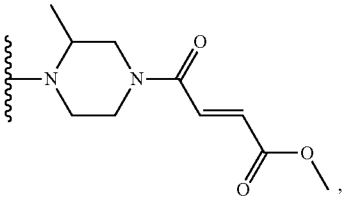

-continued

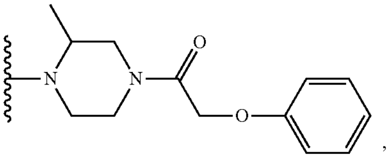
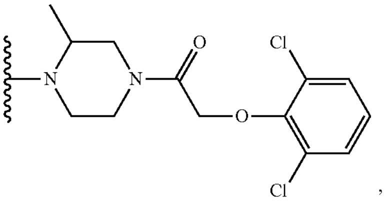
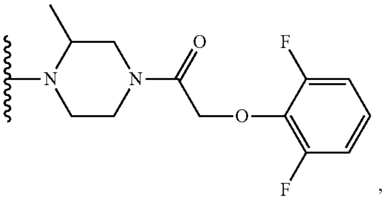
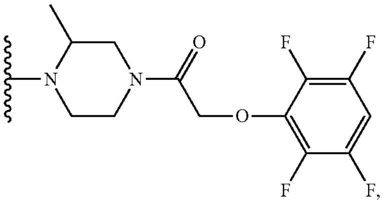
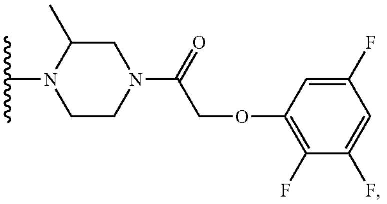
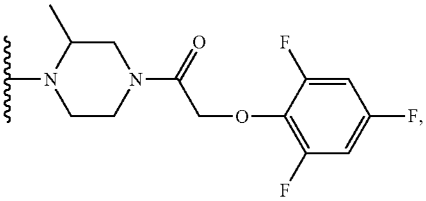
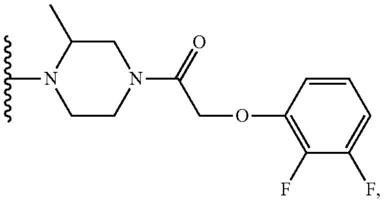
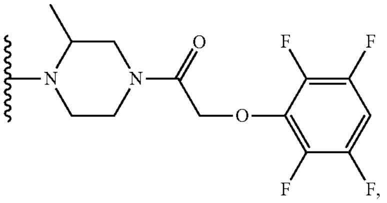

-continued

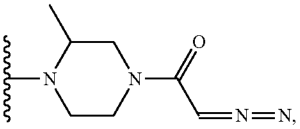,

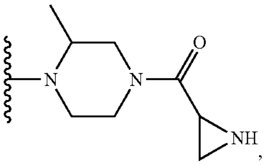,

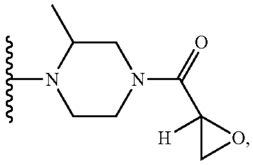,

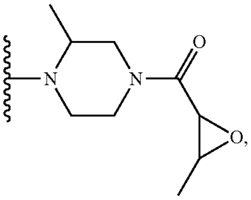,

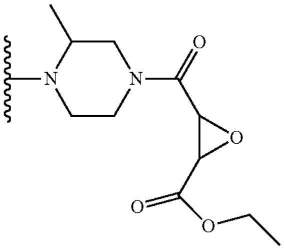,

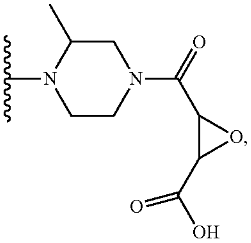,

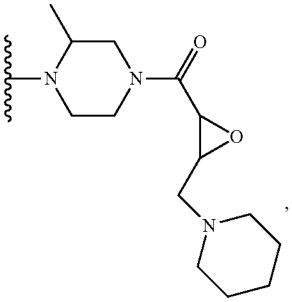,

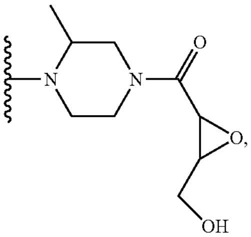,

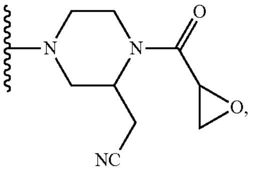,

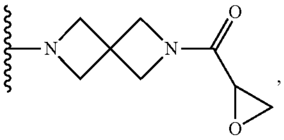,

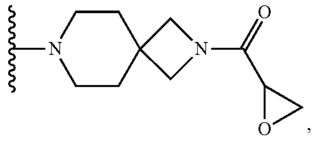,

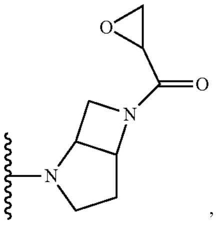,

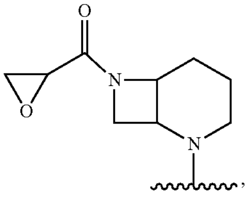, or

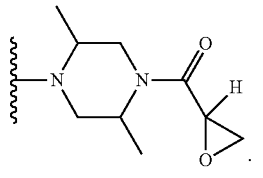.

15. The compound or salt of claim 14, wherein $R^1$ is F.

16. The compound or salt of claim 15, wherein $R^2$ is Cl.

17. The compound or salt of claim 16, wherein $R^8$ is H.

18. The compound or salt of claim 16, wherein $R^8$ is OH.

19. The compound or salt of claim 16, wherein $R^8$ is $NH_2$.

20. A compound, wherein the compound is
(S)-6-chloro-4-(4-(2-chloroacetyl)-2-methylpiperazin-1-yl)-7-(2-fluorophenyl)-1-(2-isopropyl-4-methylpyridin-3-yl)pyrido[2,3-d]pyrimidin-2(1H1)-one,
(S)-6-chloro-4-(4-(2-fluoroacetyl)-2-methylpiperazin-1-yl)-7-(2-fluorophenyl)-1-(2-isopropyl-4-methylpyridin-3-yl)pyrido[2,3-d]pyrimidin-2(1H1)-one,
(S)-1-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)propane-1,2-dione,
(S)-2-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)-2-oxoacetaldehyde,
methyl (S,E)-4-(4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazin-1-yl)-4-oxobut-2-enoate,
(S)-6-chloro-7-(2-fluorophenyl)-1-(2-isopropyl-4-methylpyridin-3-yl)-4-(2-methyl-4-(2-phenoxyacetyl)piperazin-1-yl)pyrido[2,3-d]pyrimidin-2(1H1)-one,
(S)-6-chloro-4-(4-(2-(2,6-dichlorophenoxy)acetyl)-2-methylpiperazin-1-yl)-7-(2-fluorophenyl)-1-(2-isopropyl-4-methylpyridin-3-yl)pyrido[2,3-d]pyrimidin-2(1H1)-one,
(S)-6-chloro-4-(4-(2-(2,6-difluorophenoxy)acetyl)-2-methylpiperazin-1-yl)-7-(2-fluorophenyl)-1-(2-isopropyl-4-methylpyridin-3-yl)pyrido[2,3-d]pyrimidin-2(1H1)-one,
(S)-6-chloro-7-(2-fluorophenyl)-1-(2-isopropyl-4-methylpyridin-3-yl)-4-(2-methyl-4-(2-(2,3,5,6-tetrafluorophenoxy)acetyl)piperazin-1-yl)pyrido[2,3-d]pyrimidin-2(1H)-one,
(S)-6-chloro-7-(2-fluorophenyl)-1-(2-isopropyl-4-methylpyridin-3-yl)-4-(2-methyl-4-(2-(2,3,6-trifluorophenoxy)acetyl)piperazin-1-yl)pyrido[2,3-d]pyrimidin-2(1H)-one,
(S)-6-chloro-7-(2-fluorophenyl)-1-(2-isopropyl-4-methylpyridin-3-yl)-4-(2-methyl-4-(2-(2,4,6-trifluorophenoxy)acetyl)piperazin-1-yl)pyrido[2,3-d]pyrimidin-2(1H1)-one,
(S)-6-chloro-7-(2-fluorophenyl)-1-(2-isopropyl-4-methylpyridin-3-yl)-4-(2-methyl-4-(2-(2,3-difluorophenoxy)acetyl)piperazin-1-yl)pyrido[2,3-d]pyrimidin-2(1H)-one,
(S)-6-chloro-4-(4-(2-diazoacetyl)-2-methylpiperazin-1-yl)-7-(2-fluorophenyl)-1-(2-isopropyl-4-methylpyridin-3-yl)pyrido[2,3-d]pyrimidin-2(1H)-one,
4-((S)-4-((R)-aziridine-2-carbonyl)-2-methylpiperazin-1-yl)-6-chloro-7-(2-fluorophenyl)-1-(2-isopropyl-4-methylpyridin-3-yl)pyrido[2,3-d]pyrimidin-2(1H1)-one,
6-chloro-7-(2-fluorophenyl)-1-(2-isopropyl-4-methylpyridin-3-yl)-4-((S)-2-methyl-4-((S)-oxirane-2-carbonyl)piperazin-1-yl)pyrido[2,3-d]pyrimidin-2(1H1)-one;
6-chloro-7-(2-fluorophenyl)-1-(2-isopropyl-4-methylpyridin-3-yl)-4-((S)-2-methyl-4-((R)-oxirane-2-carbonyl)piperazin-1-yl)pyrido[2,3-d]pyrimidin-2(1H1)-one,
6-chloro-7-(2-fluorophenyl)-1-(2-isopropyl-4-methylpyridin-3-yl)-4-((S)-2-methyl-4-(3-methyloxirane-2-carbonyl)piperazin-1-yl)pyrido[2,3-d]pyrimidin-2(1H)-one,
ethyl (2S,3S)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylate, ethyl (2R,3R)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylate, (2R,3R)-3-((S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carbonyl)oxirane-2-carboxylic acid, 6-chloro-7-(2-fluorophenyl)-1-(2-isopropyl-4-methylpyridin-3-yl)-4-((S)-2-methyl-4-((2R,3S)-3-(piperidin-1-ylmethyl)oxirane-2-carbonyl)piperazin-1-yl)pyrido[2,3-d]pyrimidin-2(1H)-one, 6-chloro-7-(2-fluorophenyl)-4-((S)-4-((2R,3S)-3-(hydroxymethyl)oxirane-2-carbonyl)-2-methylpiperazin-1-yl)-1-(2-isopropyl-4-methylpyridin-3-yl)pyrido[2,3-d]pyrimidin-2(1H1)-one, 2-((2S)-4-(6-chloro-7-(2-fluorophenyl)-1-(2-isopropyl-4-methylpyridin-3-yl)-2-oxo-1,2-dihydropyrido[2,3-d]pyrimidin-4-yl)-1-(oxirane-2-carbonyl)piperazin-2-yl)acetonitrile, 6-chloro-7-(2-fluorophenyl)-1-(2-isopropyl-4-methylpyridin-3-yl)-4-(6-(oxirane-2-carbonyl)-2,6-diazaspiro[3.3]heptan-2-yl)pyrido[2,3-d]pyrimidin-2(1H)-one, (R)-6-chloro-7-(2-fluorophenyl)-1-(2-isopropyl-4-methylpyridin-3-yl)-4-(2-(oxirane-2-carbonyl)-2,7-diazaspiro[3.5]nonan-7-yl)pyrido[2,3-d]pyrimidin-2(1H)-one, N—((R)-1-(6-chloro-7-(2-fluorophenyl)-1-(2-isopropyl-4-methylpyridin-3-yl)-2-oxo-1,2-dihydropyrido[2,3-d]pyrimidin-4-yl)pyrrolidin-3-yl)oxirane-2-carboxamide, N-(1-(6-chloro-7-(2-fluorophenyl)-1-(2-isopropyl-4-methylpyridin-3-yl)-2-oxo-1,2-dihydropyrido[2,3-d]pyrimidin-4-yl)azetidin-3-yl)oxirane-2-carboxamide, 6-chloro-7-(2-fluorophenyl)-1-(2-isopropyl-4-methylpyridin-3-yl)-4-(6-(oxirane-2-carbonyl)-2,6-diazabicyclo[3.2.0]heptan-2-yl)pyrido[2,3-d]pyrimidin-2(1H1)-one, (R)-6-chloro-7-(2-fluorophenyl)-1-(2-isopropyl-4-methylpyridin-3-yl)-4-(methyl(1-(oxirane-2-carbonyl)azetidin-3-yl)amino)pyrido[2,3-d]pyrimidin-2(1H1)-one, 6-chloro-7-(2-fluorophenyl)-1-(2-isopropyl-4-methylpyridin-3-yl)-4-((1-(oxirane-2-carbonyl)azetidin-3-yl)amino)pyrido[2,3-d]pyrimidin-2(1H1)-one, 6-chloro-7-(2-fluorophenyl)-1-(2-isopropyl-4-methylpyridin-3-yl)-4-(((3R)-1-(oxirane-2-carbonyl)pyrrolidin-3-yl)amino)pyrido[2,3-d]pyrimidin-2(1H1)-one, 6-chloro-7-(2-fluorophenyl)-1-(2-isopropyl-4-methylpyridin-3-yl)-4-(7-(oxirane-2-carbonyl)-2,7-diazabicyclo[4.2.0]octan-2-yl)pyrido[2,3-d]pyrimidin-2(1H1)-one, N—((S)-1-(6-chloro-7-(2-fluorophenyl)-1-(2-isopropyl-4-methylpyridin-3-yl)-2-oxo-1,2-dihydropyrido[2,3-d]pyrimidin-4-yl)piperidin-3-yl)oxirane-2-carboxamide, N—((S)-1-(6-chloro-7-(2-fluorophenyl)-1-(2-isopropyl-4-methylpyridin-3-yl)-2-oxo-1,2-dihydropyrido[2,3-d]pyrimidin-4-yl)pyrrolidin-3-yl)oxirane-2-carboxamide, or 6-chloro-4-((2S,5R)-2,5-dimethyl-4-((R)-oxirane-2-carbonyl)piperazin-1-yl)-7-(2-fluoro-6-hydroxyphenyl)-1-(2-isopropyl-4-methylpyridin-3-yl)pyrido[2,3-d]pyrimidin-2(1H)-one;

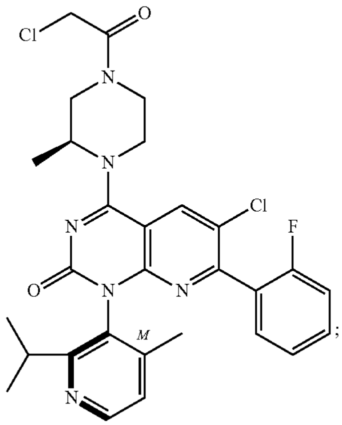
;

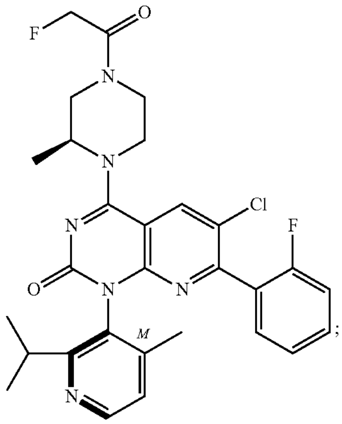
;

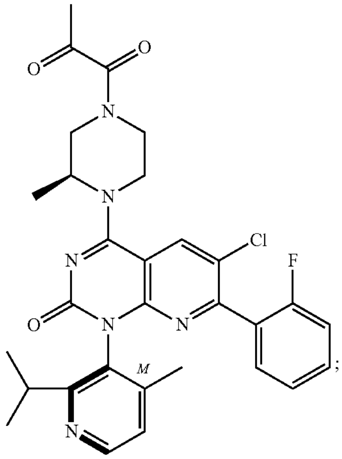
;

-continued
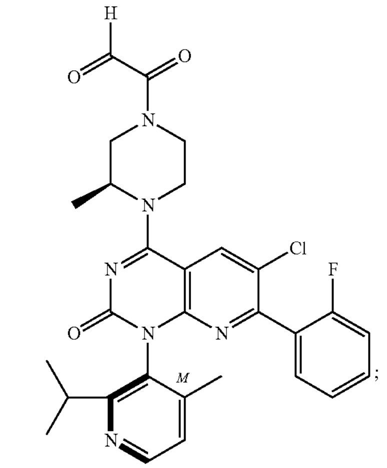
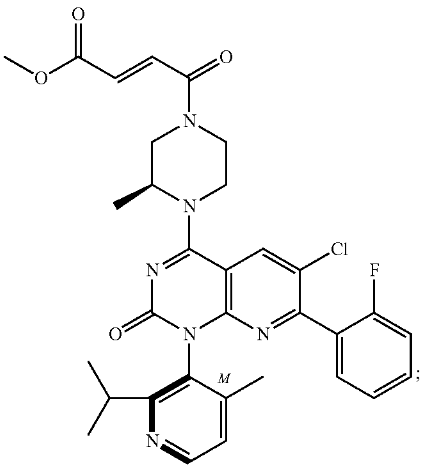
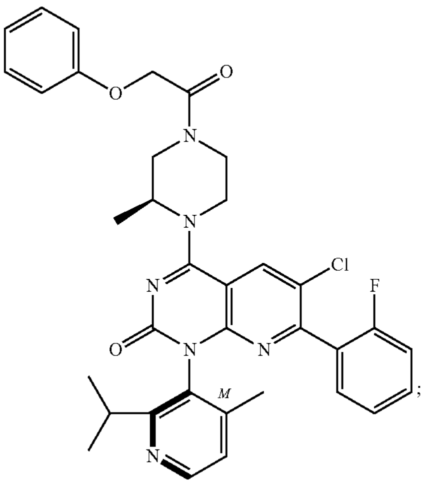
-continued
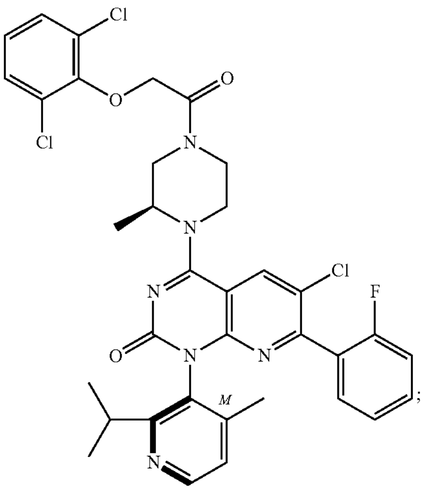
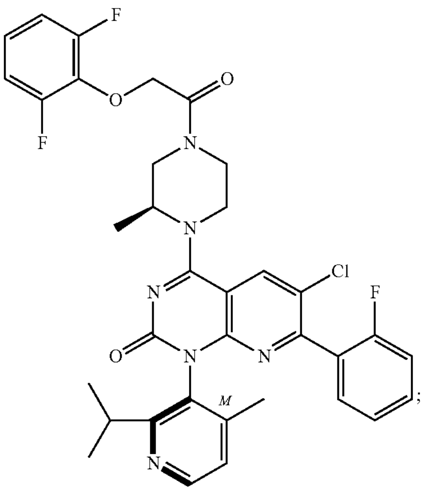
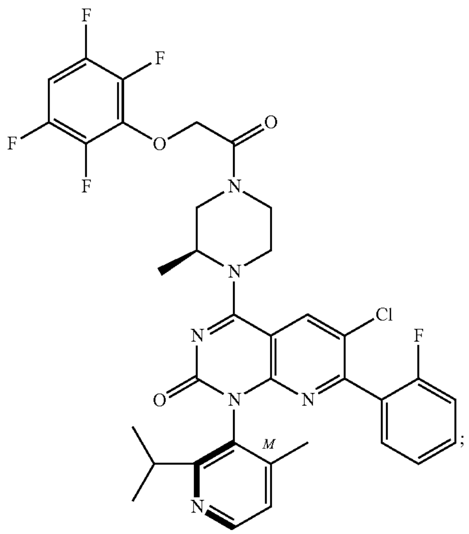

-continued
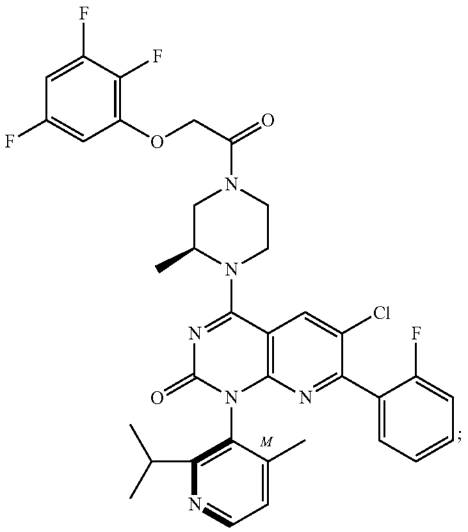
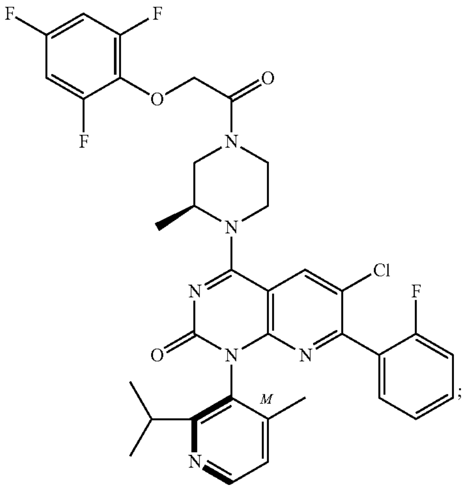
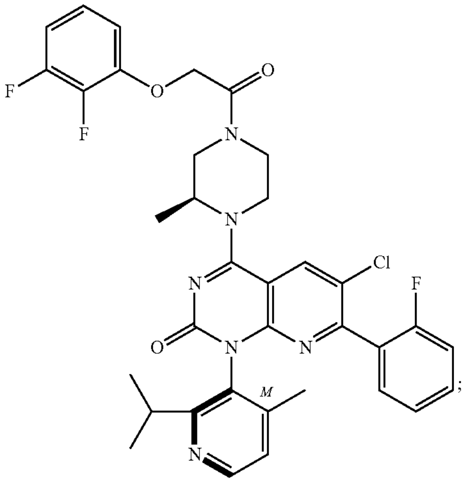
-continued
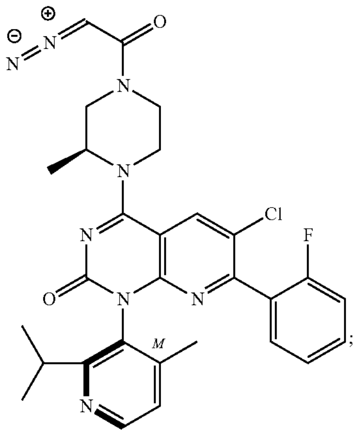
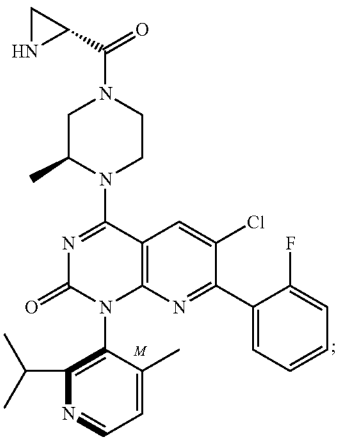
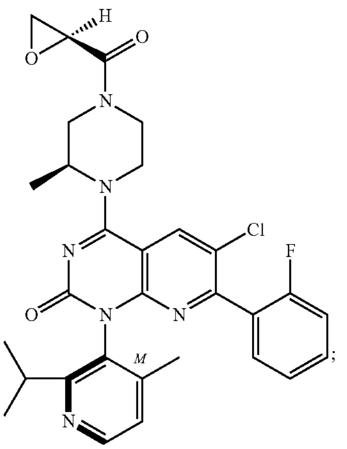

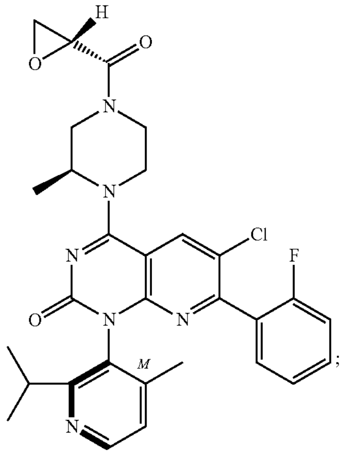
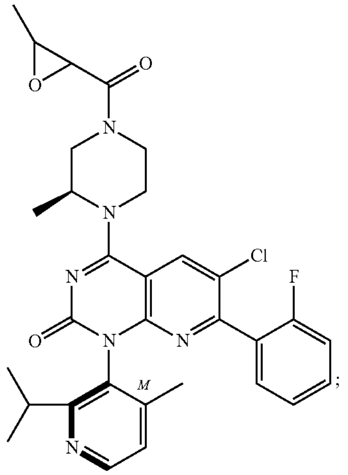
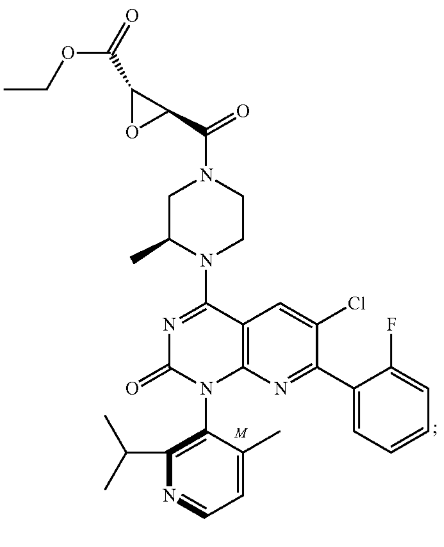
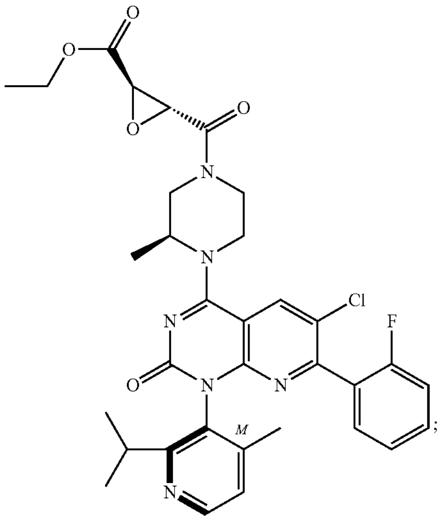
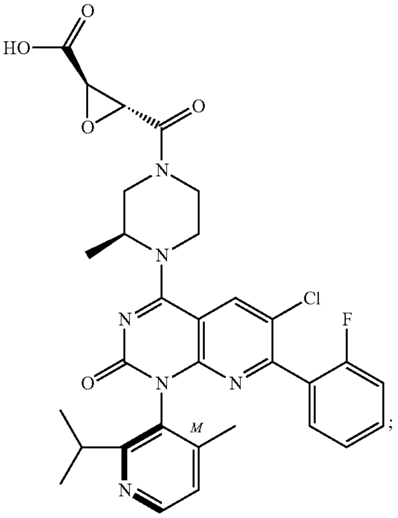
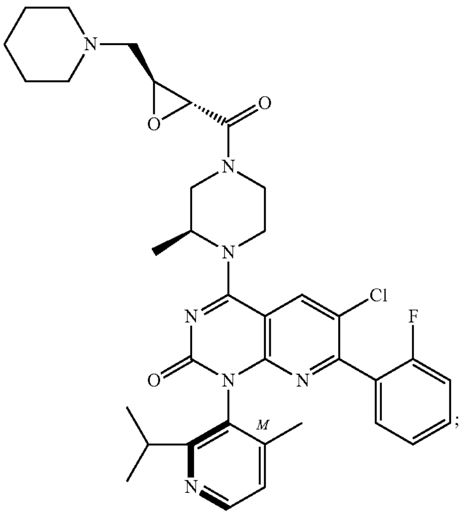

-continued
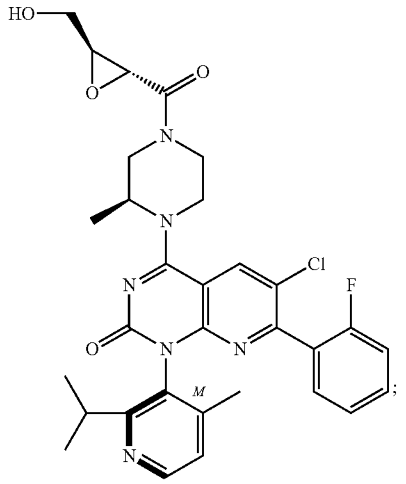
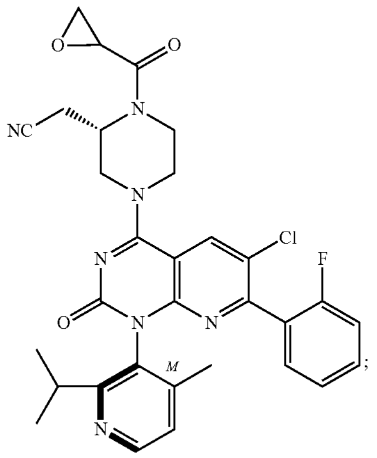
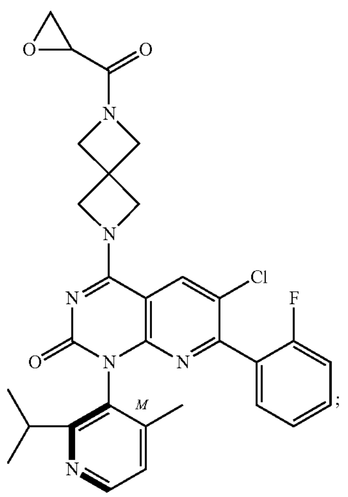
-continued
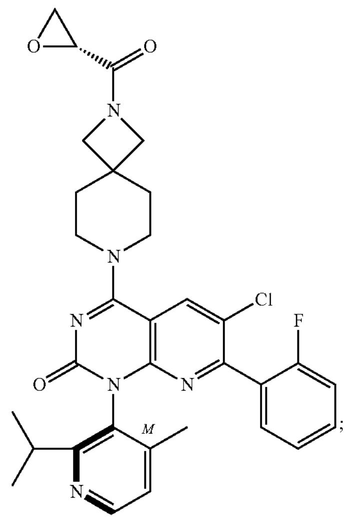
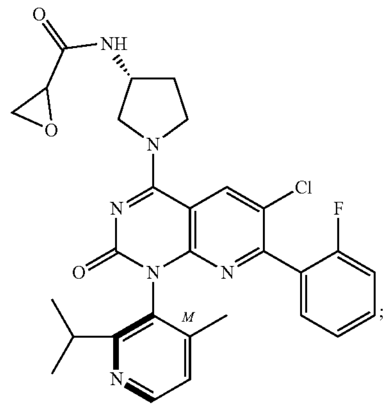
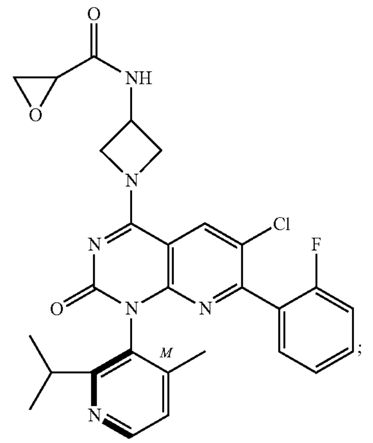

-continued
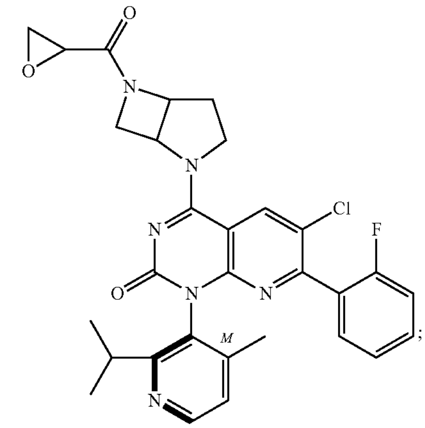
;
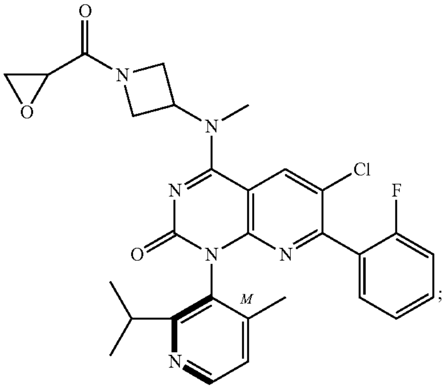
;
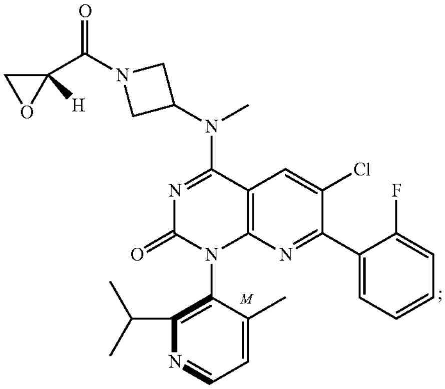
;
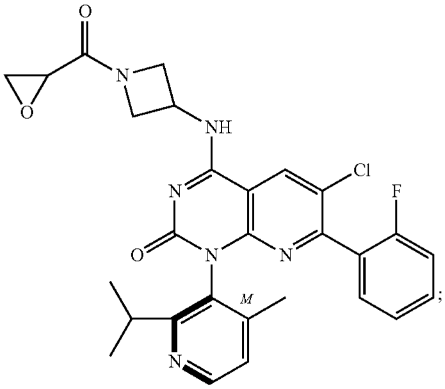
;
-continued
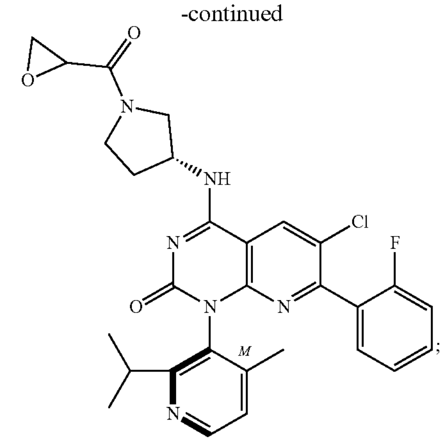
;
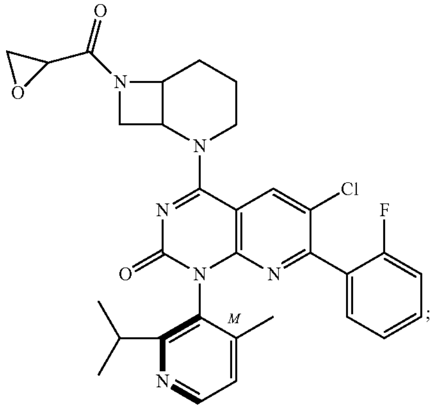
;
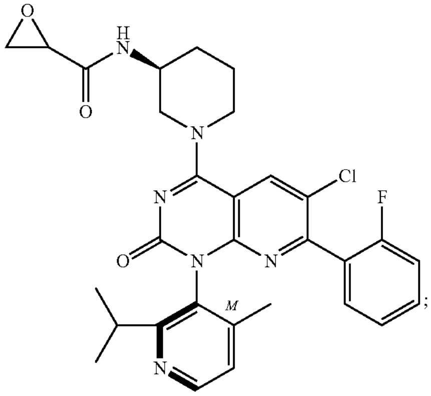
;
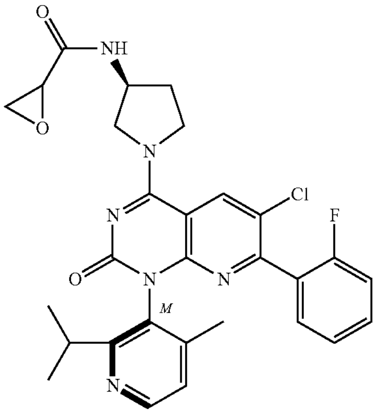

-continued

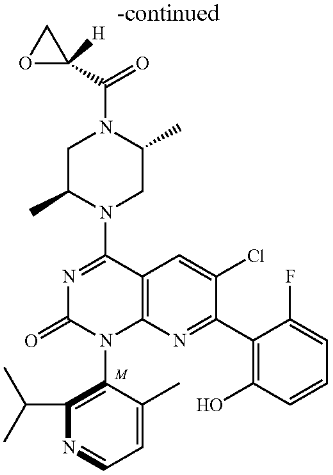

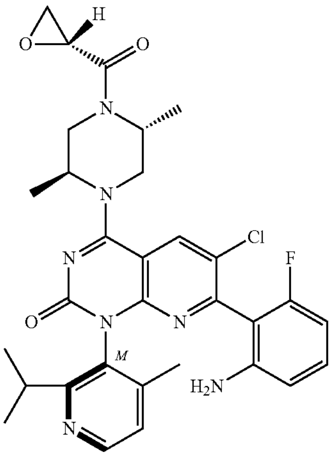

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

21. A pharmaceutical composition comprising the compound or salt of claim 1 and a pharmaceutically acceptable excipient.

22. A pharmaceutical composition comprising the compound or salt of claim 20 and a pharmaceutically acceptable excipient.

23. A compound having a structure of formula (I)

(I)

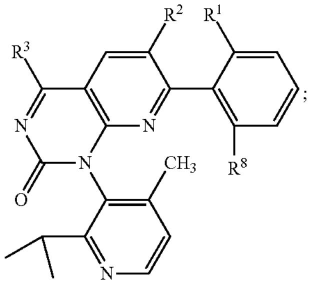

;

wherein $R^1$ is F;

$R^2$ is H, halo, or —$CH_3$;

$R^3$ is

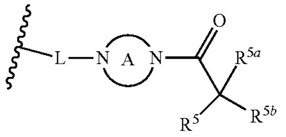

or

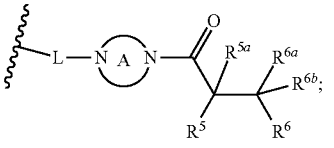

;

ring A is a monocyclic 4-7 membered ring;

L is a bond;

$R^5$ is F or Cl, wherein $R^3$ is

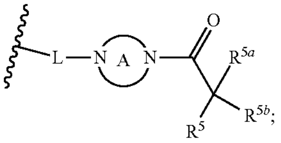

;

$R^5$ is H, wherein $R^3$ is

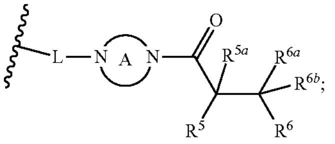

;

$R^{5a}$ is H;

$R^{5b}$ is H;

$R^6$ is halo;

$R^{6a}$ is H;

$R^{6b}$ is H;

$R^8$ is H or OH; and wherein the ring A is unsubstituted or substituted with 1, 2, 3, or 4 substituents, as allowed, independently selected from halo, —$C_{1-6}$ alkyl, —O—$C_{1-6}$ alkyl, —OH, or —$C_{1-6}$ alkyl-CN; or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

24. The compound or salt of claim 23, wherein $R^3$ is

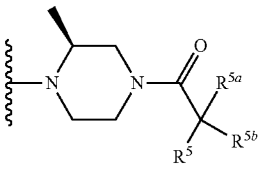

or

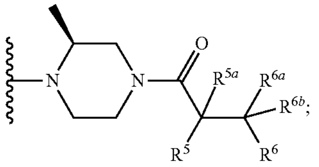

;

25. The compound or salt of claim 24, wherein $R^3$ is
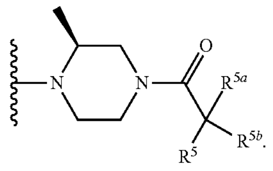
26. The compound or salt of claim 24, wherein $R^3$ is
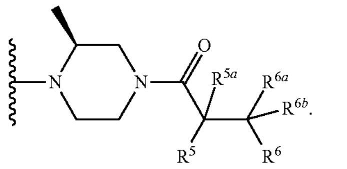
27. The compound or salt of claim 25, wherein
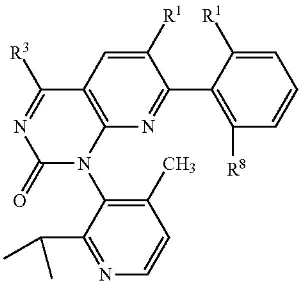
is
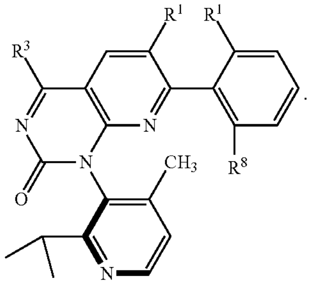
28. The compound or salt of claim 26, wherein
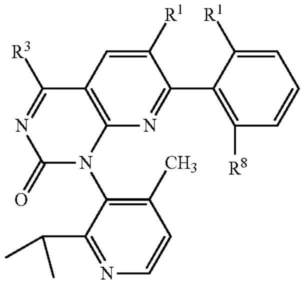
is
-continued
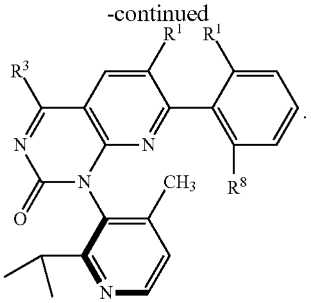
29. A process of making a compound having a structure of formula (I)
(I)
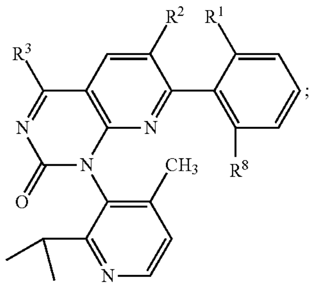
wherein
$R^1$ is F;
$R^2$ is H, halo, or —$CH_3$;
$R^3$ is
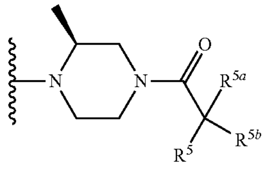
or
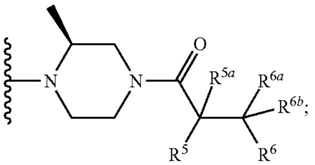
$R^5$ is F or Cl, wherein $R^3$ is
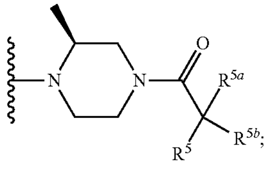

$R^5$ is H, wherein $R^3$ is

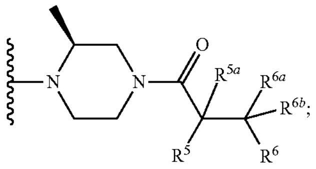

$R^{5a}$ is H;
$R^{5b}$ is H;
$R^6$ is halo;
$R^{6a}$ is H;
$R^{6b}$ is H; and
$R^8$ is H or OH; or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof; and wherein the process comprises at least one of the following steps:

(a) reacting

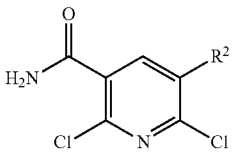

with $(COCl)_2$ and

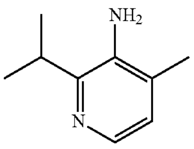

to form

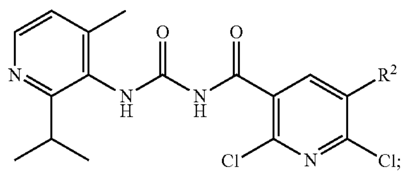

or (b) reacting

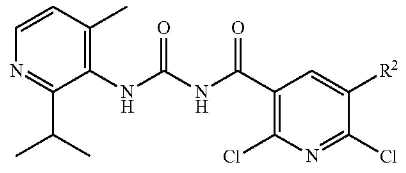

with a base to form

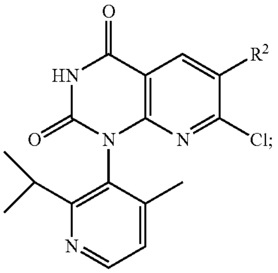

or (c) transforming

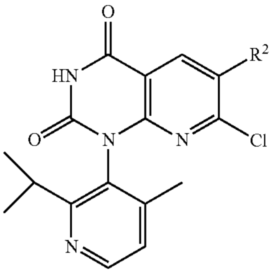

into

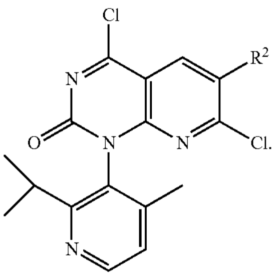

30. The process of claim 29, wherein

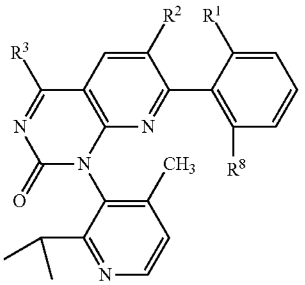

is

-continued
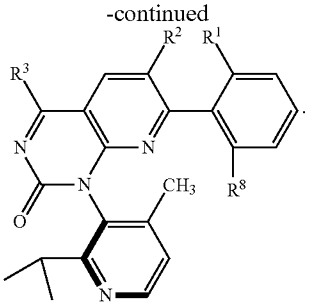
31. The process of claim 29, wherein $R^3$ is
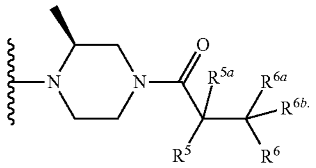
32. The process of claim 31, wherein $R^2$ is halo.
33. The process of claim 32, wherein the process comprises reacting
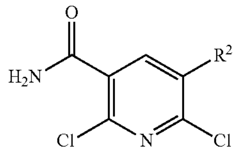
with $(COCl)_2$ and
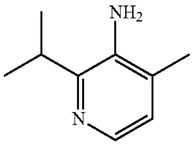
to form
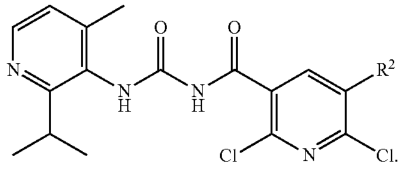
34. The process of claim 32, wherein the process comprises reacting
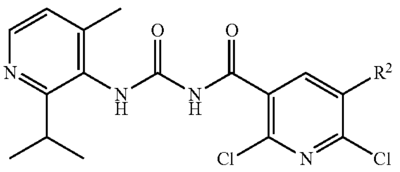
with a base to form
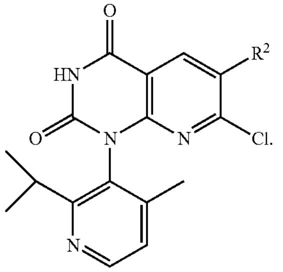
35. The process of claim 32, wherein the process comprises transforming
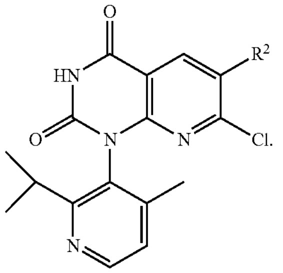
into
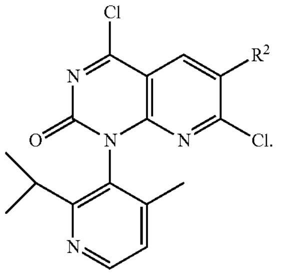
* * * * *